US010058323B2

(12) United States Patent
Maisano

(10) Patent No.: US 10,058,323 B2
(45) Date of Patent: Aug. 28, 2018

(54) TRICUSPID VALVE REPAIR USING TENSION

(71) Applicant: 4 TECH INC., Waltham, MA (US)

(72) Inventor: Francesco Maisano, Zürich (CH)

(73) Assignee: 4 TECH INC., Waltham, MA (US)

(*) Notice: Subject to any disclaimer, the term of this patent is extended or adjusted under 35 U.S.C. 154(b) by 11 days.

(21) Appl. No.: 15/608,256

(22) Filed: May 30, 2017

(65) Prior Publication Data

US 2017/0258465 A1 Sep. 14, 2017

Related U.S. Application Data

(63) Continuation of application No. 13/574,088, filed as application No. PCT/IL2011/000064 on Jan. 20,
(Continued)

(51) Int. Cl.
*A61F 2/24* (2006.01)
*A61B 17/04* (2006.01)
(Continued)

(52) U.S. Cl.
CPC ........ *A61B 17/0401* (2013.01); *A61F 2/2442* (2013.01); *A61F 2/2487* (2013.01);
(Continued)

(58) Field of Classification Search
CPC ............ A61F 2/245; A61F 2002/30537; A61F 2220/0016; A61F 2250/0004;
(Continued)

(56) References Cited

U.S. PATENT DOCUMENTS

| 3,874,388 A | 4/1975 | King et al. |
| 4,214,349 A | 7/1980 | Munch |

(Continued)

FOREIGN PATENT DOCUMENTS

| DE | 102007043830 | 4/2009 |
| EP | 1568326 | 8/2005 |

(Continued)

OTHER PUBLICATIONS

An International Search Report and a Written Opinion both dated Dec. 6, 2013, which issued during the prosecution of Applicant's PCT/IL2013/050470.
(Continued)

*Primary Examiner* — Seema Mathew
(74) *Attorney, Agent, or Firm* — Ultimatedge IP Law Group, P.C.; Dean G. Stathakis; Vito A. Canuso, III

(57) ABSTRACT

A method is provided for reducing tricuspid valve regurgitation of a patient. The method includes implanting a first tissue anchor at a first implantation site in cardiac tissue in the vicinity of the tricuspid valve of the patient, and implanting a second tissue anchor at a second implantation site in cardiac tissue of the patient opposite the first implantation site across the tricuspid valve. Using a spool that winds therewithin at least a portion of a longitudinal member that couples the first and the second tissue anchors together, tension is applied between the first and the second tissue anchors to alter the geometry of the tricuspid valve by rotating the spool.

2 Claims, 34 Drawing Sheets

Related U.S. Application Data 2011, which is a continuation-in-part of application No. 12/692,061, filed on Jan. 22, 2010, now Pat. No. 8,475,525.

(51) Int. Cl.
*A61F 2/915* (2013.01)
*A61B 17/00* (2006.01)
*A61F 2/90* (2013.01)

(52) U.S. Cl.
CPC .... *A61F 2/915* (2013.01); *A61B 2017/00243* (2013.01); *A61B 2017/048* (2013.01); *A61B 2017/0412* (2013.01); *A61B 2017/0414* (2013.01); *A61B 2017/0464* (2013.01); *A61B 2017/0496* (2013.01); *A61F 2/2454* (2013.01); *A61F 2/2457* (2013.01); *A61F 2/90* (2013.01); *A61F 2220/0008* (2013.01); *A61F 2230/0091* (2013.01)

(58) Field of Classification Search
CPC .... A61F 2/2409; A61F 2/2427; A61F 2/2445; A61F 2/2451; A61F 2/2457; A61F 2250/0007; A61F 2/2442; A61B 17/0401; A61B 2017/00243; A61B 2017/0496; A61B 2017/048; A61B 2017/12095; A61B 2017/0443; A61B 2017/0412
See application file for complete search history.

(56) References Cited

U.S. PATENT DOCUMENTS

| | | |
|---|---|---|
| 4,405,313 A | 9/1983 | Sisley et al. |
| 4,423,525 A | 1/1984 | Vallana |
| 4,444,207 A | 4/1984 | Robicsek |
| 4,493,329 A | 1/1985 | Crawford et al. |
| 4,532,926 A | 8/1985 | O'Holla |
| 4,548,202 A | 10/1985 | Duncan |
| 4,602,911 A | 7/1986 | Ahmadi et al. |
| 4,625,727 A | 12/1986 | Leiboff |
| 4,712,549 A | 12/1987 | Peters et al. |
| 4,741,336 A | 5/1988 | Failla et al. |
| 4,778,468 A | 10/1988 | Hunt et al. |
| 4,808,157 A | 2/1989 | Coombs |
| 4,853,986 A | 8/1989 | Allen |
| 5,108,420 A | 4/1992 | Marks |
| 5,330,521 A | 7/1994 | Cohen |
| 5,336,233 A | 8/1994 | Chen |
| 5,350,399 A | 9/1994 | Erlebacher et al. |
| 5,450,860 A | 9/1995 | O'Connor |
| 5,473,812 A | 12/1995 | Morris et al. |
| 5,474,518 A | 12/1995 | Farrer-Velazquez |
| 5,702,343 A | 12/1997 | Alferness et al. |
| 5,776,178 A | 7/1998 | Pohndorf et al. |
| 5,792,400 A | 8/1998 | Talja et al. |
| 5,843,120 A | 12/1998 | Israel |
| 5,843,164 A | 12/1998 | Frantzen et al. |
| 5,904,697 A | 5/1999 | Gifford et al. |
| 5,948,000 A | 9/1999 | Larsen et al. |
| 5,957,953 A | 9/1999 | DiPoto et al. |
| 5,961,440 A | 10/1999 | Schweich, Jr. et al. |
| 6,010,113 A | 1/2000 | Rotering |
| 6,024,756 A | 2/2000 | Huebsch et al. |
| 6,027,523 A | 2/2000 | Schmieding |
| 6,045,497 A | 4/2000 | Schweich, Jr. et al. |
| 6,050,936 A | 4/2000 | Schweich, Jr. et al. |
| 6,077,214 A | 6/2000 | Mortier et al. |
| 6,183,512 B1 | 2/2001 | Howanec et al. |
| 6,193,734 B1 | 2/2001 | Bolduc et al. |
| 6,206,913 B1 | 3/2001 | Yencho et al. |
| 6,210,432 B1 | 4/2001 | Solem et al. |
| 6,231,516 B1 | 5/2001 | Keilman et al. |
| 6,260,552 B1 | 7/2001 | Mortier et al. |
| 6,298,272 B1 | 10/2001 | Peterfeso et al. |
| 6,299,635 B1 | 10/2001 | Frantzen |
| 6,332,893 B1 | 12/2001 | Mortier et al. |
| 6,338,738 B1 | 1/2002 | Bellotti et al. |
| 6,402,780 B2 | 6/2002 | Williamson, IV et al. |
| 6,402,781 B1 | 6/2002 | Langberg et al. |
| 6,406,420 B1 | 6/2002 | McCarthy et al. |
| 6,461,336 B1 | 10/2002 | Larre |
| 6,533,810 B2 | 3/2003 | Hankh et al. |
| 6,537,198 B1 | 3/2003 | Vidlund et al. |
| 6,537,314 B2 | 3/2003 | Langberg et al. |
| 6,575,976 B2 | 6/2003 | Grafton |
| 6,585,766 B1 | 7/2003 | Huynh et al. |
| 6,602,288 B1 | 8/2003 | Cosgrove et al. |
| 6,613,078 B1 | 9/2003 | Barone |
| 6,613,079 B1 | 9/2003 | Wolinsky |
| 6,616,684 B1 | 9/2003 | Vidlund et al. |
| 6,619,291 B2 | 9/2003 | Hlavka et al. |
| 6,622,730 B2 | 9/2003 | Ekvall et al. |
| 6,626,899 B2 | 9/2003 | Houser et al. |
| 6,626,930 B1 | 9/2003 | Allen et al. |
| 6,629,534 B1 * | 10/2003 | St. Goar .......... A61B 17/00234 128/898 |
| 6,629,921 B1 | 10/2003 | Schweich, Jr. et al. |
| 6,641,597 B2 | 11/2003 | Burkhart et al. |
| 6,645,193 B2 | 11/2003 | Mangosong |
| 6,669,687 B1 | 12/2003 | Saadat |
| 6,695,768 B1 | 2/2004 | Levine et al. |
| 6,702,846 B2 | 3/2004 | Mikus |
| 6,709,456 B2 | 3/2004 | Langberg et al. |
| 6,718,985 B2 | 4/2004 | Hlavka et al. |
| 6,719,767 B1 | 4/2004 | Kimblad |
| 6,723,038 B1 | 4/2004 | Schroeder et al. |
| 6,730,118 B2 | 5/2004 | Spenser et al. |
| 6,743,198 B1 | 6/2004 | Tihon |
| 6,746,472 B2 | 6/2004 | Frazier et al. |
| 6,764,510 B2 | 7/2004 | Vidlund et al. |
| 6,776,754 B1 | 8/2004 | Wilk |
| 6,797,001 B2 | 9/2004 | Mathis |
| 6,810,882 B2 | 11/2004 | Langberg et al. |
| 6,884,250 B2 | 4/2005 | Monassevitch |
| 6,893,459 B1 | 5/2005 | Macoviak |
| 6,908,478 B2 | 6/2005 | Alferness et al. |
| 6,929,660 B1 | 8/2005 | Ainsworth et al. |
| 6,989,028 B2 | 1/2006 | Lashinski et al. |
| 6,997,951 B2 | 2/2006 | Solem et al. |
| 7,011,682 B2 | 3/2006 | Lashinski et al. |
| 7,018,406 B2 | 3/2006 | Seguin et al. |
| 7,018,408 B2 | 3/2006 | Bailey et al. |
| 7,037,290 B2 | 5/2006 | Gardeski et al. |
| 7,041,097 B1 | 5/2006 | Webler |
| 7,044,967 B1 | 5/2006 | Solem et al. |
| 7,056,333 B2 | 6/2006 | Walshe |
| 7,063,711 B1 | 6/2006 | Loshakove et al. |
| 7,077,861 B2 | 7/2006 | Spence |
| 7,083,628 B2 | 8/2006 | Bachman |
| 7,087,064 B1 | 8/2006 | Hyde |
| 7,094,244 B2 | 8/2006 | Schreck |
| 7,101,395 B2 | 9/2006 | Tremulis et al. |
| 7,101,396 B2 | 9/2006 | Artof et al. |
| 7,112,219 B2 | 9/2006 | Vidlund et al. |
| 7,125,421 B2 | 10/2006 | Tremulis et al. |
| 7,144,363 B2 | 12/2006 | Pai et al. |
| 7,159,593 B2 | 1/2007 | McCarthy et al. |
| 7,166,127 B2 | 1/2007 | Spence et al. |
| 7,169,187 B2 | 1/2007 | Datta |
| 7,175,625 B2 | 2/2007 | Culbert |
| 7,179,282 B2 | 2/2007 | Alferness et al. |
| 7,186,262 B2 | 3/2007 | Saadat |
| 7,189,199 B2 | 3/2007 | McCarthy et al. |
| 7,192,442 B2 | 3/2007 | Solem et al. |
| 7,192,443 B2 | 3/2007 | Solem et al. |
| 7,198,646 B2 | 4/2007 | Figulla et al. |
| 7,201,772 B2 | 4/2007 | Schwammenthal |
| 7,211,107 B2 | 5/2007 | Bruckheimer et al. |
| 7,211,110 B2 | 5/2007 | Rowe et al. |
| 7,241,257 B1 | 7/2007 | Ainsworth et al. |
| 7,247,134 B2 | 7/2007 | Vidlund et al. |
| 7,258,697 B1 | 8/2007 | Cox et al. |
| 7,291,168 B2 | 11/2007 | Macoviak et al. |

(56) References Cited

U.S. PATENT DOCUMENTS

| | | |
|---|---|---|
| 7,311,697 B2 | 12/2007 | Osborne |
| 7,311,728 B2 | 12/2007 | Solem et al. |
| 7,316,706 B2 | 1/2008 | Bloom et al. |
| 7,316,710 B1 | 1/2008 | Cheng et al. |
| 7,329,279 B2 | 2/2008 | Haug et al. |
| 7,331,972 B1 | 2/2008 | Cox |
| 7,335,213 B1 | 2/2008 | Hyde et al. |
| 7,338,506 B2 | 3/2008 | Caro |
| 7,351,256 B2 | 4/2008 | Hojeibane |
| 7,371,244 B2 | 5/2008 | Chatlynne et al. |
| 7,374,573 B2 | 5/2008 | Gabbay |
| 7,381,210 B2 | 6/2008 | Zarbatany et al. |
| 7,381,220 B2 | 6/2008 | Macoviak et al. |
| 7,390,329 B2 | 6/2008 | Westra et al. |
| 7,431,692 B2 | 10/2008 | Zollinger et al. |
| 7,431,726 B2 | 10/2008 | Spence et al. |
| 7,485,143 B2 | 2/2009 | Webler et al. |
| 7,500,989 B2 | 3/2009 | Solem et al. |
| 7,503,931 B2 | 3/2009 | Kowalsky et al. |
| 7,510,575 B2 | 3/2009 | Spenser et al. |
| 7,527,646 B2 | 5/2009 | Randert et al. |
| 7,530,995 B2 | 5/2009 | Quijano et al. |
| 7,547,321 B2 | 6/2009 | Silvestri et al. |
| 7,549,983 B2 | 6/2009 | Roue et al. |
| 7,597,703 B2 | 10/2009 | Sater |
| 7,608,102 B2 | 10/2009 | Adams et al. |
| 7,618,449 B2 | 11/2009 | Tremulis et al. |
| 7,628,797 B2 | 12/2009 | Tieu et al. |
| 7,632,303 B1 | 12/2009 | Stalker et al. |
| 7,637,946 B2 | 12/2009 | Solem et al. |
| 7,666,204 B2 | 2/2010 | Thornton et al. |
| 7,695,512 B2 | 4/2010 | Lashinski et al. |
| 7,704,277 B2 | 4/2010 | Zakay et al. |
| 7,722,523 B2 | 5/2010 | Mortier et al. |
| 7,758,632 B2 | 7/2010 | Hojeibane et al. |
| 7,766,816 B2 | 8/2010 | Chin et al. |
| 7,771,467 B2 | 8/2010 | Svensson |
| 7,780,726 B2 | 8/2010 | Seguin |
| 7,785,366 B2 | 8/2010 | Maurer et al. |
| 7,803,187 B2 | 9/2010 | Hauser |
| 7,806,910 B2 | 10/2010 | Anderson |
| 7,837,727 B2 | 11/2010 | Goetz et al. |
| 7,841,502 B2 | 11/2010 | Walberg et al. |
| 7,857,846 B2 | 12/2010 | Alferness et al. |
| 7,871,433 B2 | 1/2011 | Lattouf |
| 7,883,539 B2 | 2/2011 | Schweich, Jr. et al. |
| 7,892,214 B2 | 2/2011 | Kagan |
| 7,930,016 B1 | 4/2011 | Saadat |
| 7,942,927 B2 | 5/2011 | Kaye et al. |
| 7,947,207 B2 | 5/2011 | Mcniven et al. |
| 7,972,378 B2 | 7/2011 | Tabor et al. |
| 7,991,484 B1 | 8/2011 | Sengupta et al. |
| 7,992,567 B2 | 8/2011 | Hirotsuka |
| 7,993,368 B2 | 8/2011 | Gambale et al. |
| 7,993,397 B2 | 8/2011 | Lashinski et al. |
| 8,010,207 B2 | 8/2011 | Smits et al. |
| 8,025,495 B2 | 9/2011 | Hardert et al. |
| 8,029,518 B2 | 10/2011 | Goldfarb et al. |
| 8,052,592 B2 | 11/2011 | Goldfarb et al. |
| 8,075,616 B2 | 12/2011 | Solem et al. |
| 8,092,517 B2 | 1/2012 | Kalmann et al. |
| 8,092,520 B2 | 1/2012 | Quadri |
| 8,092,525 B2 | 1/2012 | Eliasen et al. |
| 8,100,820 B2 | 1/2012 | Hauser et al. |
| 8,108,054 B2 | 1/2012 | Helland |
| 8,109,996 B2 | 2/2012 | Stacchino et al. |
| 8,137,381 B2 | 3/2012 | Foerster et al. |
| 8,142,493 B2 | 3/2012 | Spence et al. |
| 8,142,495 B2 | 3/2012 | Hasenkam et al. |
| 8,147,542 B2 | 4/2012 | Maisano et al. |
| 8,157,810 B2 | 4/2012 | Case et al. |
| 8,172,898 B2 | 5/2012 | Alferness et al. |
| 8,197,441 B2 | 6/2012 | Webler et al. |
| 8,202,281 B2 | 6/2012 | Voss |
| 8,202,315 B2 | 6/2012 | Hlavka et al. |
| 8,216,302 B2 | 7/2012 | Wilson et al. |
| 8,226,707 B2 | 7/2012 | White |
| 8,236,013 B2 | 8/2012 | Chu |
| 8,236,049 B2 | 8/2012 | Rowe et al. |
| 8,252,005 B2 | 8/2012 | Findlay et al. |
| 8,262,567 B2 | 9/2012 | Sharp et al. |
| 8,262,724 B2 | 9/2012 | Seguin et al. |
| 8,262,725 B2 | 9/2012 | Subramanian |
| 8,267,981 B2 | 9/2012 | Boock et al. |
| 8,313,497 B2 | 11/2012 | Walberg et al. |
| 8,313,498 B2 | 11/2012 | Pantages et al. |
| 8,323,312 B2 | 12/2012 | Clark |
| 8,323,335 B2 | 12/2012 | Rowe et al. |
| 8,332,051 B2 | 12/2012 | Sommer et al. |
| 8,361,088 B2 | 1/2013 | McIntosh |
| 8,382,829 B1 | 2/2013 | Call et al. |
| 8,394,008 B2 | 3/2013 | Annest et al. |
| 8,398,672 B2 | 3/2013 | Kleshinski et al. |
| 8,409,273 B2 | 4/2013 | Thornton et al. |
| 8,419,753 B2 | 4/2013 | Stafford |
| 8,430,893 B2 | 4/2013 | Ma |
| 8,449,606 B2 | 5/2013 | Eliasen et al. |
| 8,460,368 B2 | 6/2013 | Taylor et al. |
| 8,460,371 B2 | 6/2013 | Hlavka et al. |
| 8,475,525 B2 | 7/2013 | Maisano et al. |
| 8,480,691 B2 | 7/2013 | Dana et al. |
| 8,480,730 B2 | 7/2013 | Maurer et al. |
| 8,523,881 B2 | 9/2013 | Cabiri et al. |
| 8,524,132 B2 | 9/2013 | Von Oepen et al. |
| 8,529,621 B2 | 9/2013 | Alfieri et al. |
| 8,545,553 B2 | 10/2013 | Zipory et al. |
| 8,568,475 B2 | 10/2013 | Nguyen et al. |
| 8,568,476 B2 | 10/2013 | Rao et al. |
| 8,591,460 B2 | 11/2013 | Wilson et al. |
| 8,597,347 B2 | 12/2013 | Maurer et al. |
| 8,628,569 B2 | 1/2014 | Benichou et al. |
| 8,628,571 B1 | 1/2014 | Hacohen |
| 8,663,248 B2 | 3/2014 | Zung et al. |
| 8,685,080 B2 | 4/2014 | White |
| 8,685,083 B2 | 4/2014 | Perier et al. |
| 8,721,588 B2 | 5/2014 | Echarri et al. |
| 8,728,097 B1 | 5/2014 | Sugimoto et al. |
| 8,747,463 B2 | 6/2014 | Fogarty et al. |
| 8,753,357 B2 | 6/2014 | Roorda et al. |
| 8,753,373 B2 | 6/2014 | Chau et al. |
| 8,758,402 B2 | 6/2014 | Jenson et al. |
| 8,778,017 B2 | 7/2014 | Eliasen et al. |
| 8,784,481 B2 | 7/2014 | Alkhatib et al. |
| 8,790,394 B2 | 7/2014 | Miller et al. |
| 8,795,356 B2 | 8/2014 | Quadri et al. |
| 8,808,366 B2 | 8/2014 | Braido et al. |
| 8,808,368 B2 | 8/2014 | Maisano et al. |
| 8,845,723 B2 | 9/2014 | Spence et al. |
| 8,852,270 B2 | 10/2014 | Maurer et al. |
| 8,852,272 B2 | 10/2014 | Gross et al. |
| 8,858,594 B2 | 10/2014 | Clark |
| 8,858,623 B2 | 10/2014 | Miller et al. |
| 8,864,822 B2 | 10/2014 | Spence et al. |
| 8,870,949 B2 | 10/2014 | Rowe |
| 8,870,950 B2 | 10/2014 | Hacohen |
| 8,893,947 B2 | 11/2014 | Reynolds et al. |
| 8,911,461 B2 | 12/2014 | Traynor et al. |
| 8,926,691 B2 | 1/2015 | Chau et al. |
| 8,945,177 B2 | 2/2015 | Dell et al. |
| 8,945,211 B2 | 2/2015 | Sugimoto |
| 8,951,285 B2 | 2/2015 | Sugimoto et al. |
| 8,961,594 B2 | 2/2015 | Maisano et al. |
| 8,961,595 B2 | 2/2015 | Alkhatib |
| 8,961,596 B2 | 2/2015 | Maisano et al. |
| 8,968,335 B2 | 3/2015 | Robinson et al. |
| 8,968,336 B2 | 3/2015 | Conklin et al. |
| 8,968,395 B2 | 3/2015 | Hauser et al. |
| 8,979,750 B2 | 3/2015 | Van Bladel et al. |
| 8,979,922 B2 | 3/2015 | Jayasinghe et al. |
| 8,979,923 B2 | 3/2015 | Spence et al. |
| 9,005,273 B2 | 4/2015 | Salahieh et al. |
| 9,011,468 B2 | 4/2015 | Ketai et al. |
| 9,017,347 B2 | 4/2015 | Oba et al. |
| 9,034,032 B2 | 5/2015 | McLean et al. |

(56) References Cited

U.S. PATENT DOCUMENTS

| | | |
|---|---|---|
| 9,034,033 B2 | 5/2015 | McLean et al. |
| 9,078,652 B2 | 7/2015 | Conklin et al. |
| 9,084,676 B2 | 7/2015 | Chau et al. |
| 9,107,749 B2 | 8/2015 | Bobo et al. |
| 9,131,939 B1 | 9/2015 | Call et al. |
| 9,138,335 B2 | 9/2015 | Cartledge et al. |
| 9,180,005 B1 | 11/2015 | Lashinski et al. |
| 9,192,471 B2 | 11/2015 | Bolling |
| 9,211,115 B2 | 12/2015 | Annest et al. |
| 9,211,203 B2 | 12/2015 | Pike et al. |
| 9,241,702 B2 | 1/2016 | Maisano et al. |
| 9,241,706 B2 | 1/2016 | Paraschac et al. |
| 9,259,218 B2 | 2/2016 | Robinson |
| 9,259,317 B2 | 2/2016 | Wilson et al. |
| 9,282,965 B2 | 3/2016 | Kokish |
| 9,289,282 B2 | 3/2016 | Olson et al. |
| 9,289,297 B2 | 3/2016 | Wilson et al. |
| 9,301,749 B2 | 4/2016 | Rowe et al. |
| 9,314,242 B2 | 4/2016 | Bachman |
| 9,326,870 B2 | 5/2016 | Berglund et al. |
| 9,358,111 B2 | 6/2016 | Spence et al. |
| 9,408,607 B2 | 8/2016 | Cartledge et al. |
| 9,474,605 B2 | 10/2016 | Rowe et al. |
| 9,662,212 B2 | 5/2017 | Van Bladel et al. |
| 9,907,681 B2 * | 3/2018 | Tobis .................. A61F 2/88 |
| 2001/0018611 A1 | 8/2001 | Solem et al. |
| 2002/0013571 A1 | 1/2002 | Goldfarb et al. |
| 2002/0032481 A1 | 5/2002 | Gabbay |
| 2002/0082625 A1 | 6/2002 | Huxel et al. |
| 2002/0107564 A1 | 8/2002 | Cox et al. |
| 2002/0151961 A1 | 10/2002 | Lashinski et al. |
| 2002/0156517 A1 | 10/2002 | Perouse |
| 2002/0177904 A1 | 11/2002 | Huxel et al. |
| 2003/0033003 A1 | 2/2003 | Harrison et al. |
| 2003/0057156 A1 | 3/2003 | Peterson et al. |
| 2003/0083742 A1 | 5/2003 | Spence et al. |
| 2003/0093096 A1 | 5/2003 | McGuckin, Jr. et al. |
| 2003/0105519 A1 * | 6/2003 | Fasol .................. A61F 2/2457 623/2.1 |
| 2003/0167071 A1 | 9/2003 | Martin et al. |
| 2003/0229350 A1 | 12/2003 | Kay |
| 2003/0233142 A1 * | 12/2003 | Morales ............ A61B 17/00234 623/2.37 |
| 2003/0236568 A1 | 12/2003 | Hojeibane et al. |
| 2004/0117009 A1 | 6/2004 | Cali et al. |
| 2004/0133274 A1 | 7/2004 | Webler et al. |
| 2004/0158314 A1 | 8/2004 | Hogendijk |
| 2004/0172046 A1 | 9/2004 | Hlavka et al. |
| 2004/0181287 A1 | 9/2004 | Gellman |
| 2004/0186566 A1 | 9/2004 | Hindrichs et al. |
| 2004/0193092 A1 | 9/2004 | Deal |
| 2004/0236419 A1 | 11/2004 | Milo |
| 2004/0243229 A1 * | 12/2004 | Vidlund ............ A61B 17/00234 623/2.34 |
| 2004/0260389 A1 | 12/2004 | Case et al. |
| 2005/0004668 A1 | 1/2005 | Aklog et al. |
| 2005/0016560 A1 | 1/2005 | Voughlohn |
| 2005/0021085 A1 | 1/2005 | Abrams et al. |
| 2005/0055089 A1 | 3/2005 | Macoviak et al. |
| 2005/0059984 A1 | 3/2005 | Chanduszko et al. |
| 2005/0059997 A1 | 3/2005 | Bauman et al. |
| 2005/0075713 A1 | 4/2005 | Biancucci et al. |
| 2005/0075723 A1 | 4/2005 | Schroeder et al. |
| 2005/0080483 A1 | 4/2005 | Solem et al. |
| 2005/0090827 A1 | 4/2005 | Gedebou |
| 2005/0096666 A1 | 5/2005 | Gordon et al. |
| 2005/0107812 A1 | 5/2005 | Starksen et al. |
| 2005/0107871 A1 | 5/2005 | Realyvasquez et al. |
| 2005/0113900 A1 | 5/2005 | Shiroff et al. |
| 2005/0125077 A1 | 6/2005 | Harmon et al. |
| 2005/0137688 A1 | 6/2005 | Salahieh et al. |
| 2005/0137695 A1 | 6/2005 | Salahieh et al. |
| 2005/0143770 A1 | 6/2005 | Carter et al. |
| 2005/0149182 A1 | 7/2005 | Alferness et al. |
| 2005/0154448 A1 | 7/2005 | Cully et al. |
| 2005/0177180 A1 | 8/2005 | Kaganov et al. |
| 2005/0177224 A1 | 8/2005 | Fogarty et al. |
| 2005/0177228 A1 | 8/2005 | Solem |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222488 A1 | 10/2005 | Chang et al. |
| 2005/0222665 A1 | 10/2005 | Arayani |
| 2005/0228422 A1 | 10/2005 | Machold et al. |
| 2005/0251208 A1 | 11/2005 | Elmer et al. |
| 2005/0256532 A1 | 11/2005 | Nayak et al. |
| 2005/0273138 A1 | 12/2005 | To et al. |
| 2005/0283246 A1 | 12/2005 | Cauthen et al. |
| 2006/0004442 A1 | 1/2006 | Spenser et al. |
| 2006/0020326 A9 | 1/2006 | Bolduc et al. |
| 2006/0020327 A1 | 1/2006 | Lashinski et al. |
| 2006/0052821 A1 | 3/2006 | Abbot et al. |
| 2006/0079736 A1 | 4/2006 | Chin et al. |
| 2006/0106278 A1 | 5/2006 | Machold et al. |
| 2006/0106279 A1 | 5/2006 | Machold et al. |
| 2006/0106420 A1 | 5/2006 | Dolan et al. |
| 2006/0106423 A1 | 5/2006 | Weisel et al. |
| 2006/0129166 A1 | 6/2006 | Lavelle |
| 2006/0161265 A1 | 7/2006 | Levine et al. |
| 2006/0173524 A1 | 8/2006 | Salahieh et al. |
| 2006/0178700 A1 * | 8/2006 | Quinn ............ A61B 17/00234 606/213 |
| 2006/0200199 A1 | 9/2006 | Bonutti et al. |
| 2006/0206201 A1 | 9/2006 | Garcia et al. |
| 2006/0229708 A1 | 10/2006 | Powell et al. |
| 2006/0241745 A1 * | 10/2006 | Solem ................ A61F 2/2418 623/2.18 |
| 2006/0241748 A1 | 10/2006 | Lee et al. |
| 2006/0252984 A1 | 11/2006 | Randert et al. |
| 2006/0259135 A1 | 11/2006 | Navia et al. |
| 2006/0259137 A1 | 11/2006 | Artof et al. |
| 2006/0265042 A1 | 11/2006 | Catanese et al. |
| 2006/0276871 A1 | 12/2006 | Lamson et al. |
| 2006/0282161 A1 | 12/2006 | Huynh et al. |
| 2007/0016287 A1 | 1/2007 | Cartledge |
| 2007/0016288 A1 | 1/2007 | Gurskis |
| 2007/0021781 A1 | 1/2007 | Jervis et al. |
| 2007/0032787 A1 | 2/2007 | Hassett et al. |
| 2007/0032796 A1 | 2/2007 | Chin-Chen et al. |
| 2007/0032820 A1 | 2/2007 | Chin-Chen et al. |
| 2007/0038221 A1 | 2/2007 | Fine et al. |
| 2007/0038296 A1 | 2/2007 | Navia |
| 2007/0049942 A1 | 3/2007 | Hindrichs et al. |
| 2007/0049970 A1 | 3/2007 | Belef et al. |
| 2007/0049971 A1 | 3/2007 | Chin et al. |
| 2007/0051377 A1 | 3/2007 | Douk et al. |
| 2007/0055340 A1 | 3/2007 | Pryor |
| 2007/0060895 A1 | 3/2007 | Sibbitt et al. |
| 2007/0060989 A1 | 3/2007 | Deem et al. |
| 2007/0061010 A1 | 3/2007 | Hauser et al. |
| 2007/0066863 A1 | 3/2007 | Rafiee et al. |
| 2007/0083168 A1 | 4/2007 | Whiting et al. |
| 2007/0093869 A1 | 4/2007 | Bloom et al. |
| 2007/0100427 A1 | 5/2007 | Perouse |
| 2007/0112425 A1 | 5/2007 | Schaller et al. |
| 2007/0118151 A1 | 5/2007 | Davidson |
| 2007/0123936 A1 | 5/2007 | Goldin et al. |
| 2007/0162107 A1 | 7/2007 | Haug et al. |
| 2007/0168013 A1 | 7/2007 | Douglas |
| 2007/0185532 A1 | 8/2007 | Stone et al. |
| 2007/0198082 A1 | 8/2007 | Kapadia et al. |
| 2007/0203391 A1 | 8/2007 | Bloom et al. |
| 2007/0208389 A1 | 9/2007 | Amundson et al. |
| 2007/0219558 A1 | 9/2007 | Deutsch |
| 2007/0250160 A1 | 10/2007 | Rafiee |
| 2007/0265658 A1 | 11/2007 | Nelson et al. |
| 2007/0265700 A1 | 11/2007 | Eliasen et al. |
| 2007/0270943 A1 | 11/2007 | Solem et al. |
| 2007/0276437 A1 | 11/2007 | Call et al. |
| 2007/0276467 A1 | 11/2007 | Kalmann |
| 2007/0282375 A1 | 12/2007 | Hindrichs et al. |
| 2007/0282429 A1 | 12/2007 | Hauser et al. |
| 2007/0288086 A1 | 12/2007 | Kalmann et al. |
| 2007/0288089 A1 | 12/2007 | Gurskis et al. |

(56) References Cited

U.S. PATENT DOCUMENTS

| | | |
|---|---|---|
| 2007/0293943 A1* | 12/2007 | Quinn .................... A61F 2/246 623/2.11 |
| 2008/0003539 A1 | 1/2008 | Lundgren |
| 2008/0015617 A1 | 1/2008 | Harari et al. |
| 2008/0027268 A1 | 1/2008 | Buckner et al. |
| 2008/0027446 A1 | 1/2008 | Stone et al. |
| 2008/0027483 A1 | 1/2008 | Cartledge |
| 2008/0033475 A1 | 2/2008 | Meng |
| 2008/0035160 A1 | 2/2008 | Woodson et al. |
| 2008/0039845 A1 | 2/2008 | Bonutti et al. |
| 2008/0058866 A1 | 3/2008 | Young et al. |
| 2008/0077231 A1 | 3/2008 | Heringes et al. |
| 2008/0091264 A1 | 4/2008 | Machold et al. |
| 2008/0097595 A1 | 4/2008 | Gabbay |
| 2008/0125861 A1 | 5/2008 | Webler et al. |
| 2008/0140116 A1 | 6/2008 | Bonutti |
| 2008/0140188 A1 | 6/2008 | Randert et al. |
| 2008/0167714 A1 | 7/2008 | St. Goar |
| 2008/0190989 A1 | 8/2008 | Crews et al. |
| 2008/0262598 A1 | 10/2008 | Elmaleh |
| 2008/0262609 A1 | 10/2008 | Gross et al. |
| 2008/0275469 A1 | 11/2008 | Fanton et al. |
| 2008/0281411 A1 | 11/2008 | Berreklouw et al. |
| 2008/0288044 A1 | 11/2008 | Osborne |
| 2008/0288062 A1 | 11/2008 | Andrieu et al. |
| 2008/0300629 A1 | 12/2008 | Surti |
| 2009/0005863 A1 | 1/2009 | Goetz et al. |
| 2009/0043381 A1* | 2/2009 | Macoviak ........ A61B 17/00234 623/2.36 |
| 2009/0043382 A1 | 2/2009 | Maurer et al. |
| 2009/0048668 A1 | 2/2009 | Wilson et al. |
| 2009/0082828 A1 | 3/2009 | Ostroff |
| 2009/0082847 A1 | 3/2009 | Zacharias et al. |
| 2009/0084386 A1 | 4/2009 | McClellan et al. |
| 2009/0099647 A1 | 4/2009 | Glimsdale et al. |
| 2009/0099649 A1 | 4/2009 | Chobotov et al. |
| 2009/0112052 A1 | 4/2009 | Lund et al. |
| 2009/0118776 A1 | 5/2009 | Kelsch et al. |
| 2009/0131849 A1 | 5/2009 | Maurer et al. |
| 2009/0132033 A1 | 5/2009 | Maurer et al. |
| 2009/0143808 A1 | 6/2009 | Houser |
| 2009/0149872 A1 | 6/2009 | Gross et al. |
| 2009/0171439 A1 | 7/2009 | Nissl |
| 2009/0216265 A1 | 8/2009 | DeVries |
| 2009/0240326 A1 | 9/2009 | Wilson et al. |
| 2009/0254103 A1 | 10/2009 | Deutsch et al. |
| 2009/0259307 A1 | 10/2009 | Gross et al. |
| 2009/0264991 A1 | 10/2009 | Paul et al. |
| 2009/0264995 A1 | 10/2009 | Subramanian |
| 2009/0276040 A1 | 11/2009 | Rowe et al. |
| 2009/0287304 A1 | 11/2009 | Dahlgren et al. |
| 2009/0306622 A1 | 12/2009 | Machold et al. |
| 2009/0326648 A1 | 12/2009 | Machold et al. |
| 2010/0022948 A1 | 1/2010 | Wilson et al. |
| 2010/0023117 A1 | 1/2010 | Yoganathan et al. |
| 2010/0023118 A1 | 1/2010 | Medlock et al. |
| 2010/0029071 A1 | 2/2010 | Russell et al. |
| 2010/0030329 A1 | 2/2010 | Frater |
| 2010/0049293 A1 | 2/2010 | Zukowski et al. |
| 2010/0063520 A1 | 3/2010 | Bilotti |
| 2010/0063542 A1 | 3/2010 | Van der Burg et al. |
| 2010/0063586 A1* | 3/2010 | Hasenkam ......... A61B 17/0401 623/2.37 |
| 2010/0121349 A1 | 5/2010 | Meier et al. |
| 2010/0121434 A1 | 5/2010 | Paul et al. |
| 2010/0121435 A1 | 5/2010 | Subramanian et al. |
| 2010/0130992 A1 | 5/2010 | Machold et al. |
| 2010/0161041 A1* | 6/2010 | Maisano ............ A61B 17/0401 623/2.1 |
| 2010/0161042 A1 | 6/2010 | Maisano et al. |
| 2010/0161043 A1 | 6/2010 | Maisano et al. |
| 2010/0161047 A1* | 6/2010 | Cabiri ................... A61F 2/2466 623/2.37 |
| 2010/0168791 A1 | 7/2010 | Kassab |
| 2010/0174358 A1 | 7/2010 | Rabkin |
| 2010/0185278 A1 | 7/2010 | Schankereli |
| 2010/0204662 A1 | 8/2010 | Orlov et al. |
| 2010/0211166 A1 | 8/2010 | Miller et al. |
| 2010/0217309 A1 | 8/2010 | Hansen et al. |
| 2010/0217382 A1 | 8/2010 | Chau et al. |
| 2010/0228269 A1 | 9/2010 | Garrison et al. |
| 2010/0234935 A1 | 9/2010 | Bashiri |
| 2010/0249908 A1 | 9/2010 | Chau et al. |
| 2010/0249920 A1 | 9/2010 | Bolling et al. |
| 2010/0256743 A1 | 10/2010 | Hinchliffe et al. |
| 2010/0264192 A1 | 10/2010 | Marczyk |
| 2010/0268204 A1 | 10/2010 | Tieu et al. |
| 2010/0280603 A1 | 11/2010 | Maisano et al. |
| 2010/0280604 A1 | 11/2010 | Zipory et al. |
| 2010/0280605 A1 | 11/2010 | Hammer et al. |
| 2010/0286628 A1 | 11/2010 | Gross |
| 2010/0286767 A1 | 11/2010 | Zipory et al. |
| 2010/0298930 A1 | 11/2010 | Orlov |
| 2010/0324598 A1 | 12/2010 | Anderson |
| 2010/0324668 A1 | 12/2010 | Maurer et al. |
| 2011/0009818 A1 | 1/2011 | Goff |
| 2011/0011917 A1 | 1/2011 | Loulmet |
| 2011/0022164 A1 | 1/2011 | Quinn et al. |
| 2011/0029066 A1 | 2/2011 | Gilad |
| 2011/0029071 A1 | 2/2011 | Zlotnick et al. |
| 2011/0035000 A1 | 2/2011 | Nieminen et al. |
| 2011/0040366 A1 | 2/2011 | Goetz et al. |
| 2011/0060407 A1* | 3/2011 | Ketai ................ A61B 17/00234 623/2.37 |
| 2011/0071626 A1 | 3/2011 | Wright et al. |
| 2011/0077733 A1 | 3/2011 | Solem |
| 2011/0082538 A1 | 4/2011 | Dahlgren et al. |
| 2011/0087146 A1 | 4/2011 | Ryan et al. |
| 2011/0092993 A1 | 4/2011 | Jacobs |
| 2011/0093002 A1 | 4/2011 | Rucker et al. |
| 2011/0098732 A1 | 4/2011 | Jacobs |
| 2011/0106245 A1 | 5/2011 | Miller et al. |
| 2011/0106247 A1 | 5/2011 | Miller et al. |
| 2011/0112619 A1 | 5/2011 | Foster et al. |
| 2011/0112632 A1 | 5/2011 | Chau et al. |
| 2011/0137397 A1 | 6/2011 | Chau et al. |
| 2011/0152998 A1 | 6/2011 | Berez et al. |
| 2011/0166636 A1 | 7/2011 | Rowe |
| 2011/0166649 A1* | 7/2011 | Gross .................... A61F 2/2445 623/2.36 |
| 2011/0184510 A1* | 7/2011 | Maisano ............ A61B 17/0401 623/1.24 |
| 2011/0190879 A1 | 8/2011 | Bobo et al. |
| 2011/0208283 A1 | 8/2011 | Rust et al. |
| 2011/0224785 A1 | 9/2011 | Hacohen |
| 2011/0238088 A1 | 9/2011 | Bolduc et al. |
| 2011/0238112 A1 | 9/2011 | Kim et al. |
| 2011/0251678 A1 | 10/2011 | Eidenschink |
| 2011/0264208 A1 | 10/2011 | Duffy et al. |
| 2011/0288635 A1* | 11/2011 | Miller ................ A61B 17/0401 623/2.1 |
| 2011/0301698 A1 | 12/2011 | Miller et al. |
| 2012/0016343 A1 | 1/2012 | Gill |
| 2012/0022633 A1 | 1/2012 | Olson et al. |
| 2012/0022639 A1 | 1/2012 | Hacohen et al. |
| 2012/0022640 A1 | 1/2012 | Gross et al. |
| 2012/0022644 A1* | 1/2012 | Reich ................... A61B 17/072 623/2.37 |
| 2012/0143320 A1 | 1/2012 | Eliasen et al. |
| 2012/0029628 A1 | 2/2012 | Rowe |
| 2012/0035712 A1 | 2/2012 | Maisano |
| 2012/0083806 A1 | 4/2012 | Goertzen |
| 2012/0123531 A1 | 5/2012 | Tsukashima et al. |
| 2012/0130374 A1 | 5/2012 | Bouduban et al. |
| 2012/0130421 A1 | 5/2012 | Hafez et al. |
| 2012/0158021 A1 | 6/2012 | Morrill |
| 2012/0158053 A1 | 6/2012 | Paulos |
| 2012/0179244 A1 | 7/2012 | Schankereli et al. |
| 2012/0215236 A1 | 8/2012 | Matsunaga et al. |
| 2012/0222969 A1 | 9/2012 | Osborne et al. |
| 2012/0226349 A1 | 9/2012 | Tuval et al. |
| 2012/0232373 A1 | 9/2012 | Hallander et al. |
| 2012/0245604 A1 | 9/2012 | Tegzes |

(56) References Cited

U.S. PATENT DOCUMENTS

| | | |
|---|---|---|
| 2012/0283757 A1 | 11/2012 | Miller et al. |
| 2012/0296349 A1 | 11/2012 | Smith et al. |
| 2012/0310328 A1 | 12/2012 | Olson et al. |
| 2013/0018459 A1 | 1/2013 | Maisano et al. |
| 2013/0030522 A1 | 1/2013 | Rowe et al. |
| 2013/0041459 A1 | 2/2013 | Wilson et al. |
| 2013/0046373 A1 | 2/2013 | Cartledge et al. |
| 2013/0053951 A1 | 2/2013 | Baliarda |
| 2013/0079873 A1 | 3/2013 | Migliazza et al. |
| 2013/0085529 A1 | 4/2013 | Housman |
| 2013/0096664 A1 | 4/2013 | Goetz et al. |
| 2013/0096672 A1 | 4/2013 | Reich et al. |
| 2013/0110230 A1 | 5/2013 | Solem |
| 2013/0166017 A1 | 6/2013 | Cartledge et al. |
| 2013/0166022 A1 | 6/2013 | Conklin |
| 2013/0172978 A1 | 7/2013 | Vidlund et al. |
| 2013/0190863 A1 | 7/2013 | Call et al. |
| 2013/0281760 A1 | 10/2013 | Farnan et al. |
| 2013/0296925 A1 | 11/2013 | Chanduszko et al. |
| 2013/0325110 A1 | 12/2013 | Khalil et al. |
| 2013/0331930 A1 | 12/2013 | Rowe et al. |
| 2014/0005778 A1 | 1/2014 | Buchbinder et al. |
| 2014/0018911 A1 | 1/2014 | Zhou et al. |
| 2014/0031864 A1 | 1/2014 | Jafari et al. |
| 2014/0031928 A1 | 1/2014 | Murphy et al. |
| 2014/0058405 A1 | 2/2014 | Foster |
| 2014/0066693 A1 | 3/2014 | Goldfarb et al. |
| 2014/0067054 A1 | 3/2014 | Chau et al. |
| 2014/0114390 A1 | 4/2014 | Tobis et al. |
| 2014/0121763 A1 | 5/2014 | Duffy et al. |
| 2014/0142689 A1 | 5/2014 | De Canniere et al. |
| 2014/0163690 A1 | 6/2014 | White |
| 2014/0200657 A1 | 7/2014 | Maurer et al. |
| 2014/0207231 A1 | 7/2014 | Hacohen et al. |
| 2014/0214159 A1 | 7/2014 | Vidlund et al. |
| 2014/0243894 A1 | 8/2014 | Groothuis et al. |
| 2014/0257475 A1 | 9/2014 | Gross et al. |
| 2014/0275757 A1 | 9/2014 | Goodwin et al. |
| 2014/0277390 A1 | 9/2014 | Ratz et al. |
| 2014/0277427 A1 | 9/2014 | Ratz et al. |
| 2014/0288639 A1 | 9/2014 | Gainor |
| 2014/0296962 A1 | 10/2014 | Cartledge et al. |
| 2014/0309730 A1 | 10/2014 | Alon et al. |
| 2014/0324164 A1 | 10/2014 | Gross et al. |
| 2014/0358224 A1 | 12/2014 | Tegels et al. |
| 2014/0371843 A1 | 12/2014 | Wilson et al. |
| 2014/0379006 A1 | 12/2014 | Sutherland et al. |
| 2014/0379074 A1 | 12/2014 | Spence et al. |
| 2014/0379076 A1 | 12/2014 | Vidlund et al. |
| 2015/0018940 A1 | 1/2015 | Quill et al. |
| 2015/0045879 A1 | 2/2015 | Longoria et al. |
| 2015/0051698 A1 | 2/2015 | Baliarda et al. |
| 2015/0066082 A1 | 3/2015 | Moshe et al. |
| 2015/0066138 A1 | 3/2015 | Alexander et al. |
| 2015/0073545 A1 | 3/2015 | Braido |
| 2015/0094800 A1 | 4/2015 | Chawla |
| 2015/0094802 A1 | 4/2015 | Buchbinder et al. |
| 2015/0100116 A1 | 4/2015 | Mohl et al. |
| 2015/0119936 A1 | 4/2015 | Gilmore et al. |
| 2015/0127097 A1 | 5/2015 | Neumann et al. |
| 2015/0142049 A1 | 5/2015 | Delgado et al. |
| 2015/0142103 A1 | 5/2015 | Vidlund |
| 2015/0142105 A1 | 5/2015 | Bolling et al. |
| 2015/0157329 A1 | 6/2015 | Rudakov et al. |
| 2015/0182336 A1 | 7/2015 | Zipory et al. |
| 2015/0196693 A1 | 7/2015 | Lin |
| 2015/0223934 A1 | 8/2015 | Vidlund et al. |
| 2015/0250590 A1 | 9/2015 | Gries et al. |
| 2015/0272730 A1 | 10/2015 | Melnick et al. |
| 2015/0320414 A1 | 11/2015 | Conklin et al. |
| 2015/0351909 A1 | 12/2015 | Bobo et al. |
| 2015/0366666 A1 | 12/2015 | Khairkhahan et al. |
| 2016/0022417 A1 | 1/2016 | Karapetian et al. |
| 2016/0022422 A1 | 1/2016 | Annest et al. |
| 2016/0038285 A1 | 2/2016 | Glenn et al. |
| 2016/0081829 A1 | 3/2016 | Rowe |
| 2016/0120672 A1 | 5/2016 | Martin et al. |
| 2016/0128689 A1 | 5/2016 | Sutherland et al. |
| 2016/0157862 A1 | 6/2016 | Hernandez et al. |
| 2016/0174979 A1 | 6/2016 | Wei |
| 2016/0228246 A1 | 8/2016 | Zimmerman |
| 2016/0228252 A1 | 8/2016 | Keidar |
| 2016/0235526 A1 | 8/2016 | Lashinski et al. |
| 2016/0242762 A1 | 8/2016 | Gilmore et al. |
| 2016/0256269 A1 | 9/2016 | Cahalane et al. |
| 2016/0262741 A1 | 9/2016 | Gilmore et al. |
| 2016/0270776 A1 | 9/2016 | Miraki et al. |
| 2016/0270916 A1 | 9/2016 | Cahalane et al. |
| 2016/0287383 A1 | 10/2016 | Rowe |
| 2016/0287387 A1 | 10/2016 | Wei |
| 2017/0056174 A1* | 3/2017 | Tobis ............... A61B 17/06166 |
| 2018/0071097 A1* | 3/2018 | Alon ............... A61F 2/2466 |

FOREIGN PATENT DOCUMENTS

| | | |
|---|---|---|
| EP | 1759663 | 3/2007 |
| EP | 1 836 971 | 9/2007 |
| EP | 1 968 491 | 7/2010 |
| EP | 2399549 | 3/2014 |
| WO | 1992/005093 | 4/1992 |
| WO | 1997/041778 | 11/1997 |
| WO | 2000/28923 | 5/2000 |
| WO | 2001/010306 | 2/2001 |
| WO | 2002/062236 | 8/2002 |
| WO | 2003/000331 | 1/2003 |
| WO | 2004/030569 | 4/2004 |
| WO | 2004/069055 | 8/2004 |
| WO | 2004/082538 | 9/2004 |
| WO | 2004/112585 | 12/2004 |
| WO | 2005/018507 | 3/2005 |
| WO | 2005/021063 | 3/2005 |
| WO | 2005/058206 | 6/2005 |
| WO | 2005/082288 | 9/2005 |
| WO | 2005/102194 | 11/2005 |
| WO | 2006/019498 | 2/2006 |
| WO | 2006/034062 | 3/2006 |
| WO | 2006/097931 | 9/2006 |
| WO | 2006/105008 | 10/2006 |
| WO | 2006/105009 | 10/2006 |
| WO | 2007/038786 | 4/2007 |
| WO | 2007/080595 | 7/2007 |
| WO | 2007/135101 | 11/2007 |
| WO | 2007/140309 | 12/2007 |
| WO | 2008/065044 | 6/2008 |
| WO | 2008/068756 | 6/2008 |
| WO | 2009/039400 | 3/2009 |
| WO | 2009/101617 | 8/2009 |
| WO | 2010/004546 | 1/2010 |
| WO | 2010/008549 | 1/2010 |
| WO | 2010/071494 | 6/2010 |
| WO | 2010/073246 | 7/2010 |
| WO | 2010/099032 | 9/2010 |
| WO | 2010/108079 | 9/2010 |
| WO | 2010/128502 | 11/2010 |
| WO | 2010/128503 | 11/2010 |
| WO | 2011/014496 | 2/2011 |
| WO | 2011/034973 | 3/2011 |
| WO | 2011/037891 | 3/2011 |
| WO | 2011/051942 | 5/2011 |
| WO | 2011/089601 | 7/2011 |
| WO | 2011/097355 | 8/2011 |
| WO | 2011/143263 | 11/2011 |
| WO | 2011/153408 | 12/2011 |
| WO | 2012/127309 | 9/2012 |
| WO | 2013/003228 | 1/2013 |
| WO | 2013/011502 | 1/2013 |
| WO | 2013/028145 | 2/2013 |
| WO | 2013/078497 | 6/2013 |
| WO | 2013/179295 | 12/2013 |
| WO | 2014/043527 | 3/2014 |
| WO | 2014/064694 | 5/2014 |
| WO | 2014/087402 | 6/2014 |
| WO | 2014/108903 | 7/2014 |
| WO | 2014/141239 | 9/2014 |

(56) References Cited

FOREIGN PATENT DOCUMENTS

| WO | 2015/015497 | 2/2015 |
|----|-------------|--------|
| WO | 2015/063580 | 5/2015 |
| WO | 2015/193728 | 12/2015 |
| WO | 2016/011275 | 1/2016 |
| WO | 2016/087934 | 6/2016 |
| WO | 2016/189391 | 12/2016 |

OTHER PUBLICATIONS

An Interview Summary dated Oct. 24, 2012, which issued during the prosecution of U.S. Appl. No. 12/692,061.
Alfieri et al., "An effective technique to correct anterior mitral leaflet prolapse," J Card Surg 14(6):468-470 (1999).
An Interview Summary dated Dec. 5, 2016, which issued during the prosecution of U.S. Appl. No. 13/574,088.
Alfieri et al., "Novel suture device for beating heart mitral leaflet approximation," Annals of Thoracic Surgery 74:1488 1493 (2002).
Alfieri et al., "The double orifice technique in mitral valve repair: a simple solution for complex problems," Journal of Thoracic Cardiovascular Surgery 122:674-681 (2001).
Amplatzer Cardiac Plug Brochure (English Pages), AGA Medical Corporation, Plymouth, MN Copyright 2008-2011, downloaded Jan. 11, 2011.
Beale BS, "Surgical Repair of Collateral Ligament Injuries," presented at 63rd CVMA Convention, Halifax, Nova Scotia, Canada, Jul. 6-9, 2011.
Dentistry Today, "Implant Direct" product information page, Jun. 1, 2011, downloaded Dec. 10, 2012 from http://dentistrytoday.com/top25implant-i/5558-implant-direct.
Maisano et al., "The double-orifice technique as a standardized approach to treat mitral regurgitation due to severe myxomatous disease: surgical technique," European Journal of Cardio-thoracic Surgery 17 (2000) 201-205.
Shikhar Agarwal et al., "Interventional Cardiology Perspective of Functional Tricuspid Regurgitation," Circulatoin: Cardiovascular Interventions, pp. 565-573; Dec. 2009; vol. 2, Issue 6.
Smith & Nephew Minitac™ TI 2.0 Suture Anchor Product Description, downloaded on Dec. 9, 2012 from http://global.smith-nephew.com/us/MINITAC_TI_2_SUTURE_ANCHR_3127.htm.
Second Notice of Allowance dated May 10, 2013, which issued during the prosecution of U.S. Appl. No. 12/692,061.
An Office Action dated Mar. 23, 2017, which issued during the prosecution of U.S. Appl. No. 13/574,088.
An Office Action dated Jul. 6, 2012, which issued during the prosecution of U.S. Appl. No. 12/692,061.
A Notice of Allowance dated Mar. 6, 2013, which issued during the prosecution of U.S. Appl. No. 12/692,061.
An International Search Report and a Written Opinion both dated May 19, 2011, which issued during the prosecution of Applicant's PCT/IL11/00064.
An International Search Report and a Written Opinion both dated Jan. 22, 2013, which issued during the prosecution of Applicant's PCT/IL2012/000282.
An Office Action dated Dec 5, 2013, which issued during the prosecution of U.S. Appl. No. 13/485,145.
An International Search Report and a Written Opinion both dated Mar. 17, 2014, which issued during the prosecution of Applicant's PCT/IL2013/050937.
Invitation to pay additional fees in PCT/IL2014/050027 dated Apr. 4, 2014.
An International Search Report and a Written Opinion both dated May 28, 2014, which issued during the prosecution of Applicant's PCT/IL2014/050027.
U.S. Appl. No. 60/902,146, filed Feb. 16, 2007.
European Search Report dated Apr. 10, 2015, which issued during the prosecution of Applicant's European App No. 11734451.5.
European Search Report dated May 15, 2015, which issued during the prosecution of Applicant's European App No. 12814417.7.
An Office Action dated Sep. 14, 2015, which issued during the prosecution of U.S. Appl. No. 13/553,081.
An English Translation of an Office Action dated Jun. 30, 2015 which issued during the prosecution of Chinese Patent Application No. 201180015301.6.
An English Translation of an Office Action dated Jul. 7, 2015 which issued during the prosecution of Japanese Patent Application No. 2012-549463.
An Office Action dated Oct. 7, 2015, which issued during the prosecution of U.S. Appl. No. 13/574,088.
Invitation to Pay Additional Fees dated Apr. 20, 2015, which issued during the prosecution of Applicant's PCT/IB2014/002351.
An International Search Report and a Written Opinion both dated Jun. 10, 2015, which issued during the prosecution of Applicant's PCT/IB2014/002351.
An Office Action dated Feb. 2, 2015, which issued during the prosecution of U.S. Appl. No. 14/143,355.
An English Translation of an Office Action dated Feb. 10, 2015 which issued during the prosecution of Chinese Patent Application No. 201180015301.6.
An Office Action dated Feb. 25, 2015, which issued during the prosecution of U.S. Appl. No. 13/574,088.
Notice of Allowance dated Sep. 24, 2015, which issued during the prosecution of U.S. Appl. No. 14/143,355.
Notice of Allowance dated Dec. 4, 2015, which issued during the prosecution of U.S. Appl. No. 14/143,355.
An Office Action dated Jul. 7, 2014, which issued during the prosecution of U.S. Appl. No. 13/485,145.
An English Translation of an Office Action dated Jun. 30, 2014 which issued during the prosecution of Chinese Patent Application No. 201180015301.6.
An Office Action dated Sep. 25, 2014, which issued during the prosecution of U.S. Appl. No. 13/485,145.
An English Translation of an Office Action dated Oct. 28, 2014,which issued during the prosecution of Japanese Patent Application No. 2012-549463.
Notice of Allowance dated Dec. 9, 2014, which issued during the prosecution of U.S. Appl. No. 13/485,145.
An International Search Report and a Written Opinion both dated Jun. 30, 2014, which issued during the prosecution of Applicant's PCT/IL2014/050233.
An International Search Report and a Written Opinion both dated Jan. 8, 2016, 2014, which issued during the prosecution of Applicant's PCT/IB2015/001196.
Invitation to pay additional fees in PCT/IB2015/001196 dated Oct. 26, 2015.
Notice of Allowance dated Dec. 4, 2014, which issued during the prosecution of U.S. Appl. No. 13/188,175.
An Office Action dated Nov. 25, 2014, which issued during the prosecution of U.S. Appl. No. 13/553,081.
An Office Action dated Apr. 18, 2016, which issued during the prosecution of U.S. Appl. No. 14/584,286.
Spinal & Epidural Needles—downloaded on Feb. 18, 2016 from http://www.cothon.net/Anestesia_Obstetrica/Neuroaxial_needles.html.
An Office Action dated May 11, 2016, which issued during the prosecution of U.S. Appl. No. 13/574,088.
An International Search Report and a Written Opinion both dated Apr. 15, 2016, 2014, which issued during the prosecution of Applicant's PCT/IB2015/002354.
An Office Action dated Jan. 19, 2017, which issued during the prosecution of Chinese Patent Application No. 2014800131345.
An English Translation of an Office Action dated Jun. 23, 2016 which issued during the prosecution of Chinese Patent Application No. 201480028044.3. (the relevant part only).
An International Search Report and a Written Opinion both dated Dec. 8, 2016, which issued during the prosecution of Applicant's PCT/IB2016/000840.
Notice of Allowance dated Sep. 5, 2016, which issued during the prosecution of Chinese Patent Application No. 2014800280443.
An Office Action dated Sep. 14, 2016, which issued during the prosecution of U.S. Appl. No. 13/574,088.

(56) References Cited

OTHER PUBLICATIONS

Invitation to pay additional fees in PCT/IB2016/000840 dated Oct. 13, 2016.
An Office Action dated Jan. 12, 2017, which issued during the prosecution of U.S. Appl. No. 15/264,250.
An Office Action dated Apr. 6, 2017, which issued during the prosecution of U.S. Appl. No. 14/759,768.
An Office Action dated Feb. 21, 2017, which issued during the prosecution of Japanese Patent Application No. 2016-097937.
An Office Action dated Jun. 19, 2017, which issued during the prosecution of U.S. Appl. No. 15/123,157.
Kay, et al., Surgucal Treatment of Tricuspid Insufficiency, Ann. Surg. 162(1): 53-58 (1965).

* cited by examiner

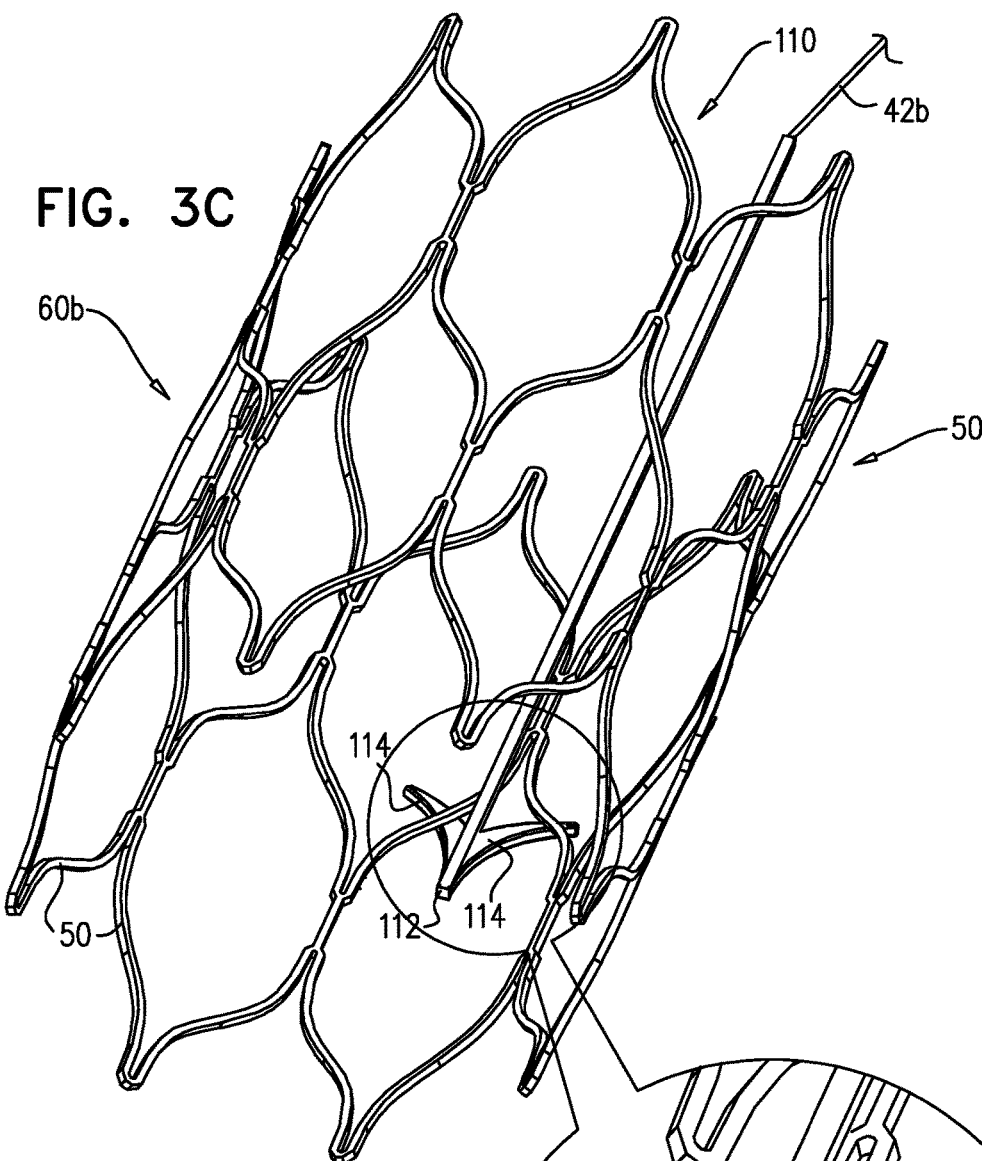
FIG. 3C
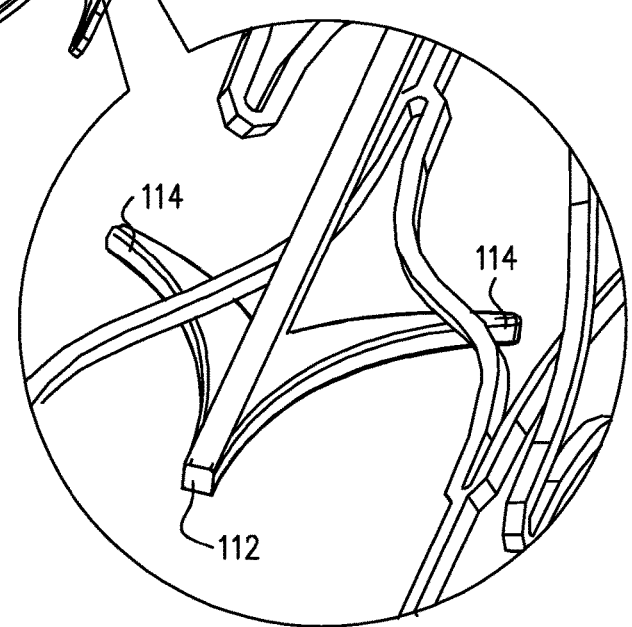

SECTION A-A

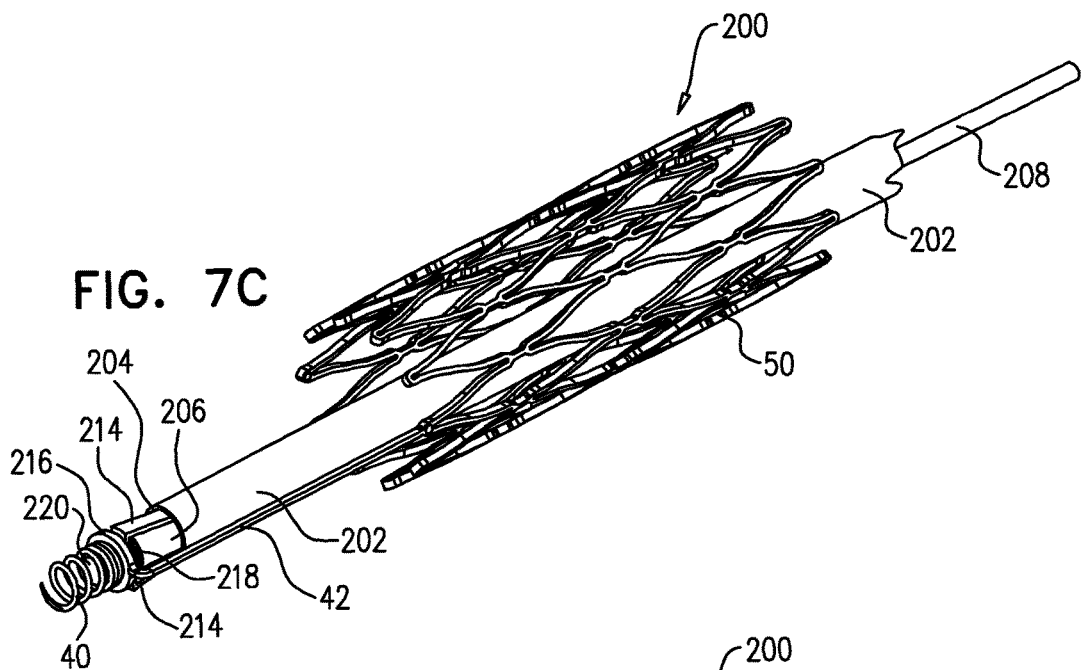
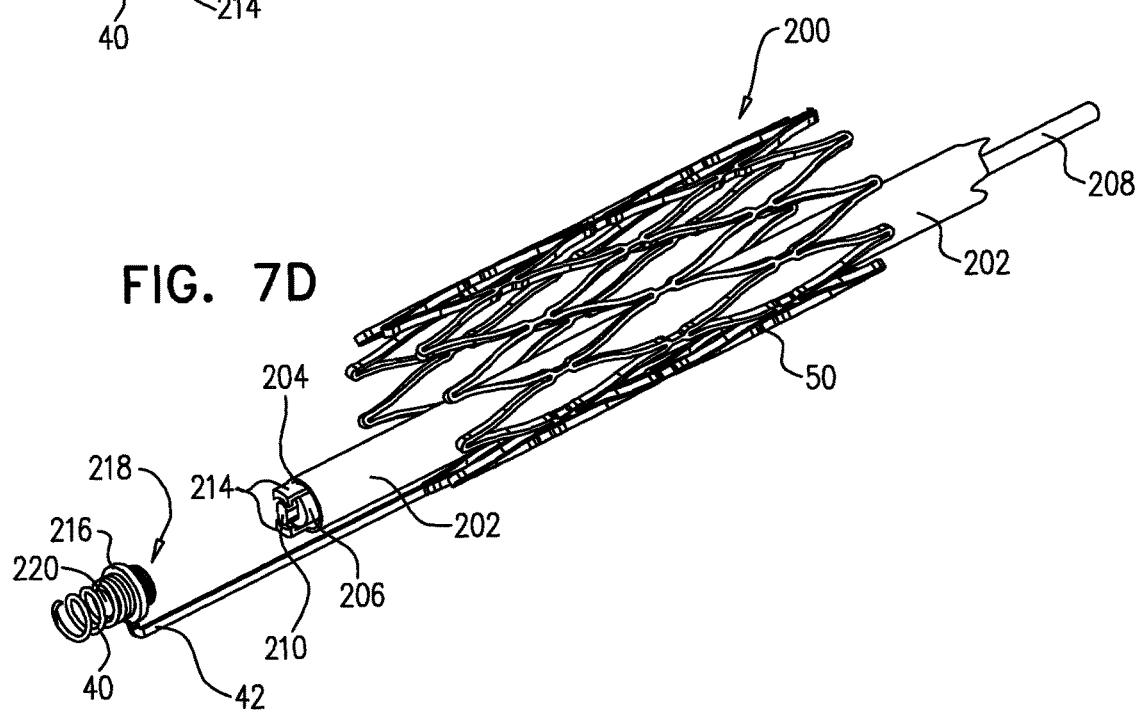

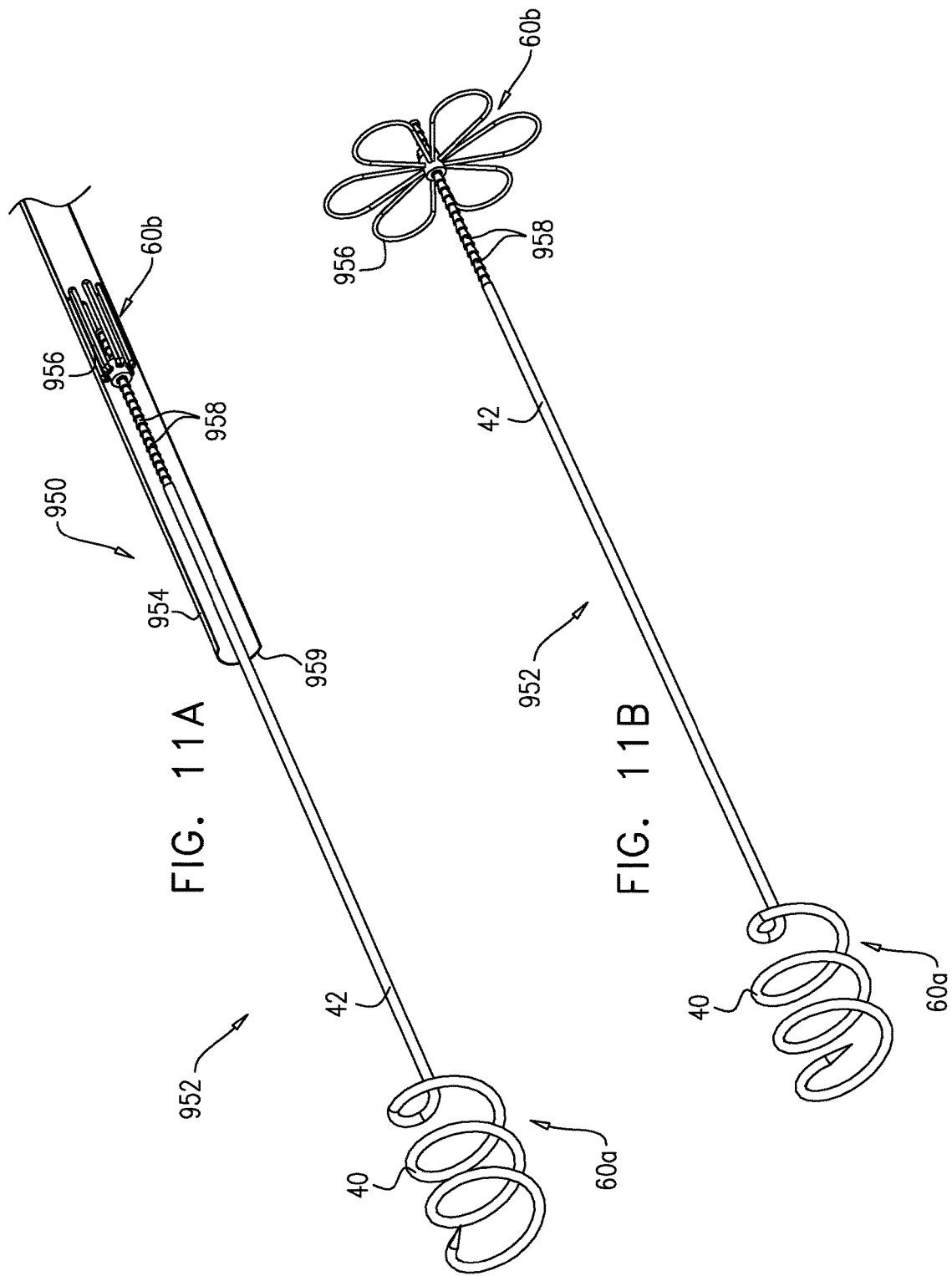

TRICUSPID VALVE REPAIR USING TENSION

CROSS-REFERENCE TO RELATED APPLICATIONS

The present application is a continuation of U.S. application Ser. No. 13/574,088, filed Oct. 19, 2012, now abandoned, which is the U.S. national stage of International Application PCT/IL2011/000064, filed Jan. 20, 2011, which claims priority from and is a continuation-in-part of U.S. application Ser. No 12/692,061, filed Jan. 22, 2010, entitled, "Tricuspid valve repair using tension," now U.S. Pat. No. 8,475,525, which is assigned to the assignee of the present application and is incorporated herein by reference.

FIELD OF THE APPLICATION

Some applications of the present invention relate in general to valve repair. More specifically, some applications of the present invention relate to repair of a tricuspid valve of a patient.

BACKGROUND OF THE APPLICATION

Functional tricuspid regurgitation (FTR) is governed by several pathophysiologic abnormalities such as tricuspid valve annular dilatation, annular shape, pulmonary hypertension, left or right ventricle dysfunction, right ventricle geometry, and leaflet tethering. Treatment options for FTR are primarily surgical. The current prevalence of moderate-to-severe tricuspid regurgitation is estimated to be 1.6 million in the United States. Of these, only 8,000 patients undergo tricuspid valve surgeries annually, most of them in conjunction with left heart valve surgeries.

SUMMARY OF THE INVENTION

In some applications of the present invention, apparatus and methods are provided for repairing a tricuspid valve of a patient using tension. Typically, the apparatus and methods for repairing the tricuspid valve facilitate reducing of tricuspid valve regurgitation by altering the geometry of the tricuspid valve and/or by altering the geometry of the wall of the right atrium of the heart of the patient. In some applications of the present invention, a first tissue-engaging element is implanted in a first portion of tissue that is upstream of the tricuspid valve of the patient. A second tissue-engaging element is then implanted in a second portion of tissue that is upstream of the tricuspid valve of the patient. Typically, following implantation of both the first and second tissue-engaging elements, a distance between the leaflets of the tricuspid valve is adjusted by pulling a longitudinal member that connects the first and second tissue-engaging elements or by pulling at least one of the tissue-engaging elements. Alternatively or additionally, the longitudinal member is adjusted prior to implanting the second tissue-engaging element. For some applications, the longitudinal member is coupled at least in part to an adjusting mechanism, and the longitudinal member is pulled or relaxed responsively to actuation of the adjusting mechanism.

In some applications of the present invention, apparatus and method are provided to achieve bicuspidization of the tricuspid valve. For such applications, typically, the anterior leaflet and the septal leaflet are drawn together to enhance coaptation.

For some applications, the first tissue-engaging element comprises a first stent which is expanded in a portion of an inferior vena cava. The second tissue engaging element comprises a second stent which is expanded in a portion of a superior vena cava. The distance between the first and second stents is then adjusted by pulling the longitudinal member, optionally while monitoring regurgitation of the tricuspid valve. Responsively to the pulling of the longitudinal element, the geometry of the right atrium is altered, thereby drawing together the leaflets of the tricuspid valve.

For other applications, the first tissue-engaging element comprises a stent that is implanted in either the inferior or superior vena cava, and the second tissue-engaging element comprises a tissue anchor which punctures a portion of cardiac tissue of the patient and is implanted at least in part in the portion of cardiac tissue. For some applications, a plurality of second tissue-engaging elements are provided (such as two or three), which are implanted in respective portions of cardiac tissue in a vicinity of the heart valve. For some applications, a longitudinal member is (a) directly coupled to the first tissue-engaging element, (b) directly coupled to one of the second tissue-engaging elements, and (c) indirectly coupled to two others of the second tissue-engaging elements by a longitudinal sub-member.

For still other applications of the present invention, both the first and second tissue-engaging elements comprise respective first and second tissue anchors. Each tissue anchor punctures a respective portion of cardiac tissue of the patient and is implanted at least in part in the respective portion of cardiac tissue. The tensioning element couples the first and second tissue anchors and is adjusted following implantation of the first and second tissue anchors by pulling or relaxing the tensioning element.

For some applications of the present invention, a rotation tool is provided for rotating a tissue anchor, so as to drive the anchor into tissue. The rotation tool comprises a rotation tube, a distal end of which is configured to removably engage a proximal coupling head of the anchor, such that rotation of the rotation tube rotates the anchor. For some applications, the tool further comprises an elongated coupling element, which may comprise, for example, a string, a cable, or a wire. The anchor, such as the proximal coupling head thereof, is shaped so as to define a passage therethrough. The elongated coupling element is initially disposed so as to pass through the passage, such that both ends of the elongated coupling element extend in a proximal direction. When thus positioned, the elongated coupling element couples the tool to the anchor. To decouple the tool from the anchor, one of the ends of the elongated coupling element is pulled until the elongated coupling element no longer passes through the passage.

For some applications of the present invention, a system for repairing a tricuspid valve comprises a tensioning device and a deployment tube. The tensioning device comprises a tissue anchor, a radially-expandable anchor, and at least one flexible longitudinal member that connects the tissue and radially-expandable anchors. The radially-expandable anchor, when in a radially-expanded state, is configured to rest against a wall of a cardiac chamber and to not pass through a hole in the cardiac wall. For example, when in its radially-expanded state, the radially-expandable anchor may be shaped like a flower or butterfly, and thus may be shaped so as to define a plurality of petals or wings. Typically, the radially-expandable anchor is configured to generally fall within exactly one plane when in its radially-expanded state.

The radially-expandable anchor defines an opening, through which the longitudinal member passes, such that the radially-expanded anchor is slidably coupled to the longitudinal member. The radially-expandable anchor and the longitudinal member are configured such that the radially-expandable member is lockable to the longitudinal member, so as to prevent movement of the radially-expandable anchor with respect to the longitudinal member at least in a proximal direction toward the proximal end of the longitudinal member. For example, at least a portion of the longitudinal member may be shaped so as to define ratchet teeth, which engage the radially-expandable anchor, thereby preventing the movement of the radially-expandable anchor with respect to the longitudinal member in the proximal direction. Alternatively or additionally, the radially-expandable anchor may be configured to be crimped to the longitudinal member, so as to prevent the movement of the radially-expandable anchor with respect to the longitudinal member.

During a tricuspid valve repair procedure, the deployment tube is advanced into the left atrium. A hole is made in the interatrial septum. The deployment tube is advanced from the left atrium through the hole, until a distal end of the deployment tube is positioned within the right atrium. The tissue anchor is deployed from the distal end of the deployment tube, and anchored to a portion of cardiac tissue in a vicinity of the tricuspid valve. The deployment tube is withdrawn into the left atrium, thereby releasing the radially-expandable anchor in the left atrium near the septum. The longitudinal member is pulled in a proximal direction, while holding the radially-expandable anchor against a left-atrial side of the septum. The radially-expandable anchor is locked to the longitudinal member, so as to prevent movement of the radially-expandable anchor with respect to the longitudinal member at least in the proximal direction. Responsively, a distance between the leaflets of the tricuspid valve is adjusted to reduce and eliminate regurgitation through the valve, and thereby, the valve is repaired. For some applications, a level of regurgitation of the tricuspid valve is monitored in conjunction with pulling the longitudinal member to adjust the distance between the anchors.

For some applications, the stents described hereinabove comprise a plurality of interconnected superelastic metallic struts. Alternatively or additionally, for some applications, one or more of the stents may comprises one or more elongated members and two or more rings. The rings are typically coupled together by the one or more elongated members and by no other elements of the stent. Typically, the rings define respective planes that are generally perpendicular to the elongated members when the stent is in its expanded state. The longitudinal member connects the stent to the tissue anchor(s).

For some applications, at least one of the tissue anchors described hereinabove is configured to radially contract and expand in a manner generally similar to that of an umbrella. The anchor is inserted into the tissue in a radially-contracted state, and is transitioned to a radially-expanded state in order to fix the anchor within the tissue. The anchor comprises a distal tissue-piercing tip, which is fixed at a distal end of a post. The anchor further comprises a plurality of ribs, which are coupled to the anchor near the distal tip, such that the ribs can articulate with the post. The anchor further comprises a runner, which is slidably coupled to the post, such that the runner can slide along the post. A plurality of stretchers are coupled to the runner and respective ones of the ribs, such that the stretchers can articulate with the runner and the respective ribs.

There is therefore provided, in accordance with some applications of the present invention, a method, including:

implanting at least a first tissue-engaging element in a first portion of tissue in a vicinity of a heart valve of a patient;

implanting at least a second tissue-engaging element in a portion of a blood vessel that is in contact with an atrium of a heart of the patient; and drawing at least a first leaflet of the valve toward at least a second leaflet of the valve by adjusting a distance between the portion of the blood vessel and the first portion of tissue in the vicinity of the heart valve of the patient.

In some applications of the present invention, adjusting the distance between the portion of the blood vessel and the first portion of tissue in the vicinity of the heart valve of the patient includes pulling a longitudinal member that connects the first and second tissue-engaging elements.

In some applications of the present invention, implanting the first tissue-engaging element includes implanting the first tissue-engaging element in the first portion of tissue of an annulus of the valve, and the method further includes: implanting, in a second portion of tissue of the annulus, a third tissue-engaging element that is connected to a fourth tissue-engaging element by a longitudinal sub-member; and implanting, in a third portion of tissue of the annulus, the fourth tissue-engaging element such that the longitudinal sub-member engages the longitudinal member at a junction therebetween.

In some applications of the present invention, adjusting the distance between the portion of the blood vessel and the first portion of tissue in the vicinity of the heart valve of the patient includes applying tension to one or more elements selected from the group consisting of the first tissue-engaging element and the second tissue-engaging element.

In some applications of the present invention, the method includes monitoring a level of regurgitation of the heart valve in conjunction with the adjusting the distance between the portion of the blood vessel and the first portion of tissue in the vicinity of the heart valve of the patient.

In some applications of the present invention, adjusting the distance between the portion of the blood vessel and the first portion of tissue in the vicinity of the heart valve of the patient includes pulling the first tissue-engaging element toward the portion of the blood vessel.

In some applications of the present invention, the heart valve includes a tricuspid valve, and adjusting the distance between the portion of the blood vessel and the first portion of tissue in the vicinity of the heart valve of the patient includes achieving bicuspidization of the tricuspid valve of the heart.

In some applications of the present invention, adjusting the distance between the portion of the blood vessel and the first portion of tissue in the vicinity of the heart valve of the patient includes actuating an adjusting mechanism that is coupled to a portion of a longitudinal member that connects the first and second tissue-engaging elements.

In some applications of the present invention, implanting the second tissue-engaging element in the portion of the blood vessel includes expanding a stent in the portion of the blood vessel.

In some applications of the present invention, the stent includes two or more rings coupled together by one or more elongated members and by no other elements of the stent, and implanting the second tissue-engaging element includes expanding the rings such that the rings anchor the stent to a wall of the blood vessel.

In some applications of the present invention, the method includes:

implanting a third tissue-engaging element in a second portion of tissue of the heart, the third tissue-engaging element being connected at a proximal end thereof to a distal end of a longitudinal member; and engaging a proximal end portion of the longitudinal member with the stent.

In some applications of the present invention, the method includes applying tension to the third tissue-engaging element.

In some applications of the present invention, the blood vessel is selected from the group of blood vessels consisting of: a superior vena cava, and an inferior vena cava.

In some applications of the present invention, implanting the first tissue-engaging element in the first portion of tissue in the vicinity of the heart valve of the patient includes engaging the first portion of tissue by performing one or more actions selected from the group consisting of: puncturing and squeezing the first portion of tissue and advancing at least a portion of the first tissue-engaging element into the first portion of tissue.

In some applications of the present invention:

the first portion of tissue in the vicinity of the heart valve includes a portion of tissue of that is opposite the portion of the blood vessel of the patient, engaging the first portion of tissue includes engaging the portion of tissue that is opposite the portion of the blood vessel of the patient, and drawing the first leaflet of the valve toward the second leaflet of the valve includes adjusting a distance between the portion of the blood vessel of the patient and the portion of tissue that is opposite the portion of the blood vessel of the patient.

In some applications of the present invention, the first portion of tissue in the vicinity of the heart valve includes a portion of tissue of an annulus of the valve, and engaging the first portion of tissue includes engaging the portion of tissue of the annulus of the valve.

In some applications of the present invention, the portion of tissue of the annulus of the valve includes a portion of tissue that is between a middle portion of an anterior leaflet of the valve and a middle portion of a posterior leaflet of the valve.

In some applications of the present invention, the first portion of tissue in the vicinity of the heart valve includes a portion of tissue of a wall of the atrium of the heart above an annulus of the valve, and engaging the first portion of tissue includes engaging the portion of tissue of the wall of the atrium.

There is additionally provided, in accordance with some applications of the present invention, a method, including:

implanting at least a first tissue-engaging element in a first portion of tissue upstream of a tricuspid valve of a patient;

implanting at least a second tissue-engaging element in a second portion of tissue upstream of the tricuspid valve of the patient; and altering a geometry of a wall of a right atrium of a heart of the patient by adjusting a distance between the first portion of tissue upstream of the tricuspid valve of the patient and the second portion of tissue upstream of the tricuspid valve of the patient.

In some applications of the present invention, the method further includes implanting at least a third tissue-engaging element in a third portion of tissue upstream of the tricuspid valve of the patient, and altering the geometry of the wall of the right atrium includes altering the geometry of the wall by adjusting respective distances between the first, the second, and the third portions of tissue upstream of the tricuspid valve.

In some applications of the present invention, adjusting the distance between the first portion of tissue upstream of the tricuspid valve of the patient and the second portion of tissue upstream of the tricuspid valve of the patient includes adjusting a distance between the first tissue-engaging element and the second tissue-engaging element.

In some applications of the present invention, the first portion of tissue includes a first portion of the wall of the right atrium, and implanting the first tissue-engaging element in the first portion of tissue upstream of the tricuspid valve of the patient includes implanting the first tissue-engaging element in the first portion of the wall of the right atrium.

In some applications of the present invention, the second portion of tissue includes a second portion of the wall of the right atrium, and implanting the second tissue-engaging element in the second portion of tissue upstream of the tricuspid valve of the patient includes implanting the second tissue-engaging element in the second portion of the wall of the right atrium.

In some applications of the present invention, the method further includes implanting at least a third tissue-engaging element in a third portion of the wall of the right atrium, and altering the geometry of the wall of the right atrium includes altering the geometry of the wall by adjusting respective distances between the first, the second, and the third portions of the wall of the right atrium.

In some applications of the present invention, the method includes monitoring a level of regurgitation of the tricuspid valve in conjunction with the altering the geometry of the wall of the right atrium.

In some applications of the present invention, adjusting the distance between the first portion of tissue upstream of the tricuspid valve of the patient and the second portion of tissue upstream of the tricuspid valve of the patient includes pulling a longitudinal element that connects the first and second tissue-engaging elements.

In some applications of the present invention, adjusting the distance between the first portion of tissue upstream of the tricuspid valve of the patient and the second portion of tissue upstream of the tricuspid valve of the patient includes actuating an adjusting mechanism that is coupled to a portion of a longitudinal element that connects the first and second tissue-engaging elements.

In some applications of the present invention, altering the geometry of the wall of the right atrium of the heart of the patient includes drawing together at least a first leaflet of the tricuspid valve of the patient and at least a second leaflet of the tricuspid valve of the patient.

In some applications of the present invention, implanting the first tissue-engaging element includes implanting the first tissue-engaging element with a longitudinal member coupled to the first tissue-engaging element, the second tissue-engaging element is shaped so as to define a passage, and implanting the second tissue-engaging element includes implanting the second tissue-engaging element with the longitudinal member passing through the passage, and adjusting the distance includes pulling the longitudinal member in a proximal direction, so as to approximate the first and second tissue-engaging element.

In some applications of the present invention, pulling the longitudinal member including pulling the longitudinal member until the first and second tissue-engaging elements become coupled together.

There is further provided, in accordance with some applications of the present invention, a method, including:

engaging at least a portion of at least a first tissue-engaging element in a portion of tissue of a wall of an inferior vena cava of a patient;

engaging at least a portion of at least a second tissue-engaging element in a portion of tissue of a wall of a superior vena cava of the patient;

drawing at least a first leaflet of a heart valve toward at least a second leaflet of the valve by applying tension to one or more portions of tissue selected from the group consisting of: the portion of tissue of the wall of the inferior vena cava of the patient and the portion of tissue of the wall of the superior vena cava of the patient; and monitoring a level of regurgitation of a heart valve of the patient in conjunction with the applying of the tension.

In some applications of the present invention, applying the tension includes applying the tension following the engaging of the at least first tissue-engaging element and the engaging of the at least second tissue-engaging element.

In some applications of the present invention, applying the tension includes adjusting a distance between the portion of tissue of the wall of the inferior vena cava of the patient and the portion of tissue of the wall of the superior vena cava of the patient.

In some applications of the present invention, adjusting the distance between the portion of tissue of the wall of the inferior vena cava of the patient and the portion of tissue of the wall of the superior vena cava of the patient includes, by the applying of the tension, adjusting a distance between the first tissue-engaging element and the second tissue-engaging element.

In some applications of the present invention, engaging the portion of the at least first tissue-engaging element in the portion of tissue of the wall of the inferior vena cava of the patient includes expanding a first stent in the inferior vena cava and contacting at least a portion of the first stent with the portion of the wall of the inferior vena cava.

In some applications of the present invention, engaging the portion of the at least second tissue-engaging element in the portion of tissue of the wall of the superior vena cava of the patient includes expanding a second stent in the interior vena cava and contacting at least a portion of the first stent with the portion of the wall of the inferior vena cava.

In some applications of the present invention, applying the tension includes altering a geometry of a wall of an atrium of a heart of the patient.

In some applications of the present invention, applying the tension includes pulling a longitudinal member that connects the at least first tissue-engaging element and the at least second tissue-engaging element.

In some applications of the present invention, applying the tension includes actuating an adjusting mechanism that is coupled to a portion of a tensioning element that connects the first and second tissue-engaging elements.

There is still further provided, in accordance with some applications of the present invention, apparatus including:

a stent;

a longitudinal member, which has a distal end that includes an annular loop that extends laterally from the longitudinal member; and a tissue anchor, which is coupled to the annular loop, such that the anchor can rotate with respect to the annular loop, the longitudinal member, and the stent.

In some applications of the present invention, the apparatus further includes a tube, which is sized to pass through a lumen defined by the stent, and which is configured to be removably coupled to the tissue anchor, such that rotation of the tube rotates the tissue anchor. In some applications of the present invention, the tissue anchor is shaped so as to define a passage therethrough, and the tube includes an elongated coupling element, which is initially disposed so as to pass through the passage, thereby coupling the tube to the anchor. In some applications of the present invention, when the tube is removably coupled to the tissue anchor, a longitudinal portion of the tube is positioned alongside the longitudinal member, and no portion of the tube is positioned around the longitudinal member. In some applications of the present invention, the apparatus further includes an adapter holder, which is coupled to the tube, and which is shaped so as to define arms, which have a tendency to expand radially, and which couple the tube to the anchor when the arms are radially compressed. In some applications of the present invention, the apparatus further includes a delivery tool overtube, which is sized to pass through the lumen defined by the stent, the tube is configured to pass through the delivery tool overtube, and the overtube is configured to radially compress the arms when positioned surrounding the arms. In some applications of the present invention, the apparatus further includes an adapter, which is shaped so as to define a cylindrical portion that passes through the annular loop, and which has a distal end that is fixedly coupled to a proximal portion of the tissue anchor, and the tube is configured to be removably coupled to the adapter via the adapter holder when the arms are radially compressed, so as to be removably coupled to the tissue anchor.

In some applications of the present invention, the apparatus further includes an adapter, which is shaped so as to define a cylindrical portion that passes through the annular loop, and which has a distal end that is fixedly coupled to a proximal portion of the tissue anchor, and the tube is configured to be removably coupled to the adapter, so as to be removably coupled to the tissue anchor.

In some applications of the present invention, the apparatus further includes a delivery tool overtube, which is sized to pass through the lumen defined by the stent, and the tube is configured to pass through the delivery tool overtube.

For any of the applications of the present invention described above, the apparatus may further include an adapter, which is shaped so as to define a cylindrical portion that passes through the annular loop, and which has a distal end that is fixedly coupled to a proximal portion of the tissue anchor.

For any of the applications of the present invention described above, the stent may include a plurality of interconnected superelastic metallic struts.

For any of the applications of the present invention described above, the stent may include one or more elongated members, and two or more rings coupled together by the one or more elongated members and by no other elements of the stent.

There is additionally provided, in accordance with some applications of the present invention, a method including:

providing (a) a stent, (b) a longitudinal member, which has a distal end that includes an annular loop that extends laterally from the longitudinal member, and (c) a tissue anchor, which is coupled to the annular loop;

positioning the stent in a blood vessel of a patient;

coupling the tissue anchor to tissue in a vicinity of a heart valve of the patient by rotating the anchor with respect to the annular loop, the longitudinal member, and the stent; and after coupling the tissue anchor to the tissue, deploying the stent such that the stent expands and is implanted in the blood vessel at an implantation site.

In some applications of the present invention, the method further includes, after coupling the tissue anchor to the tissue and before deploying the stent, pulling the anchor toward the implantation site.

In some applications of the present invention, the blood vessel is selected from the group of blood vessels consisting of: a superior vena cava, and an inferior vena cava.

In some applications of the present invention, rotating includes rotating the anchor using a tube, which passes through a lumen defined by the stent, and which is removably coupled to the tissue anchor. In some applications of the present invention, rotating the anchor using a tube includes positioning a longitudinal portion of the tube alongside the longitudinal member, such that no portion of the tube is positioned around the longitudinal member. In some applications of the present invention, rotating includes rotating the anchor using the tube that is coupled to an adapter holder, which is shaped so as to define arms, which have a tendency to expand radially, and which couple the tube to the anchor when the arms are radially compressed. In some applications of the present invention, the method further includes providing a delivery tool overtube, which is sized to pass through the lumen defined by the stent, the tube is configured to pass through the delivery tool overtube, and the overtube is configured to radially compress the arms when positioned surrounding the arms.

In some applications of the present invention, the method further includes providing a delivery tool overtube, which is sized to pass through the lumen defined by the stent, and the tube is configured to pass through the delivery tool overtube.

There is yet additionally provided, in accordance with some applications of the present invention, apparatus including:

a stent, which is configured to assume compressed and expanded states, and which includes:
  one or more elongated members; and
  two or more rings, which are coupled together by the one or more elongated members and by no other elements of the stent, and which define respective planes that are generally perpendicular to the elongated members when the stent is in its expanded state;
a longitudinal member, having a proximal end and a distal end, which proximal end is coupled to the stent; and
a tissue anchor, which is coupled to the distal end of the longitudinal member.

In some applications of the present invention, the stent includes exactly two rings.

In some applications of the present invention, the stent includes exactly one elongated member.

For any of the applications of the present invention described above, the elongated member may include two or more wires coupled to one another.

For any of the applications of the present invention described above, one of the elongated members may be at least partially a continuation of the longitudinal member.

For any of the applications of the present invention described above, each of the rings may have an outer diameter of between 10 and 35 mm, when the stent is in its expanded state.

There is also provided, in accordance with some applications of the present invention, a method including:
  providing a (a) stent, which includes (i) one or more elongated members; and (ii) two or more rings, which are coupled together by the one or more elongated members and by no other elements of the stent, (b) a longitudinal member, having a proximal end and a distal end, which proximal end is coupled to the stent, and (c) a tissue anchor, which is coupled to the distal end of the longitudinal member;
  positioning the stent in a blood vessel of a patient while the stent is in a compressed state;
  coupling the tissue anchor to tissue in a vicinity of a heart valve of the patient; and
  transitioning the stent to an expanded state, such that the rings define respective planes that are generally perpendicular to the elongated members, and anchor the stent to a wall of the blood vessel.

In some applications of the present invention, providing the stent includes providing the stent which includes exactly two rings.

In some applications of the present invention, providing the stent includes providing the stent which includes exactly one elongated member.

In some applications of the present invention, providing the stent includes providing the stent in which one of the elongated members is at least partially a continuation of the longitudinal member.

In some applications of the present invention, positioning the stent in the blood vessel includes positioning the stent in a blood vessel selected from the group of blood vessels consisting of: a superior vena cava, and an inferior vena cava.

In some applications of the present invention, the method further includes monitoring a level of regurgitation of the heart valve in conjunction with the positioning of the stent in the blood vessel.

There is further provided, in accordance with some applications of the present invention, apparatus including a tensioning device, which includes:
  a radially-expandable anchor, which defines an opening;
  a longitudinal member, having proximal and distal ends, which longitudinal member passes through the opening of the radially-expanded anchor, such that the radially-expanded anchor is slidably coupled to the longitudinal member; and
  a tissue anchor, which is coupled to the distal end of the longitudinal member,
  wherein the radially-expandable anchor and the longitudinal member are configured such that the radially-expandable member is lockable to the longitudinal member, so as to prevent movement of the radially-expandable anchor with respect to the longitudinal member at least in a proximal direction toward the proximal end of the longitudinal member.

In some applications of the present invention, at least a portion of the longitudinal member is shaped so as to define ratchet teeth, which engage the radially-expandable anchor, thereby preventing the movement of the radially-expandable anchor with respect to the longitudinal member in the proximal direction.

In some applications of the present invention, the radially-expandable anchor is configured to be crimped to the longitudinal member, so as to prevent the movement of the radially-expandable anchor with respect to the longitudinal member.

In some applications of the present invention, the radially-expandable anchor is configured to generally fall within exactly one plane when radially expanded.

In some applications of the present invention, the radially-expandable anchor, when radially expanded, is shaped so as to define at least one shape selected from the group consisting of a petal and a wing.

For any of the applications of the present invention described above, the apparatus may further include a deployment tube, in which the tensioning device is initially positioned, with the radially-expandable anchor in a radially-compressed state.

There is still further provided, in accordance with some applications of the present invention, a method including:

providing a tensioning device initially positioned in a deployment tube, which tension device includes (a) a longitudinal member, (b) a radially-expanded anchor, which is slidably coupled to the longitudinal member, and (c) a tissue anchor, which is coupled to a distal end of the longitudinal member;

advancing the deployment tube into a left atrium of a patient;

making a hole in an interatrial septum;

advancing the deployment tube from the left atrium through the hole, until a distal end of the deployment tube is positioned within a right atrium;

deploying the tissue anchor from the distal end of the deployment tube, and anchoring the tissue anchor to a portion of cardiac tissue in a vicinity of a tricuspid valve;

withdrawing the deployment tube into the left atrium, thereby releasing the radially-expandable anchor in the left atrium near the septum; and pulling the longitudinal member in a proximal direction, while holding the radially-expandable anchor against a left-atrial side of the septum, and locking the radially-expandable anchor to the longitudinal member, so as to prevent movement of the radially-expandable anchor with respect to the longitudinal member at least in the proximal direction.

In some applications of the present invention, at least a portion of the longitudinal member is shaped so as to define ratchet teeth, which engage the radially-expandable anchor, and locking the radially-expandable anchor to the longitudinal member includes using the ratchet teeth to prevent the movement of the radially-expandable anchor with respect to the longitudinal member in the proximal direction.

In some applications of the present invention, locking the radially-expandable anchor to the longitudinal member includes crimping the radially-expandable anchor to the longitudinal member, so as to prevent the movement of the radially-expandable anchor with respect to the longitudinal member.

In some applications of the present invention, the radially-expandable anchor is configured to generally fall within exactly one plane when radially expanded.

In some applications of the present invention, the radially-expandable anchor, when radially expanded, is shaped so as to define at least one shape selected from the group consisting of: a petal and a wing.

In some applications of the present invention, the method further includes monitoring a level of regurgitation of the tricuspid valve in conjunction with the pulling the longitudinal member.

There is additionally provided, in accordance with some applications of the present invention, apparatus including a tissue anchor, which is configured to assume radially-contracted and radially-expanded states, and which includes:

a post, having a distal tissue-piercing tip, and a greatest diameter of no more than 1.8 mm;

a plurality of ribs, which are coupled to the anchor near the distal tip, such that the ribs can articulate with the post;

a runner, which is slidably coupled to the post, such that the runner can slide along the post; and a plurality of stretchers, which are coupled to the runner and respective ones of the ribs, such that the stretchers can articulate with the runner and the respective ribs.

In some applications of the present invention, the apparatus further includes a catheter, in which the tissue anchor is initially positioned in the radially-contracted state. In some applications of the present invention, the apparatus further includes an inner tube positioned within the catheter, and a proximal end of the runner is initially removably coupled to the inner tube.

For any of the applications of the present invention described above, an outer surface of a proximal end of the runner may be threaded.

For any of the applications of the present invention described above, the anchor may at least partially include a shape-memory alloy.

The present invention will be more fully understood from the following detailed description of applications thereof, taken together with the drawings, in which:

BRIEF DESCRIPTION OF THE DRAWINGS

FIGS. 3A-C are schematic illustrations of apparatus for reducing regurgitation of the heart valve which comprises a single stent, first and second tissue anchor, and first and second tensioning elements, in accordance with some applications of the present invention;

FIGS. 7A-C are schematic illustrations of apparatus for reducing regurgitation of the heart valve which comprises two or three tissue anchors and a tensioning element that couples the tissue anchors, in accordance with some applications of the present invention;

FIGS. 7A-D are schematic illustrations of a delivery system for a helical tissue anchor, in accordance with some applications of the present invention;

FIGS. 11A-B are schematic illustration of another system for repairing a tricuspid valve, in accordance with some applications of the present invention;

DETAILED DESCRIPTION OF APPLICATIONS

Figure 1A:
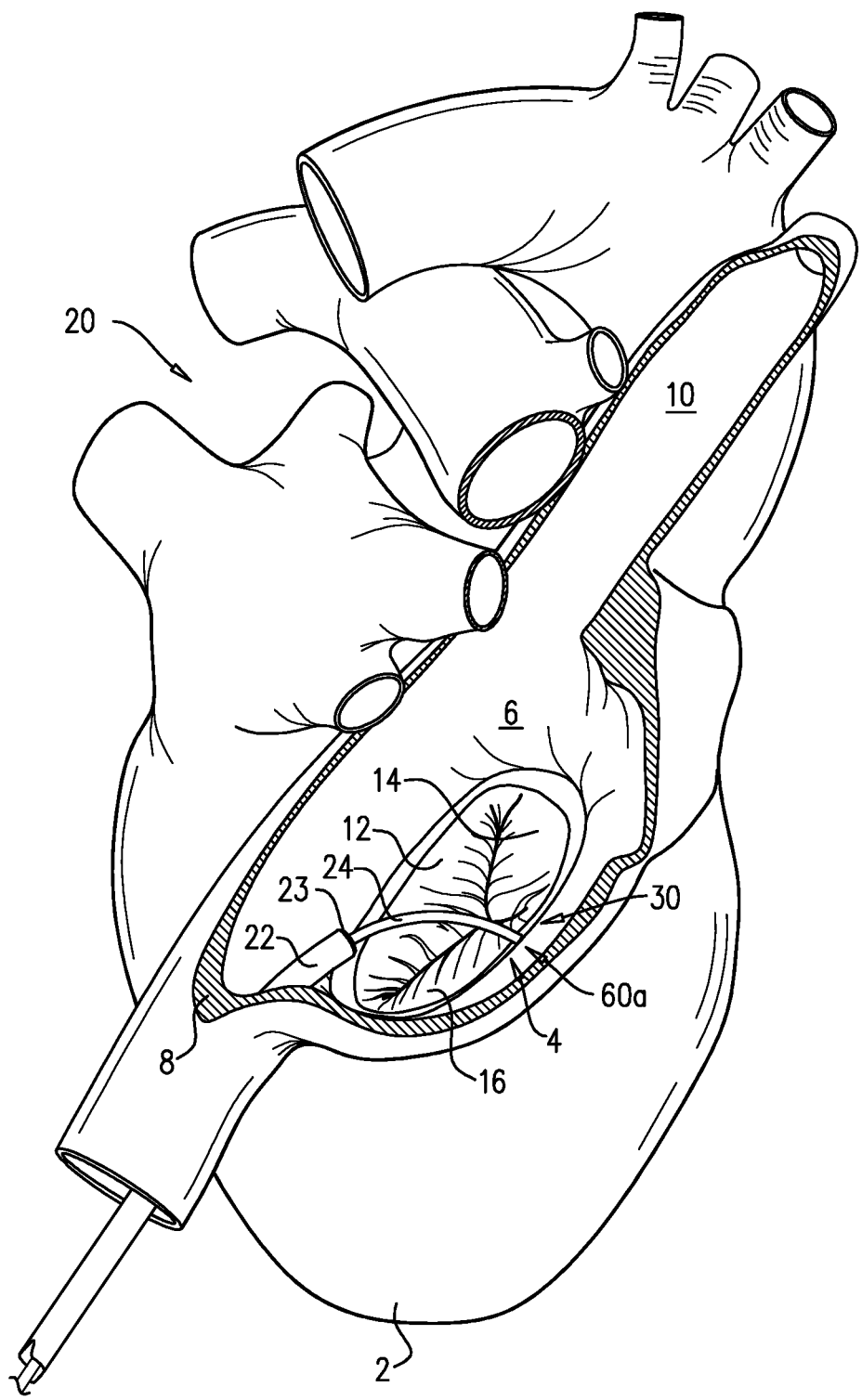
FIGS. 1A-G are schematic illustrations of apparatus for reducing regurgitation of a heart valve which comprises a stent, a tissue anchor, and a tensioning element that couples the stent and the tissue anchor, in accordance with some applications of the present invention.
Figure 1B:
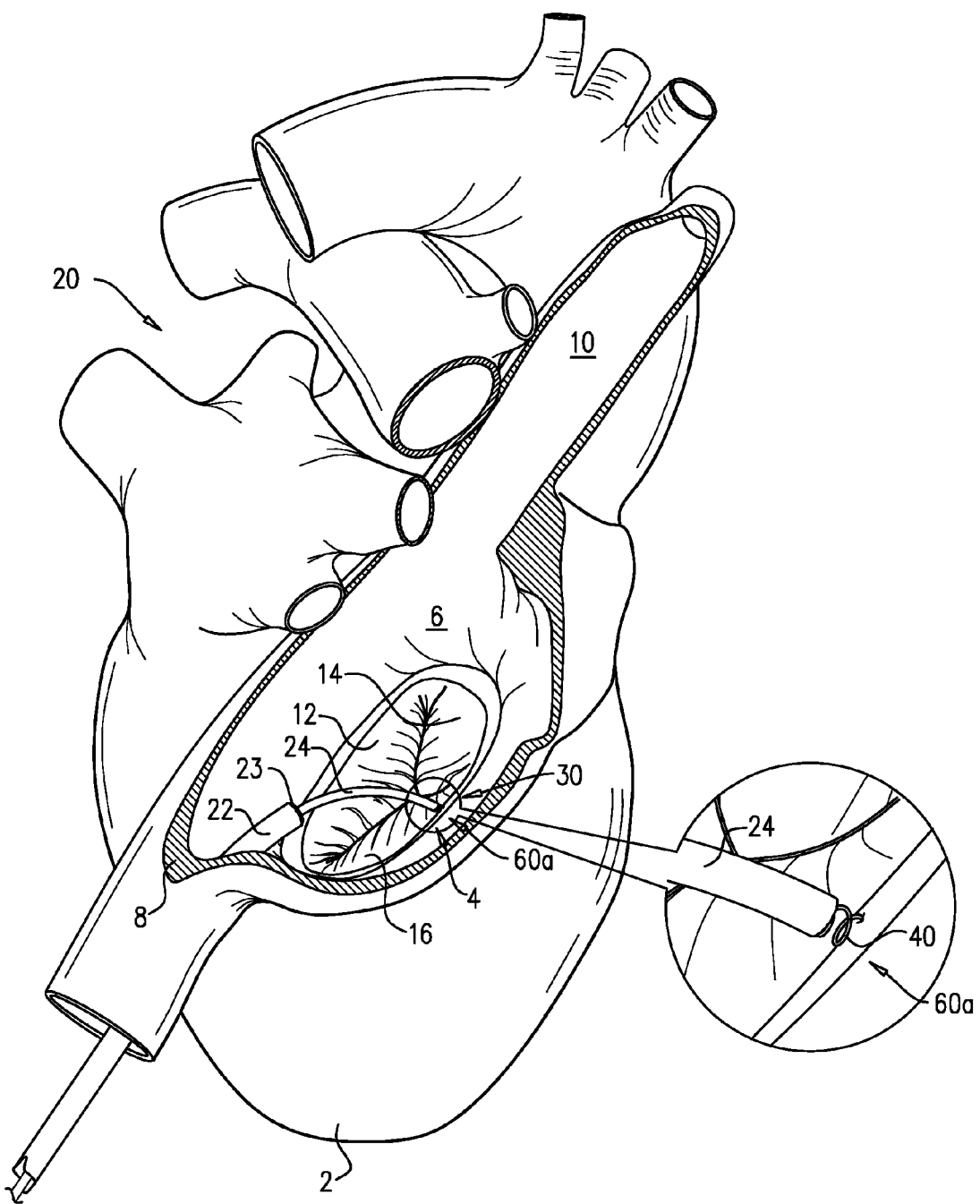
Figure 1C:
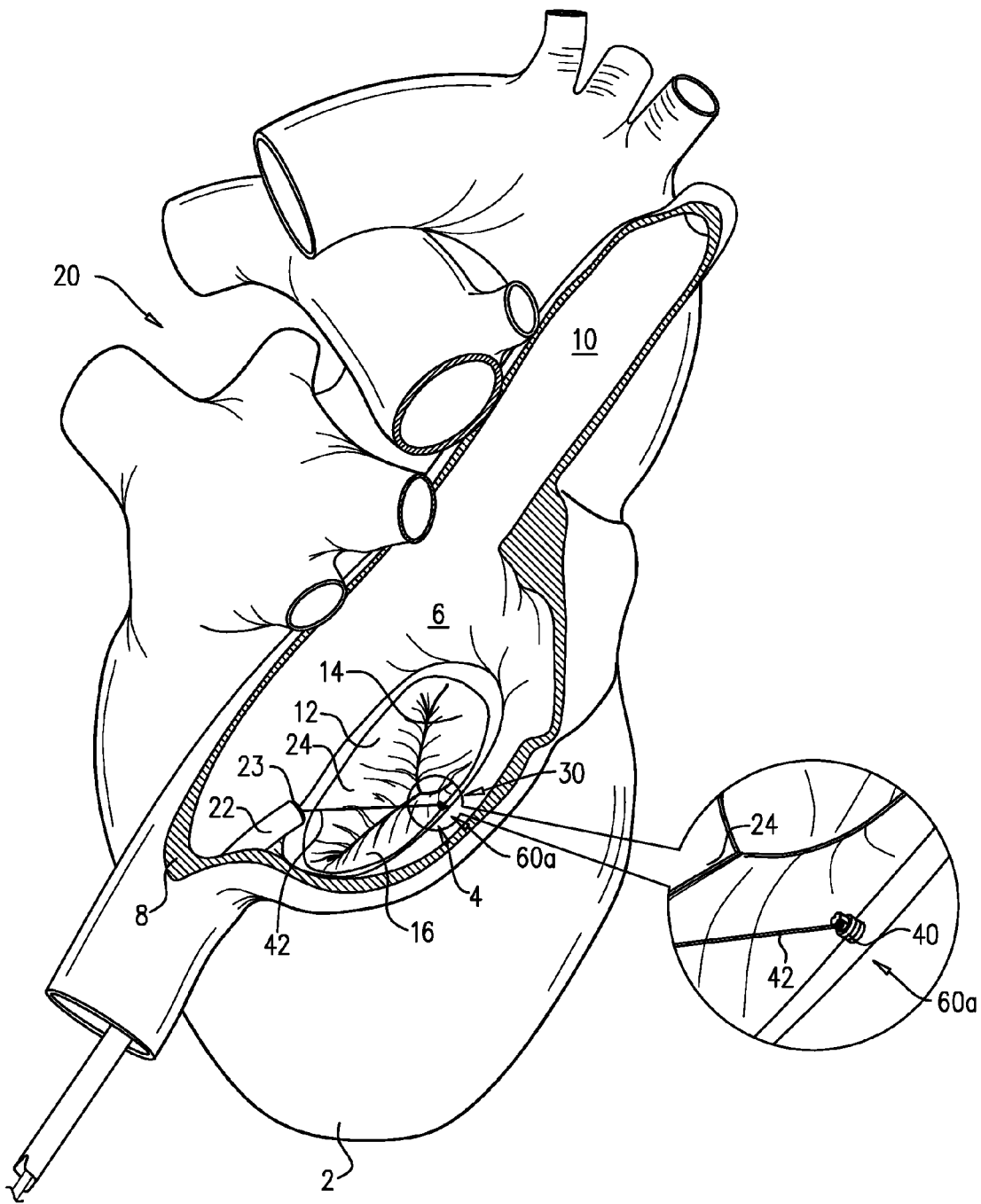
Figure 1D:
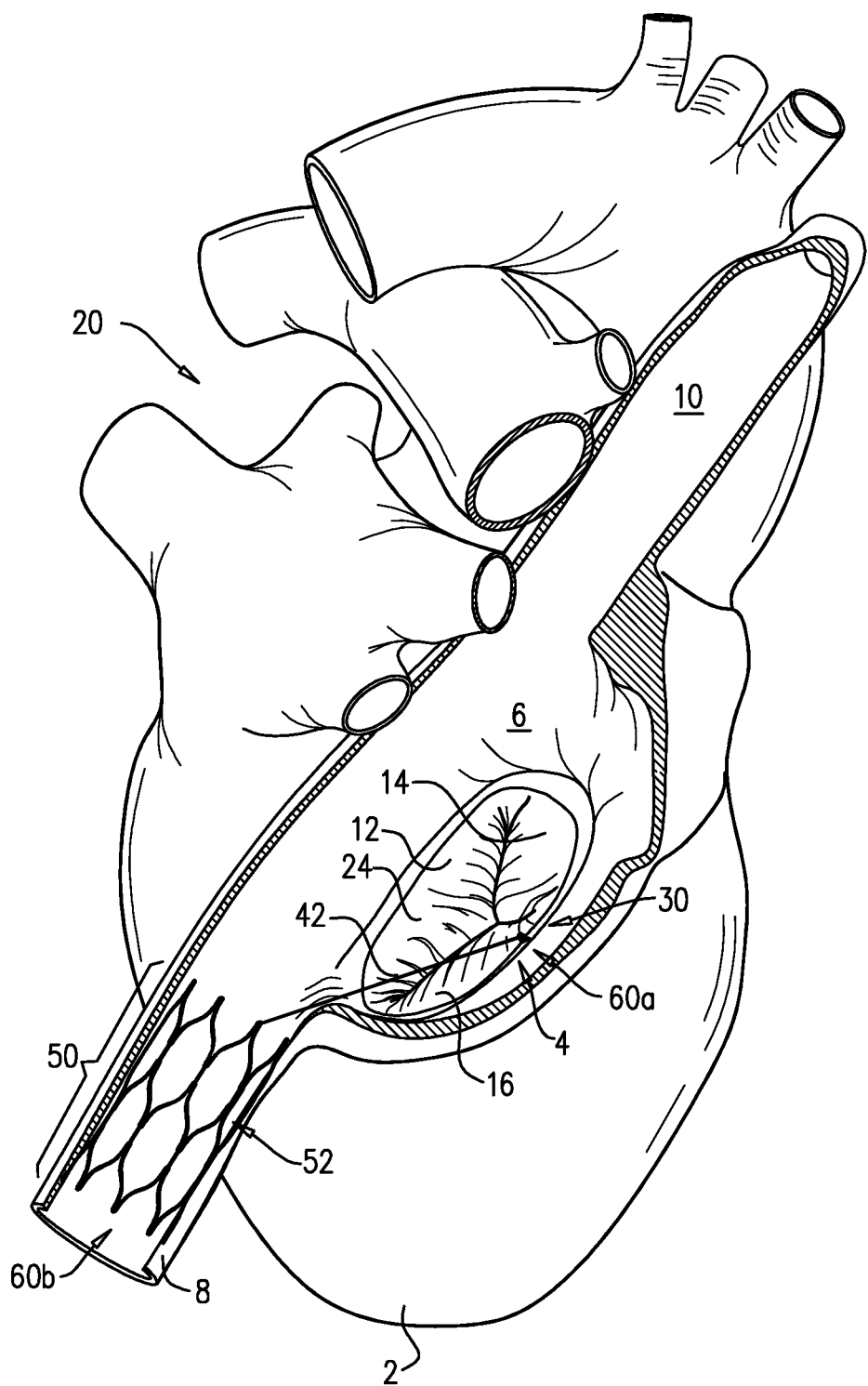
Figure 1E:
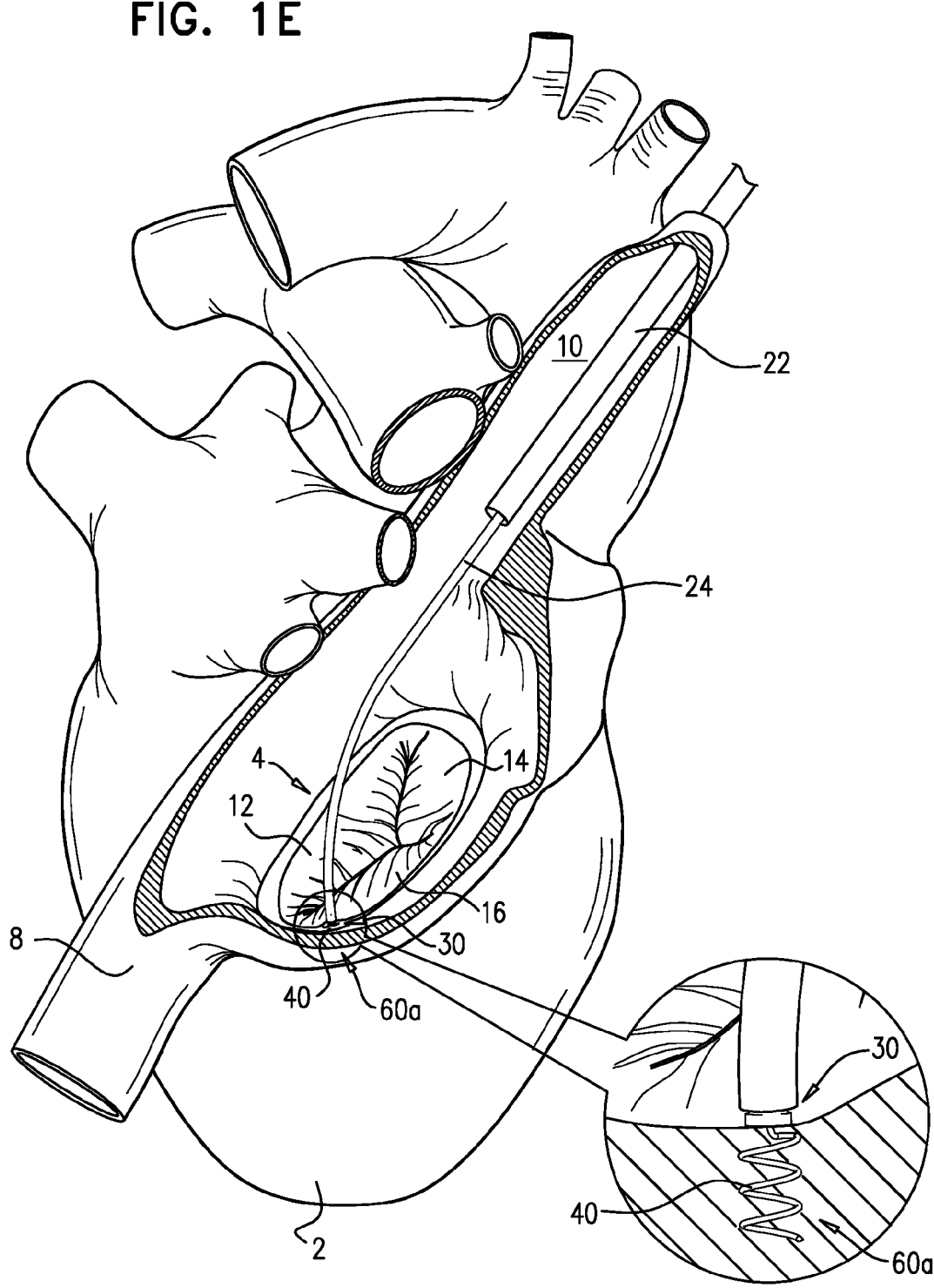
Figure 1F:
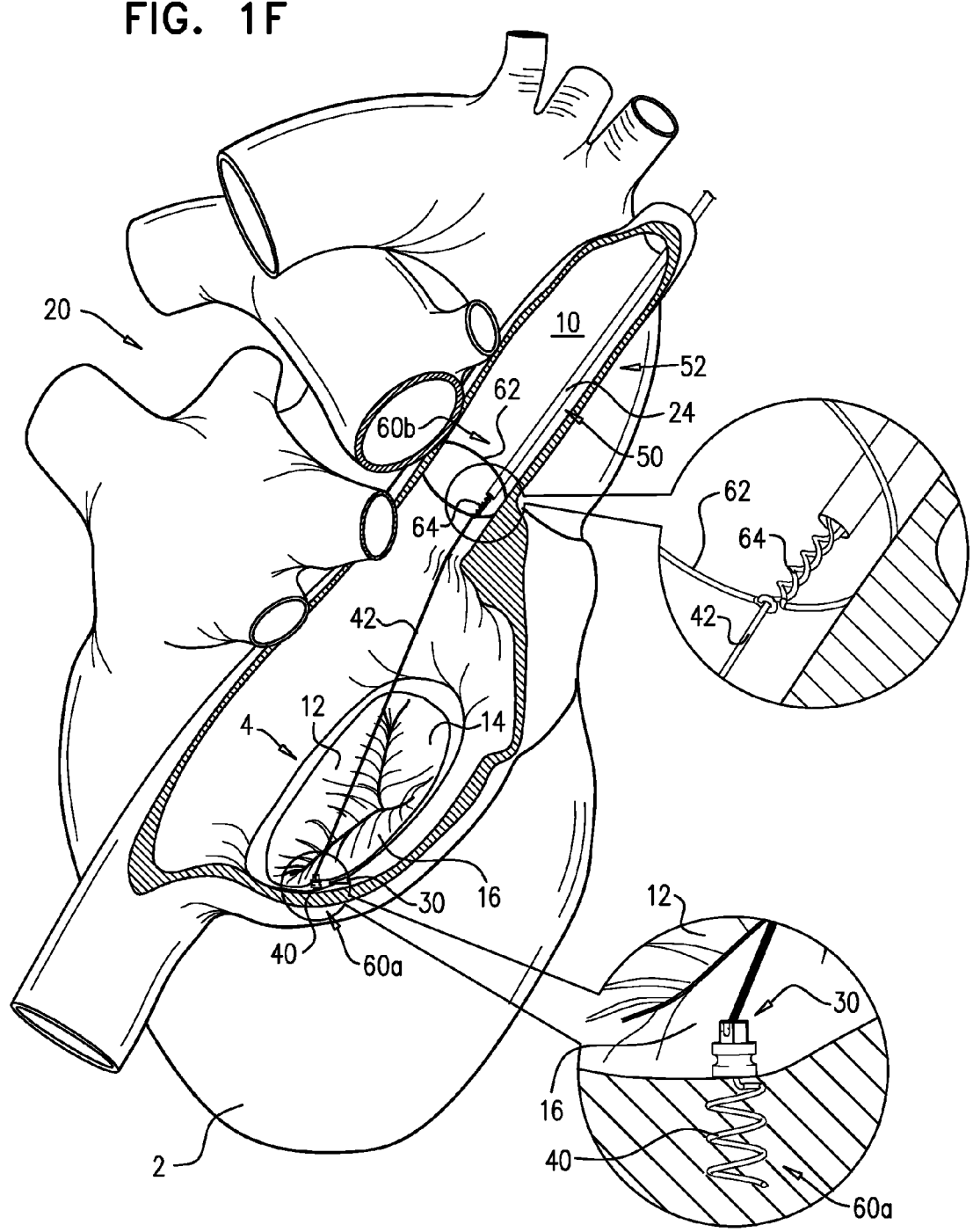
Figure 1G:
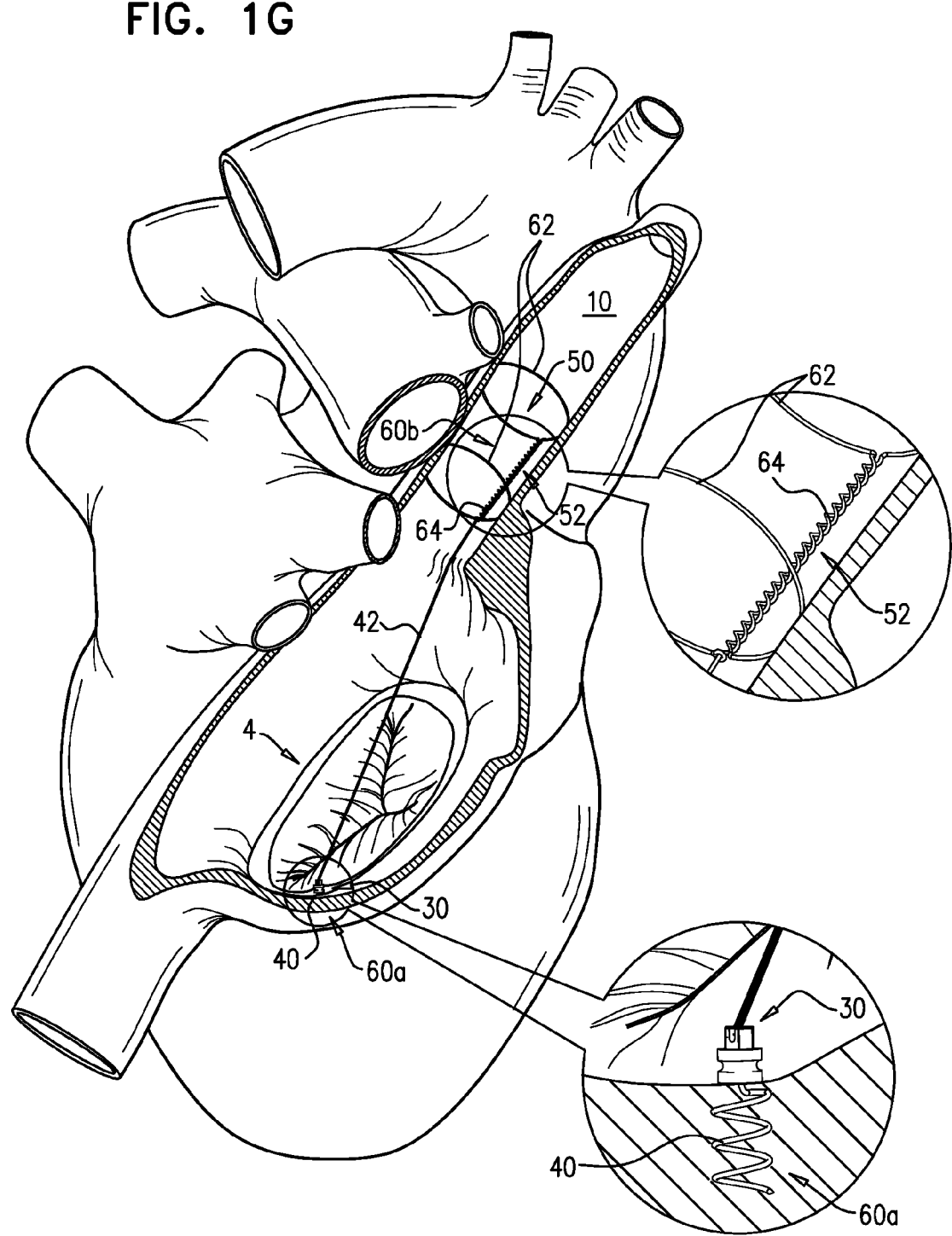

Reference is now made to FIGS. 1A-G, which are schematic illustrations of a system 20 comprising a first tissue-engaging element 60a and a second tissue-engaging element 60b for repairing a tricuspid valve 4 of a heart 2 of a patient, in accordance with some applications of the present invention. First tissue-engaging element 60a comprises a tissue anchor 40 which is designated for implantation at least in part in cardiac tissue at a first implantation site 30. It is to be noted that tissue anchor 40 comprises a helical tissue anchor by way of illustration and not limitation and that tissue anchor 40 may comprise any tissue anchor for puncturing or clamping cardiac tissue, including, but not limited to, the tissue anchors described hereinbelow with reference to FIGS. 13A-E. Second tissue-engaging element 60b comprises a stem 50 which is designated for implantation in a portion of a blood vessel, e.g., a superior vena cava 10 (such as shown in FIGS. 1E-G) or an inferior vena cava 8 (such as shown in FIGS. 1A-D), at a second implantation site 52. First and second tissue-engaging elements 60a and 60b are coupled together by a flexible longitudinal member 42. Typically, a distance between first and second implantation sites 30 and 52 is adjusted by pulling to apply tension to or relaxing longitudinal member 42 and/or by applying tension to at least one of first and second tissue-engaging elements 60a and 60b. Responsively, a distance between the leaflets of tricuspid valve 4 is adjusted to reduce and eliminate regurgitation through valve 4, and thereby, valve 4 is repaired. For some applications, longitudinal member 42 is pulled or relaxed by manipulating second tissue-engaging element 60b, as is described hereinbelow.

For some applications, first and second tissue-engaging elements 60a and 60b and longitudinal member 42 are fabricated from the same material, e.g., nitinol, from a single piece. That is, first and second tissue-engaging elements 60a and 60b and longitudinal member 42 define a single continuous implant unit. For some applications, at least second tissue-engaging element 60b and longitudinal member 42 are fabricated from a single piece.

For other applications, longitudinal member 42 comprises a flexible and/or superelastic material, e.g., nitinol, polyester, stainless steel, cobalt chrome, PTFE, or ePTFE. In some applications of the present invention, longitudinal member 42 comprises a braided polyester suture (e.g., Ticron). In other applications of the present invention, longitudinal member 42 is coated with polytetrafluoroethylene (PTFE). In some applications of the present invention, longitudinal member 42 comprises a plurality of wires that are intertwined to form a rope structure. For some applications, at least a part of longitudinal member 42 comprises a tension spring and/or a plurality of coils.

For some applications, second tissue-engaging element 60b comprises a stent 50 which is advanced toward and expandable in a portion of inferior vena cava 8 (such as shown in FIGS. 1A-D) or superior vena cava 10 (such as shown in FIGS. 1E-G), i.e., a blood vessel that is in direct contact with a right atrium 6 of heart 2 of the patient. Second tissue-engaging element 60b is implanted at second implantation site 52. As shown, first implantation site 30 comprises a portion of an annulus of tricuspid valve 4. Implantation site 30 typically comprises a portion of the annulus of valve 4 that is between (1) the middle of the junction between the annulus and anterior leaflet 14, and (2) the middle of the junction between the annulus and posterior leaflet 16, e.g., between the middle of the junction between the annulus and anterior leaflet 14 and the commissure between the anterior and posterior leaflets. That is, anchor 40 is coupled to, e.g., screwed into, the fibrous tissue of the tricuspid annulus close to the commissure in between anterior leaflet 14 and posterior leaflet 16. Implantation site 30 is typically close to the mural side of valve 4. For such applications, the drawing together of first and second implantation sites 30 and 52 cinches valve 4 and may create a bicuspidization of tricuspid valve 4, and thereby achieve stronger coaptation between anterior leaflet 14 and septal leaflet 12.

For some applications, first implantation site 30 may include a portion of tissue of a wall defining right atrium 6 of heart 2, typically in a vicinity of the annulus of valve 4. For other applications, first implantation site 30 may include a portion of a wall of a right ventricle of heart 2, a ventricular portion of the annulus of valve 4, or a portion of a papillary muscle of the right ventricle of heart 2, as is shown hereinbelow in FIG. 6. First implantation site 30 is typically a distance away from, e.g., generally opposite, second implantation site 52 so that, following adjusting of longitudinal member 42, first and second implantation sites 30 and 52 are drawn together, and thereby at least first and second leaflets, e.g., all three leaflets, of valve 4 are drawn toward each other. For applications in which first implantation site 30 includes a portion of tissue of the annulus, the adjusting of the distance between implantation sites 30 and 52 alters the geometry of (i.e., changes the configuration of) the annulus of valve 4 and thereby draws together the leaflets of valve 4. For applications in which first implantation site 30 includes tissue of a portion of a wall that defines atrium 6, the adjusting of the distance between implantation sites 30 and 52 alters the geometry of (i.e., changes the configuration of) the wall of atrium 6 and thereby draws together the leaflets of valve 4.

FIGS. 1A and 1E show the advancement of a catheter 22 toward atrium 6 of the patient until a distal end 23 of the catheter is disposed within atrium 6, as shown. The procedure is typically performed with the aid of imaging, such as fluoroscopy, transesophageal echo, and/or echocardiography. For some applications, the procedure begins by advancing a semi-rigid guidewire into right atrium 6 of the patient. The guidewire provides a guide for the subsequent advancement of a catheter 22 therealong and into the right atrium. Once distal end 23 of catheter 22 has entered right atrium 6, the guidewire is retracted from the patient's body. Catheter 22 typically comprises a 14-20 F sheath, although the size may be selected as appropriate for a given patient. Catheter 22 is advanced through vasculature into right atrium 6 using a suitable point of origin typically determined for a given patient. For example:

catheter 22 may be introduced into the femoral vein of the patient, through inferior vena cava 8, and into right atrium 6;

catheter 22 may be introduced into the basilic vein, through the subclavian vein through superior vena cava 10, and into right atrium 6; or catheter 22 may be introduced into the external jugular vein, through the subclavian vein through superior vena cava 10, and into right atrium 6.

As shown in FIG. 1A, catheter 22 is advanced through inferior vena cava 8 of the patient and into right atrium 6 using a suitable point of origin typically determined for a given patient. Alternatively, as shown in FIG. 1E, catheter 22 is advanced through superior vena cava 10 of the patient and into right atrium 6 using a suitable point of origin typically determined for a given patient.

Once distal end 23 of catheter 22 is disposed within atrium 6, an anchor-deployment tube 24 is extended from within catheter 22 beyond distal end 23 thereof and toward first implantation site 30. Anchor-deployment tube 24 holds tissue anchor 40 and a distal portion of longitudinal member 42. For some applications, tube 24 is steerable, as is known in the catheter art, while for other applications, a separate steerable element may be coupled to anchor-deployment tube 24. Under the aid of imaging guidance, anchor-deployment tube 24 is advanced toward first implantation site 30 until a distal end thereof contacts cardiac tissue of heart 2 at first implantation site 30. Anchor-deployment tube 24 facilitates atraumatic advancement of first tissue-engaging element 60a toward first implantation site 30. For such applications in which anchor-deployment tube 24 is used, stent 50 is compressed within a portion of tube 24.

An anchor-manipulating tool (not shown for clarity of illustration), which is slidably disposed within anchor-deployment tube 24, is slid distally within tube 24 so as to push distally tissue anchor 40 of first tissue-engaging element 60a and expose tissue anchor 40 from within tube 24, as shown in FIGS. 1B and 1E. For some applications of the present invention, the anchor-manipulating tool is reversibly coupled to anchor 40 and facilitates implantation of anchor 40 in the cardiac tissue. For applications in which anchor 40 comprises a helical tissue anchor, as shown, the operating physician rotates the anchor-manipulating tool from a site outside the body of the patient in order to rotate anchor 40 and thereby screw at least a portion of anchor 40 in the cardiac tissue.

Alternatively, system 20 is provided independently of the anchor-manipulating tool, and anchor-deployment tube 24 facilitates implantation of anchor 40 in the cardiac tissue. For applications in which anchor 40 comprises a helical tissue anchor, as shown, the operating physician rotates anchor-deployment tube 24 from a site outside the body of the patient in order to rotate anchor 40 and thereby screw at least a portion of anchor 40 in the cardiac tissue.

It is to be noted that for some applications of the present invention, anchor 40 comprises a clip, jaws, or a clamp which grips and squeezes a portion of cardiac tissue and does not puncture the cardiac tissue.

Following the implantation of anchor 40 at first implantation site 30, anchor-deployment tube 24 is retracted within catheter 22 in order to expose longitudinal member 42, as shown in FIGS. 1C and 1F. Subsequently, longitudinal member 42 is pulled taut in order to repair tricuspid valve 4, as described hereinbelow.

For some applications, prior to pulling the portion of longitudinal member 42 that is disposed between anchor 40 and distal end 23 of catheter 22, a mechanism that facilitates the application of a pulling force to longitudinal member 42 is fixed in place, as will be described hereinbelow. This fixing in place provides a reference force to system 20 while applying tension to longitudinal member 42 so as to ensure that during the pulling of longitudinal member 42, stent 50 is not pulled from within catheter 22. For some applications, distal end 23 of catheter 22 is fixed in place with respect to longitudinal member 42. Fixing in place catheter 22 stabilizes catheter 22 as longitudinal member 42 is pulled. This enables distal end 23 to remain in place and not slide distally toward implantation site 30 during the adjusting of longitudinal member 42. For some applications of the present invention, a proximal portion of catheter 22 and/or a proximal handle portion coupled to catheter 22 is anchored or otherwise fixed in place at its access location, e.g., by taping or plastering. Alternatively or additionally, a distal portion of catheter 22 comprises an inflatable element coupled to an inflation conduit which runs the length of catheter 22 from the distal portion thereof to a site outside the body of the patient. Prior to the adjusting of longitudinal member 42, the inflatable element is inflated such that it contacts tissue of the vasculature through which catheter 22 is advanced, and thereby catheter 22 is fixed in place. Typically, the inflatable element comprises an annular inflatable element, such that when inflated, the annular inflatable element functions as a seal to hold in place the distal portion of catheter 22.

Following the fixation of the mechanism that facilitates pulling of longitudinal member 42, the physician then pulls longitudinal member 42 and thereby draws together first and second implantation sites 30 and 52.

For some applications, catheter 22 is reversibly coupled to a proximal portion of longitudinal member 42 by being directly coupled to the proximal portion of member 42 and/or catheter 22 is reversibly coupled to second tissue-engaging element 60b. For example, catheter 22 may be reversibly coupled to stent 50 by the stent's application of a radial force against the inner wall of catheter 22 because of the tendency of stent 50 to expand radially. Following implantation of first tissue-engaging element 60a, catheter 22 (or an element disposed therein) is then pulled proximally to apply tension to longitudinal member 42, which, in such an application, functions as a tensioning element. For some applications, catheter 22 pulls on second tissue-engaging element 60b in order to pull longitudinal member 42. For other applications, catheter 22 pulls directly on longitudinal member 42. For yet other applications, a pulling mechanism pulls on longitudinal member 42, as is described hereinbelow with reference to FIGS. 7A-D.

Pulling longitudinal member 42 pulls taut the portion of longitudinal member 42 that is disposed between anchor 40 and distal end 23 of catheter 22. Additionally, longitudinal member 42 may be pulled or relaxed in order to adjust the distance between first and second implantation sites 30 and 52. Responsively to the pulling of longitudinal member 42, at least the anterior and septal leaflets of tricuspid valve 4 are drawn together because the geometry of the annulus and/or of the wall of atrium 6 is altered in accordance with the pulling of longitudinal member 42 and depending on the positioning of first tissue-engaging element 60a. For some applications, during the pulling of longitudinal member 42 by catheter 22, a level of regurgitation of tricuspid valve 4 is monitored. Longitudinal member 42 is pulled until the regurgitation is reduced or ceases.

Once the physician determines that the regurgitation of valve 4 is reduced or ceases, and valve 4 has been repaired, the physician decouples catheter 22 from second tissue-engaging element 60b disposed therein and/or from longitudinal member 42, and then retracts catheter 22 in order to expose second tissue-engaging element 60b, i.e., stent 50. During the advancement of catheter 22 toward atrium 6, stent 50 is disposed within a distal portion of catheter 22 in a compressed state. Following initial retracting of catheter 22, stent 50 is exposed and is allowed to expand and contact a wall of inferior vena cava 8. FIG. 1F shows stent 50 partially exposed and partially expanded, and FIGS. 1D and 1G show the stent fully exposed and fully expanded.

Responsively to the expanding, stent 50 is implanted in second implantation site 52 and maintains the tension of longitudinal member 42 on anchor 40 and thereby on the portion of cardiac tissue to which anchor 40 is coupled.

Reference is now made to FIGS. 1E-G. It is to be noted that catheter 22 may enter via superior vena cava 10, as described hereinabove. For such applications, first implantation site 30 may comprise an area of the annulus of valve 4, or a portion of the wall defining atrium 6 that is opposite superior vena cava 10.

Figure 5A:
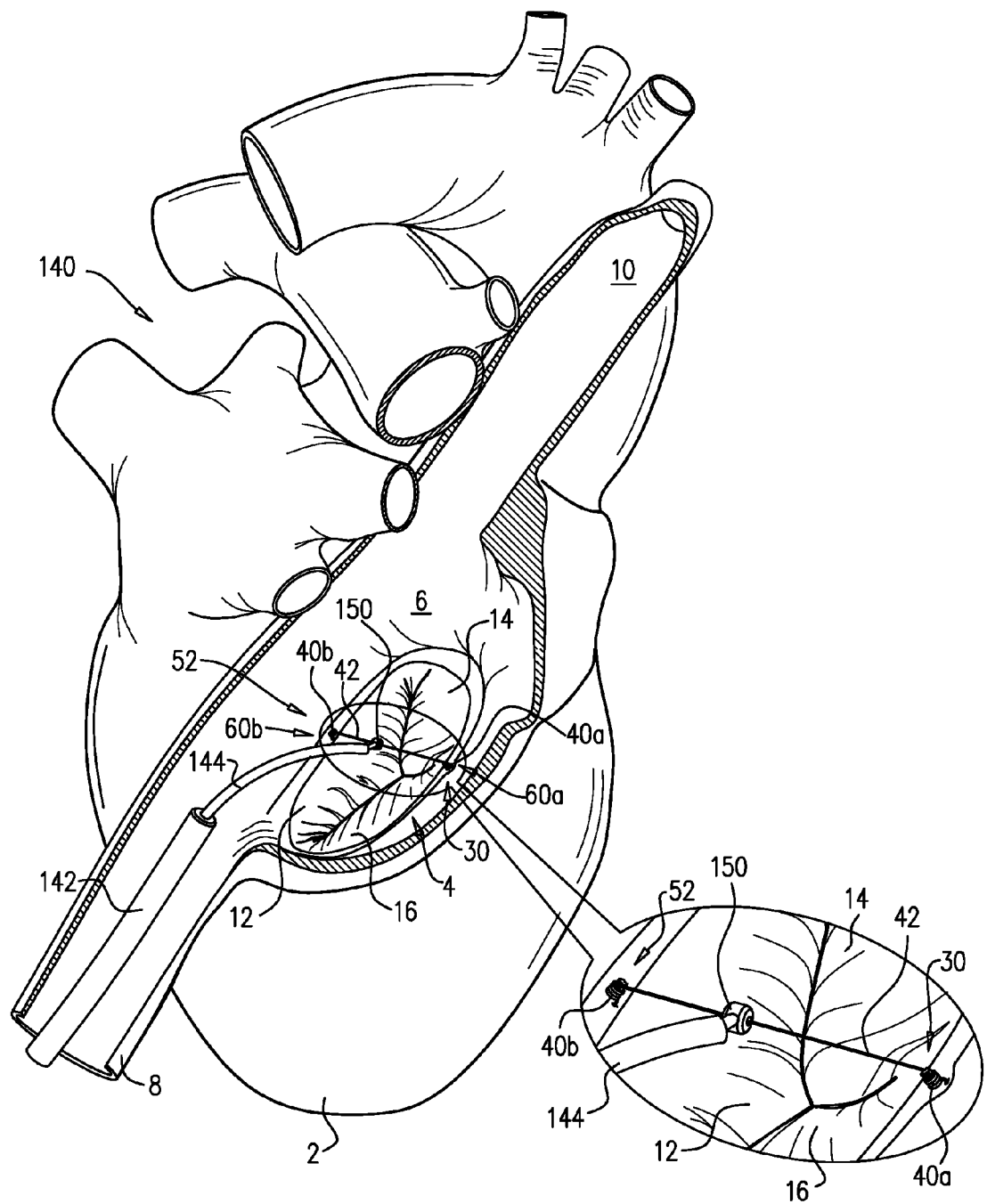
Figure 5B:
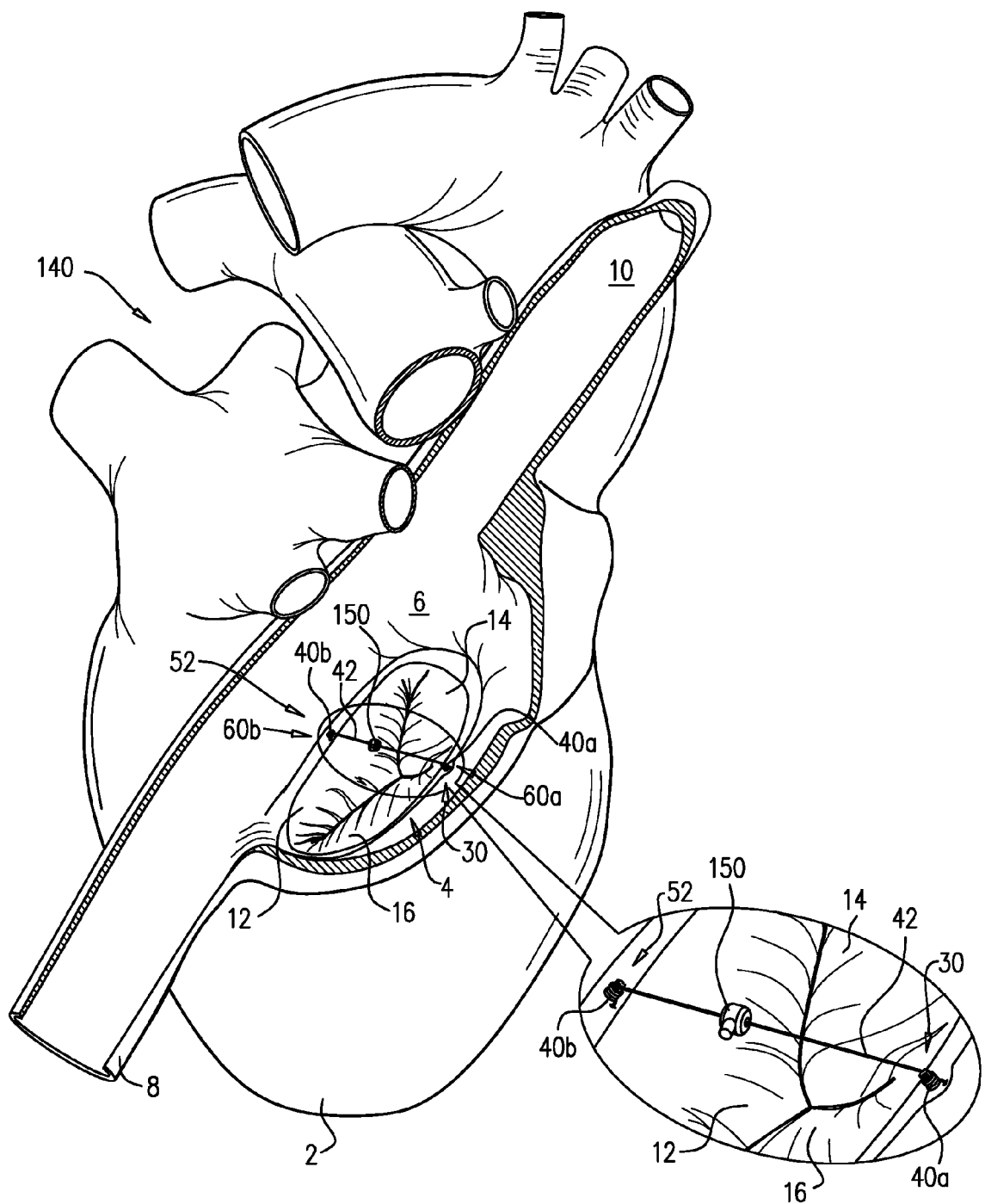
Figure 5C:
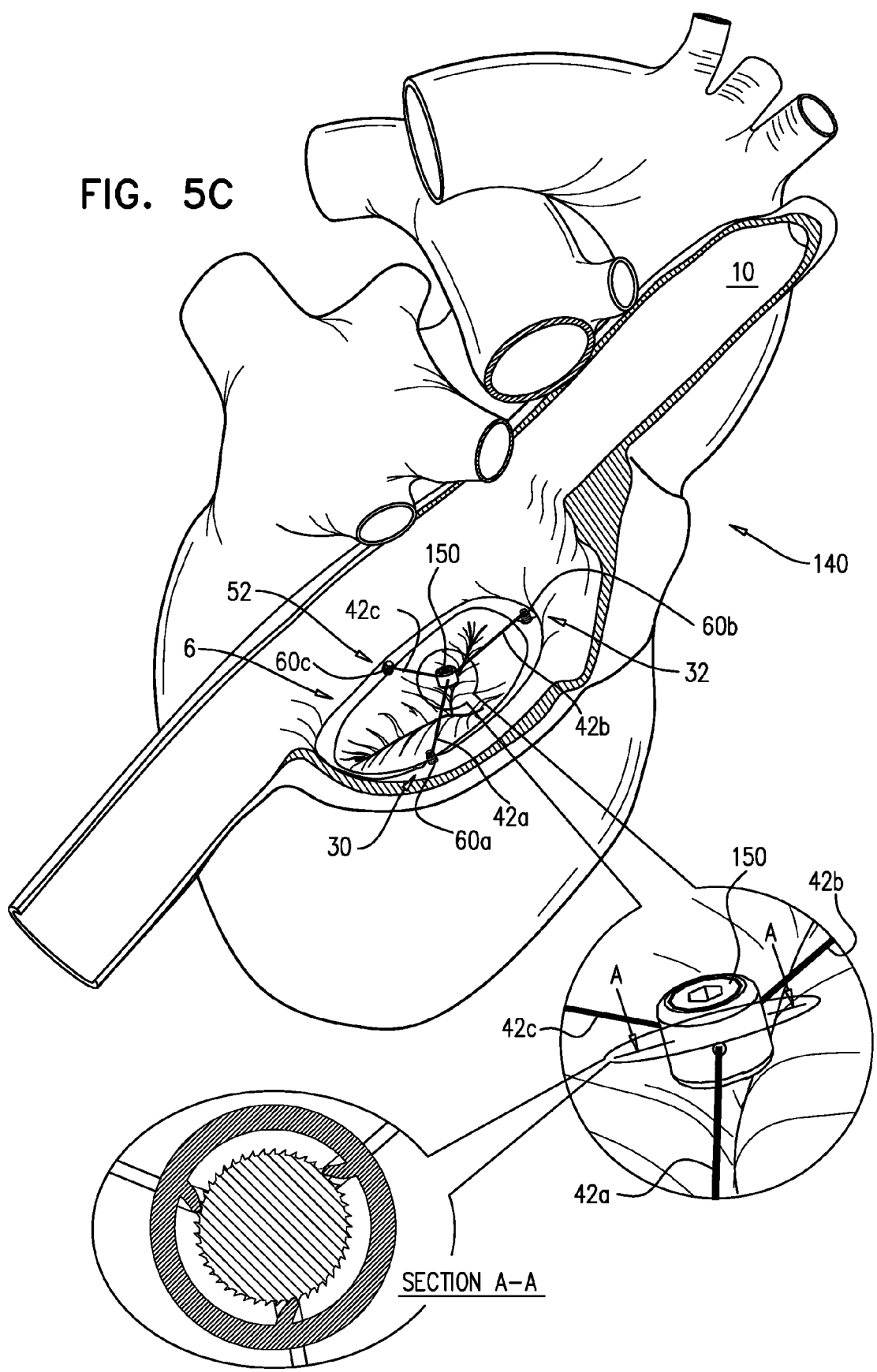

Reference is again made to FIGS. 1A-G. For some applications, following the implantation of first and second tissue-engaging elements 60a and 60b, a distance between first and second tissue-engaging elements 60a and 60b is adjusted by an adjustable mechanism, as described hereinbelow with reference to FIGS. 5A-B or 5C. In such applications, a length of longitudinal member 42 between first and second tissue-engaging elements 60a and 60b may be adjusted by an adjusting mechanism 150, as shown in FIGS. 5A-B or 5C. Adjusting mechanism 150 typically comprises a mechanical element which shortens a distance of longitudinal member 42 between first and second tissue-engaging elements 60a and 60b. For some applications, adjustable mechanism 150 may be permanently coupled to longitudinal member 42 (not shown) and comprises an adjusting element, e.g., a spool for looping portions of longitudinal member 42 therearound, a crimping bead for crimping and shortening a portion of longitudinal member 42, a ratchet element, or a deforming element which deforms a portion of longitudinal member 42 in order to shorten its length between first and second tissue-engaging elements 60a and 60b. For other applications, adjusting mechanism 150 comprises only an adjusting tool 144, as shown in FIG. 5A. In such applications, adjusting tool 144 may comprise an adjusting element, e.g., a crimping bead for crimping and shortening a portion of longitudinal member 42, or a deforming element which deforms a portion of longitudinal member 42 in order to shorten its length between first and second tissue-engaging elements 60a and 60b. In either application, a level of regurgitation of valve 4 may be monitored during the adjusting of the distance between first and second tissue-engaging elements 60a and 60b by adjusting mechanism 150.

For some applications, such as shown in FIG. 1D, stent 50 comprises a plurality of interconnected superelastic metallic struts, arranged so as to allow crimping the stent into a relatively small diameter (typically less than 8 mm) catheter, while allowing deployment to a much larger diameter (typically more than 20 mm) in the vena cava, while still maintaining radial force against the vena cava tissue, in order to anchor stent 50 to the wall of the vena cava by friction. Alternatively or additionally, for some applications, such as shown in FIGS. 1F-G, stent 50 comprises two or more rings 62, which are configured to expand in the superior or inferior vena cava, in order to anchor stent 50 to the wall of the vena cava by friction. Typically, the rings are sized to push against and make small indentions in the wall of the vena cava. The rings may also reduce the risk of stent fatigue and stent fracture. Typically, the rings are configured to self-expand upon being released from catheter 22, and may, for example, comprise a shape-memory alloy, such as nitinol. For some applications, the rings are elliptical, such as circular, or have other shapes.

Rings 62 are coupled together by one or more elongated members 64, such as exactly one elongated member 64 (as shown), or between two and four elongated members 64 (configurations not shown). Typically, no elements of stent 50, other than elongated members 64, couple the rings together. Typically, each of elongated members 64 comprises one or more wires; for applications in which a plurality of wires is provided, the wires are typically tightly coupled to one another, such as by twisting (as shown), so as to define a single elongated member 64. Optionally, one of elongated members 64 is at least partially a continuation of longitudinal member 42 (e.g., one of the wires of elongated member 64 is a continuation of longitudinal member 42). For some applications, rings 62 and elongated members 64, and, optionally, longitudinal member 42, are fabricated from a single piece, such as shown in FIG. 1G. For some applications, stent 50 comprises exactly two rings (as shown), while for other applications, stent 50 comprises more than two rings 62, for example, between three and five rings (configuration not shown).

Typically, when stent 50 is in its expanded state, respective planes defined by rings 62 are generally perpendicular to elongated members 64, such that the rings, when positioned in the superior or inferior vena cava, are generally perpendicular to an axis of the vena cava, and thus make good contact with the wall of the vena cava.

Typically, rings 62 are sized in accordance with the patient's particular anatomy, so that when expanded, the rings are 10-25% larger than the nominal vena cava diameter. For example, for a patient who has a 20 mm vena cava, the surgeon may use rings with an outer diameter of 22-25 mm. For some applications, each of rings 62 has an outer diameter of at least 10 mm, no more than 35 mm, and/or between 10 and 35 mm, when stent 50 is in its expanded state. Typically, when the stent is in its expanded state, a distance between two of rings 62 that are longitudinally farthest from each other is at least 10 mm, no more than 40 mm, and/or between 10 and 40 mm (for applications in which stent 50 comprises exactly two rings, this distance is the distance between the two rings). For applications in which stent 50 comprises exactly two rings, a length of elongated members 64 equals the above-mentioned distance.

For some applications, such as those described with reference to FIGS. 1A-D and 1E-F, longitudinal member 42 has a length of at least 10 mm, no more than 40 mm, and/or between 10 and 40 mm.

The configuration of stent 50 that is shown in FIG. 1D deployed in inferior vena cava 8 may instead be deployed in superior vena cava 10 (deployment not shown), and the configuration of stent 50 shown in FIGS. 1F-G deployed in superior vena cava 10 may instead be deployed in inferior vena cava 8 (deployment not shown). The configuration of stent 50 shown in FIGS. 1F-G may be used in any of the stent configurations described herein, including those described hereinbelow with reference to FIGS. 2A-B, 3A-B, 4A-C, 6, and/or 7A-D.

Reference is now made to FIGS. 7A-D, which are schematic illustrations of a delivery tool system 200 for implanting anchor 40, in accordance with some applications of the present invention. Delivery tool system 200 may be used, for example, to rotate and implant an anchor in combination with the applications described herein with reference to FIGS. 1A-G, 2A-B, 3A-C, 5A-C, 6, 8A-E, 9A-E, 11A-B, 12A-E, and/or 14A-D. Although longitudinal member is shown in FIGS. 7A-D as being fixed to stent 50, this is not necessarily the case, and tool system 200 thus may also be used in combination with the applications that do not utilize stent 50, such as those described herein with reference to FIGS. 3C, 5A-C, 11A-B, 12A-E, and/or 14A-D.

Figure 7A:
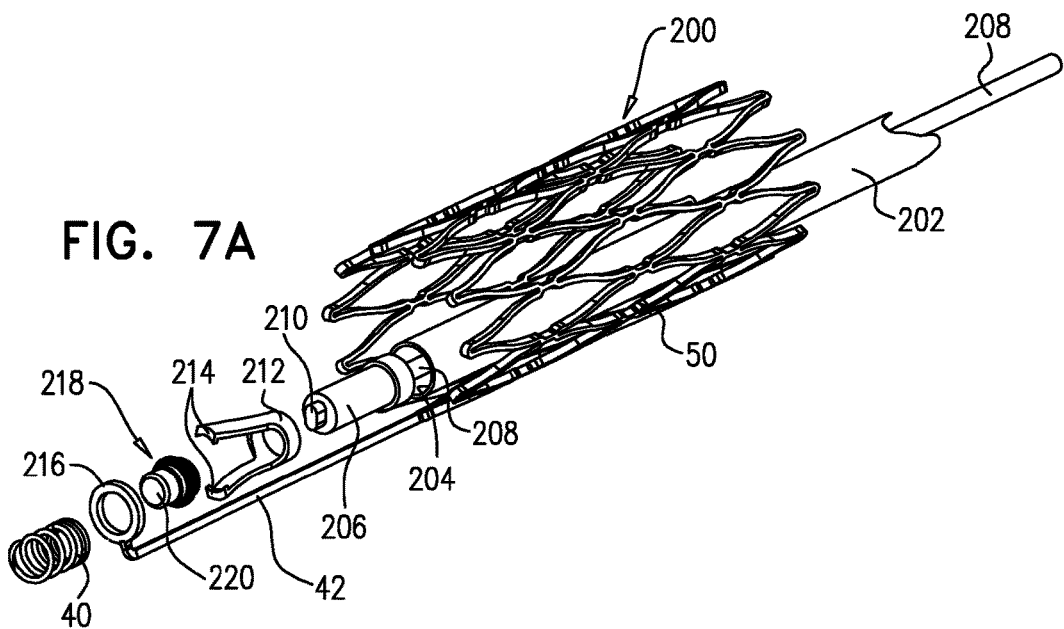

Reference is now made to FIGS. 1A-G and 7A-D. It is to be noted that anchor 40 may be implanted using delivery tool system 200. FIG. 7A shows an exploded view of the components of delivery tool system 200 and its spatial orientation relative to stent 50, longitudinal member 42, and anchor 40. In such an application, a distal end of longitudinal member 42 comprises an annular loop 216, through which a portion of anchor 40 is coupled to the distal end of longitudinal member 42. For some such applications, stent 50, longitudinal member 42, and anchor 40 are not fabricated from the same piece, as described hereinabove; rather, only stent 50, longitudinal member 42, and annular loop 216 are typically fabricated from a single piece, and anchor 40 is coupled to longitudinal member 42 via annular loop 216. Alternatively, as mentioned above, longitudinal member 42 is not coupled to stent 50, such as for applications in which stent 50 is not provided.

Figure 7B:
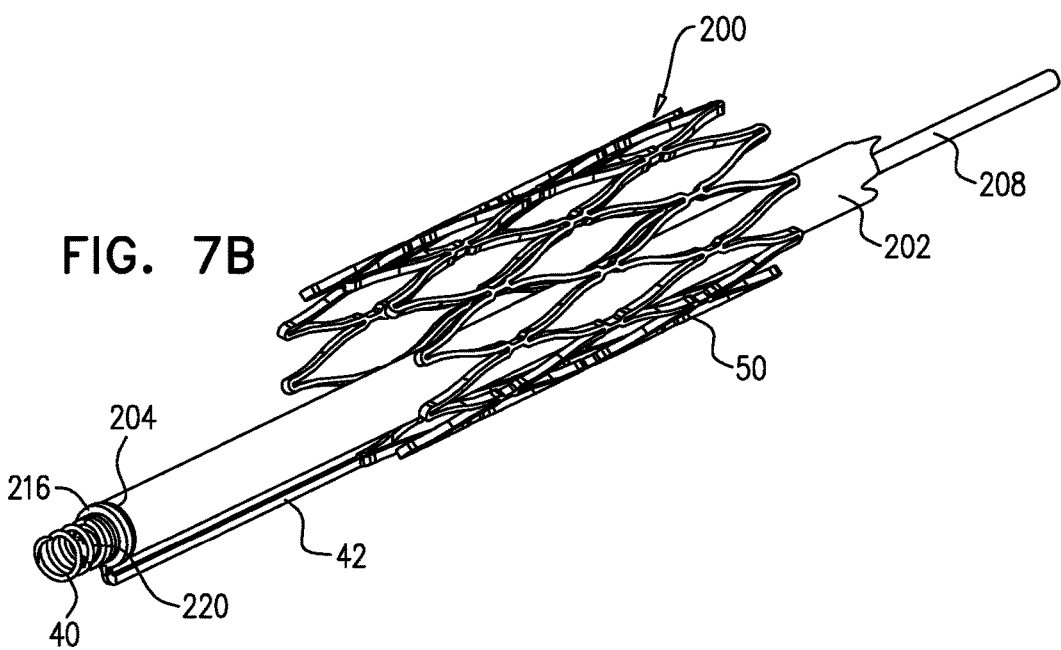

System 200 typically comprises an adapter 218, which, for some applications, is shaped so as to define an annular proximal portion and a distal cylindrical portion having a distal end 220. During the manufacture of system 200, distal end 220 of the cylindrical portion of adapter 218 is slid through annular loop 216 at the distal end of longitudinal member 42, thereby coupling adapter 218 to the distal end of longitudinal member 42. Distal end 220 of adapter 218 is then welded or otherwise fixedly coupled to a proximal portion of an inner lumen of anchor 40, as shown in FIG. 7B. This coupling arrangement of anchor 40 to annular loop 216 and adapter 218 enables anchor 40 to rotate about a central longitudinal axis of delivery system 200, freely within annular loop 216. That is, delivery tool system 200 rotates anchor 40 without rotating longitudinal member 42 and stent 50 (if provided), as described hereinbelow.

Delivery tool system 200 comprises a delivery tool overtube 202 having a distal end thereof. For application in which stent 50 is provided, delivery tool overtube 202 is housed within catheter 22 such that a distal portion thereof passes in part through the lumen of stent 50 and a distal end 204 thereof extends toward tissue anchor 40. During delivery of tissue anchor 40 and stent 50 toward their respective implantation sites, deliver tool system 200 assumes the configuration shown in FIG. 7B. It is to be noted, however, that stent 50 is compressed around the portion of overtube 202 that extends through the lumen of stent 50 (not shown for clarity of illustration), and that catheter 22 (not shown for clarity of illustration) surrounds system 200 (and thereby compresses stent 50).

Reference is again made to FIG. 7A. Overtube 202 houses a torque-delivering and an anchor-pulling tube 208 and facilitates slidable coupling of tube 208 to overtube 202. A distal end of torque-delivering and anchor-pulling tube 208 is coupled to a manipulator 206 which is shaped so as to define a coupling 210 which couples manipulator 206 to adapter 218, and thereby, to anchor 40. In order to rotate anchor 40, torque-delivering and anchor-pulling tube 208 is rotated. As torque-delivering and anchor-pulling tube 208 is rotated, manipulator 206 is rotated in order to screw anchor 40 into the cardiac tissue of the patient. As adapter 218 rotates, the cylindrical portion thereof rotates freely within annular loop 216. This coupling arrangement of adapter 218 (and thereby anchor 40) to loop 216 (and thereby longitudinal member 42) enables the physician to rotate and implant anchor 40 without rotating longitudinal member 42 and stent 50 (if provided).

Following rotation of anchor 40, torque-delivering and anchor-pulling tube 208 is pulled by the physician in order to pull on anchor 40 and thereby on the portion of cardiac tissue to which anchor 40 is implanted at first implantation site 30. Tube 208 is typically coupled at a proximal end thereof to a mechanical element, e.g., a knob, at the handle portion outside the body of the patient. The physician pulls on tube 208 by actuating the mechanical element that is coupled to the proximal end of tube 208. This pulling of tube 208, and thereby of anchor 40 and of cardiac tissue at first implantation site 30, draws first implantation site toward second implantation site 52 and thereby draws at least anterior leaflet 14 toward septal leaflet 12 in order to achieve coaptation of the leaflets and reduce regurgitation through valve 4.

For some applications in which stent 50 is provided, following the pulling of anchor 40, stent 50 is positioned at second implantation site 52. Catheter 22 is then retracted slightly along overtube 202 so as to pull taut longitudinal member 42 and to ensure that tension is maintained at first implantation site 30 and along longitudinal member 42. Stent 50 is then deployed when the physician holds torque-delivering and anchor-pulling tube 208 and then retracts proximally either (1) catheter 22 or (2) a sheath (i.e., that is disposed within catheter 22 and surrounds stent 50), around stent 50 so as to deploy stent 50 from within either (1) catheter 22 or (2) the sheath disposed within catheter 22.

It is to be noted that stent 50 is retrievable following at least partial deployment thereof, e.g., following deployment of up to ½ or up to ⅓ of stent 50. In such an application, following the initial retraction proximally of catheter 22 from around stent 50 in order to deploy at least a distal portion of stent 50, catheter 22 is advanceable distally so as to compress and retrieve the at least partially-deployed stent back into the distal end portion of catheter 22. Alternatively, catheter 22 houses a sheath which compresses stent 50 during delivery of stent to second implantation site 52. During the initial retracting of catheter 22 proximally, the sheath surrounding stent 50 is also retracted in conjunction with the retracting of catheter 22. Following the at least partial deployment of stent 50 in order to deploy at least a distal portion of stent 50, the sheath is advanceable distally (while catheter 22 remains in place) so as to compress and retrieve the at least partially-deployed stent back into the distal end portion of the sheath. The sheath is then retracted into catheter 22. For such applications of the present invention in which stent 50 is retrievable following at least partial deployment thereof, anchor 40 can then be unscrewed from first implantation site 30 and the entire implant system may be extracted from the body, or repositioned in the heart, depending on the need of a given patient.

For applications in which stent 50 is retrievable, in order to retrieve stent 50 (i.e., prior to the decoupling of manipulator 206 from adapter 218 and thereby from anchor 40), the physician holds torque-delivering and anchor-pulling tube 208 and then advances distally either (1) catheter 22 or (2) the sheath disposed within catheter 22, around stent 50 so as to compress stent 50 within either (1) catheter 22 or (2) the sheath disposed within catheter 22. Torque-delivering and anchor-pulling tube 208 may then be rotated in order to unscrew anchor 40 from the tissue, and the entire system may be extracted from the body, or repositioned in the heart, depending on the need of a given patient.

Reference is again made to FIGS. 7A-D. FIGS. 7C-D show the decoupling and release of torque-delivering and anchor-pulling tube 208 and manipulator 206 from adapter 218 and anchor 40. This release occurs typically following the deployment of stent 50 (if provided), as described hereinabove. As shown in FIG. 7A, system 200 comprises a releasable adapter holder 212 which is shaped so as to define arms 214 which have a tendency to expand radially. Holder 212 surrounds manipulator 206, as shown in FIG. 7C.

During the delivery of anchor 40 toward implantation site 30 and the subsequent rotation of anchor 40 to screw anchor 40 into tissue at site 30, a distal end 204 of overtuhe 202 is disposed adjacently to loop 216 such that a distal end portion of overtube 202 surrounds and compresses arms 214 of holder 212 (as shown in FIG. 7B). Following the pulling of anchor 40 by torque-delivering and anchor-pulling tube 208, overtube 202 is retracted slightly in order to expose arms 214 of holder 212. Responsively, arms 214 expand radially (FIG. 7C) and release adapter 218 (and thereby anchor 40) from holder 212.

As shown in FIG. 7D, overtube 202 is held in place while the physician retracts tube 208 so as to collapse and draw arms 214 into the distal end portion of overtuhe 202. Overtube 202 is then slid proximally within catheter 22 leaving behind anchor 40, adapter 218 coupled to anchor 40, loop 216, longitudinal member 42, and stent 50 (if provided). Catheter 22, that houses overtube 202 and the components disposed therein, is extracted from the body of the patient.

For some applications, such as those described hereinabove with reference to FIGS. 7A-D, longitudinal member 42 has a length of at least 10 mm, no more than 40 mm, and/or between 10 and 40 mm.

Reference is again made to FIGS. 1A-G. It is to be noted that tissue-engaging elements 60a and 60b may be implanted at their respective implantation sites 30 and 50, as described hereinabove, by advancing catheter 22 and tissue-engaging elements 60a and 60b through superior vena cava 10, mutatis mutandis.

Figure 2A:
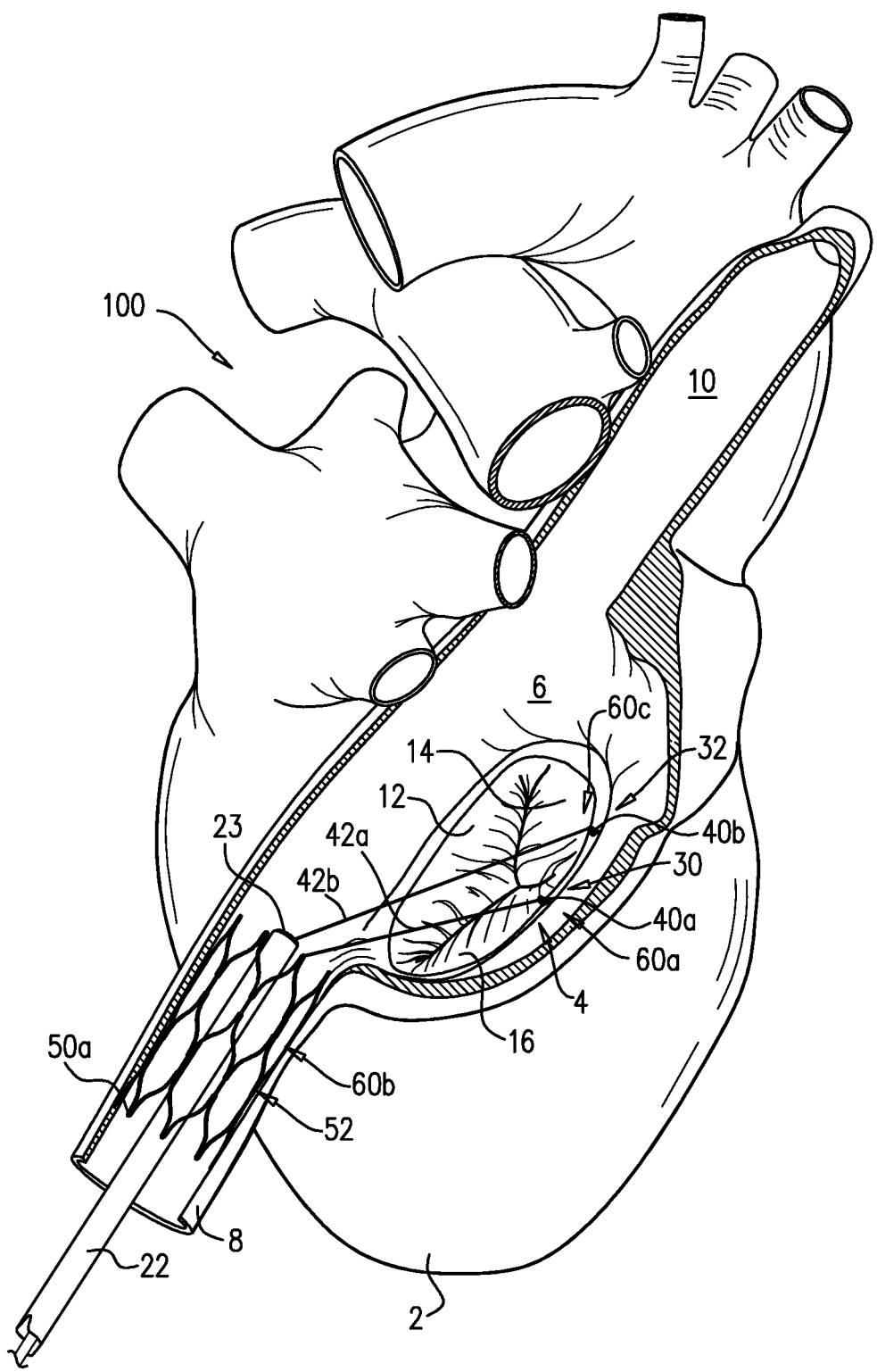
FIGS. 2A-B are schematic illustrations of apparatus for reducing regurgitation of the heart valve which comprises first and second stents, first and second tissue anchor, and first and second tensioning elements; in accordance with some applications of the present invention.
Figure 2B:
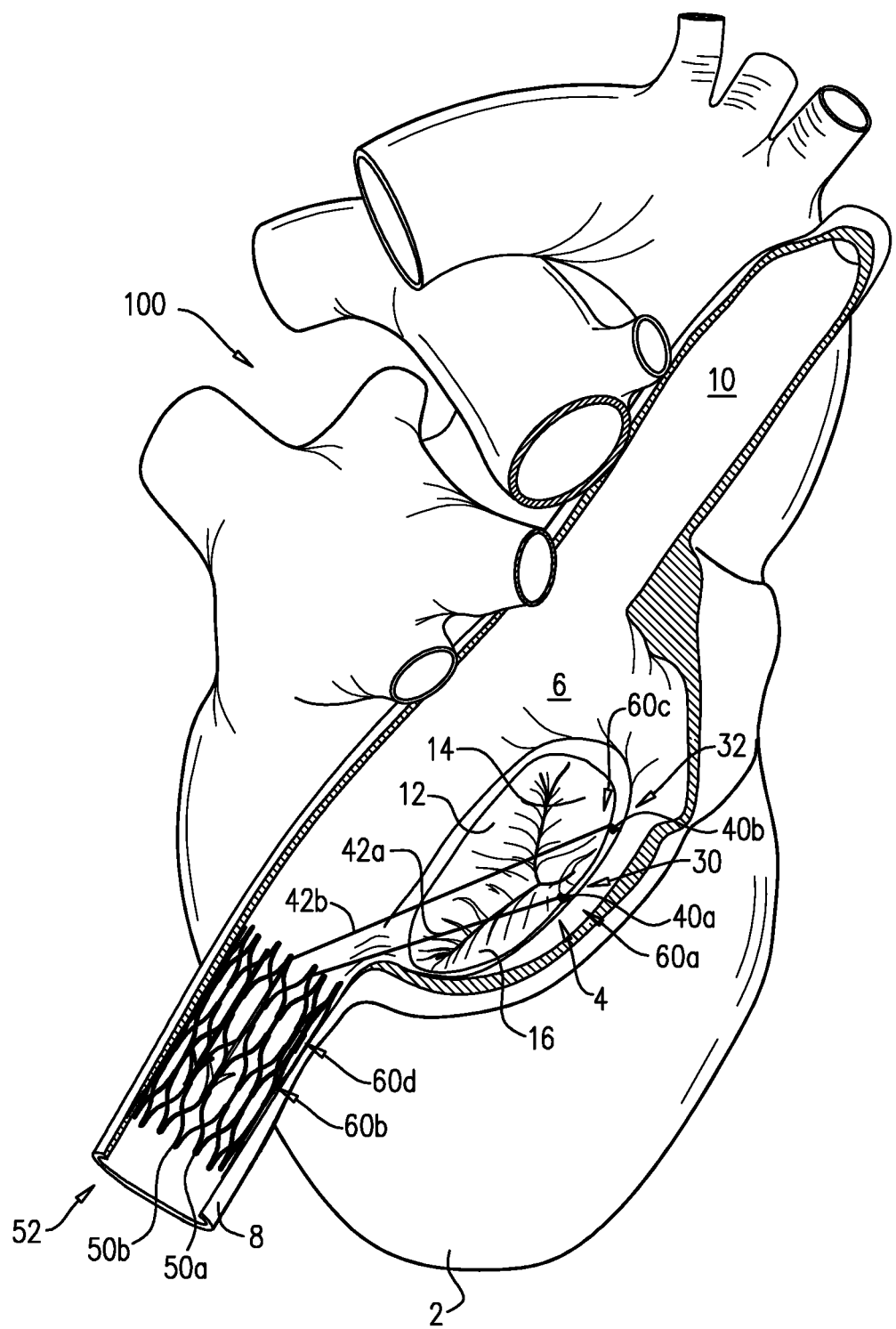

FIGS. 2A-B show a system 100 for repairing tricuspid valve 4 comprising first and second stents 50a and 50b, first and second longitudinal members 42a and 42b, and first and second tissue anchors 40a and 40b. First tissue anchor 40a defines first tissue-engaging element 60a. First stent 50a defines second tissue-engaging element 60b. Second tissue anchor 40b defines a third tissue-engaging element 60c. Second stent 50b defines a fourth tissue-engaging element 60d. For some applications of the present invention, following the implantation of first tissue-engaging element 60a and second tissue-engaging element 60b, such as described hereinabove with reference to FIGS. 1A-G, third and fourth tissue-engaging elements 60c and 60d are then implanted. As described hereinabove, first implantation site 30, as shown, comprises a portion of tissue that is in a vicinity of the commissure between anterior leaflet 14 and posterior leaflet 16. First implantation site 30 may comprise a portion of tissue that is between (1) the middle of the junction between the annulus and anterior leaflet 14, and (2) the middle of the junction between the annulus and posterior leaflet 16.

Following the implantation of first and second tissue-engaging elements 60a and 60b, catheter 22 is retracted from the body of the patient. Outside the body of the patient, catheter 22 is reloaded with third and fourth tissue-engaging elements 60c and 60d. Catheter 22 is then reintroduced within the body of the patient and is advanced toward right atrium 6, as shown in FIG. 2A, such that distal end 23 thereof passes through first stent 50a and toward atrium 6. It is to be noted that a proximal end portion of longitudinal member 42a is coupled to second tissue-engaging element 60b and is not disposed within catheter 22.

Subsequently, a second tissue anchor 40b (i.e., an anchor that is similar to tissue anchor 40a, as described hereinabove) is implanted at a second portion of cardiac tissue at a third implantation site 32. Third implantation site 32 includes a portion of cardiac tissue in the vicinity of tricuspid valve 4 (e.g., a second portion of tissue of the annulus of tricuspid valve 4, as shown). Third implantation site 32, as shown, comprises a portion of tissue that is between (1) the middle of the junction between the annulus and anterior leaflet 14, and (2) the middle of the junction between the annulus and posterior leaflet 16. For some applications, third implantation site 32 may comprise a second portion of the wall that defines right atrium 6. For other applications, third implantation site 32 may comprise a portion of cardiac tissue in the right ventricle, e.g., a portion of the wall that defines the right ventricle, a ventricular portion of the annulus of valve 4, or a portion of a papillary muscle of the right ventricle.

Following implantation of third tissue-engaging element 60c, catheter 22 is retracted and tension is applied to third tissue-engaging element 60c in a manner as described hereinabove with reference to FIGS. 1C-D with regard to the application of tension to implantation site 30. Additionally, tension is applied to a second longitudinal member 42b which couples third and fourth tissue-engaging elements 60c and 60d, e.g., in a manner as described hereinabove with regard to the pulling of first longitudinal member 42a, with reference to FIG. 1C. As described herein, a level of regurgitation of valve 4 may be monitored during the pulling of third implantation site 32 toward second implantation site 52 and of second longitudinal member 42b.

Additionally, responsively to the pulling of tissue at first and third implantation sites 30 and 32 toward second implantation site 52, anterior leaflet 14 is drawn toward septal leaflet 12, and bicuspidization is achieved. Also, responsively to the pulling, a portion of tissue that is between first and third implantation sites 30 and 32 is cinched.

Reference is now made to FIG. 2B. Once the physician determines that the regurgitation of valve 4 is reduced or ceases, and valve 4 has been repaired, catheter 22 is decoupled from fourth tissue-engaging element 60d and/or from second longitudinal member 42b, and the physician retracts catheter 22 in order to expose fourth tissue-engaging element 60d, i.e., second stent 50b, as shown. During the advancement of catheter 22 toward atrium 6, second stent 50b is disposed within a distal portion of catheter 22 in a compressed state. Following initial retracting of catheter 22, second stent 50b is exposed and is allowed to expand within a lumen of first stent 50a, as shown, in order to contact a wall of inferior vena cava 8. Responsively to the expanding, second stent 50b is implanted in second implantation site 52 and maintains the tension of second longitudinal member 42b on second tissue anchor 40b and thereby on the portion of cardiac tissue to which anchor 40b is coupled.

It is to be noted that second stent 50b is implanted within the lumen of first stent 50a by way of illustration and not limitation, and that for some applications of the present invention, first and second stents 50a and 60b may be implanted coaxially at second implantation site 52.

It is to be noted that third and fourth tissue-engaging elements 60c and 60d and second longitudinal member 42b are typically fabricated from the same material, e.g., nitinol, from a single piece. That is, third and fourth tissue-engaging elements 60c and 60d and second longitudinal member 42b typically define a single continuous implant unit.

Figure 3A:
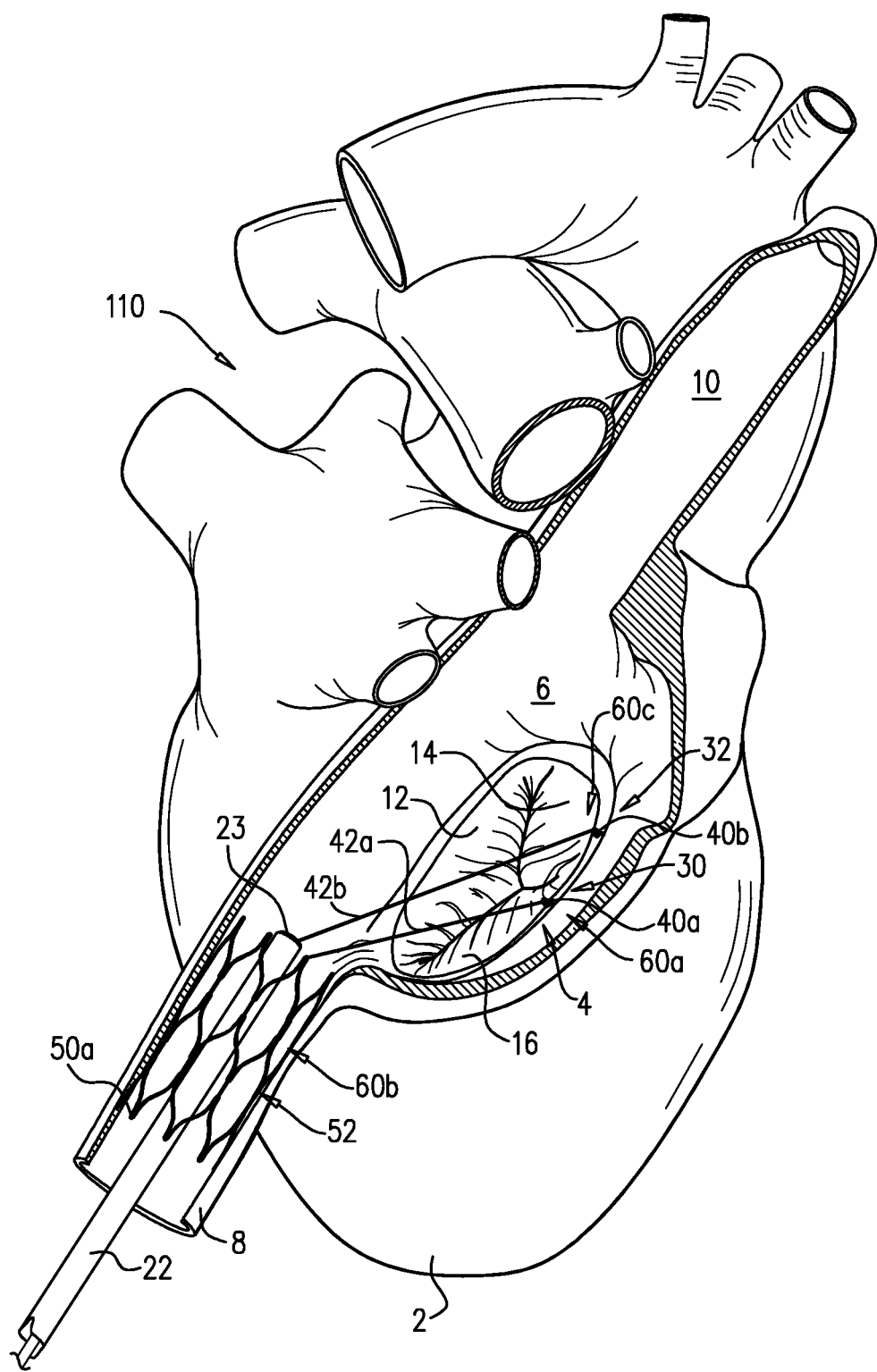
Figure 3B:
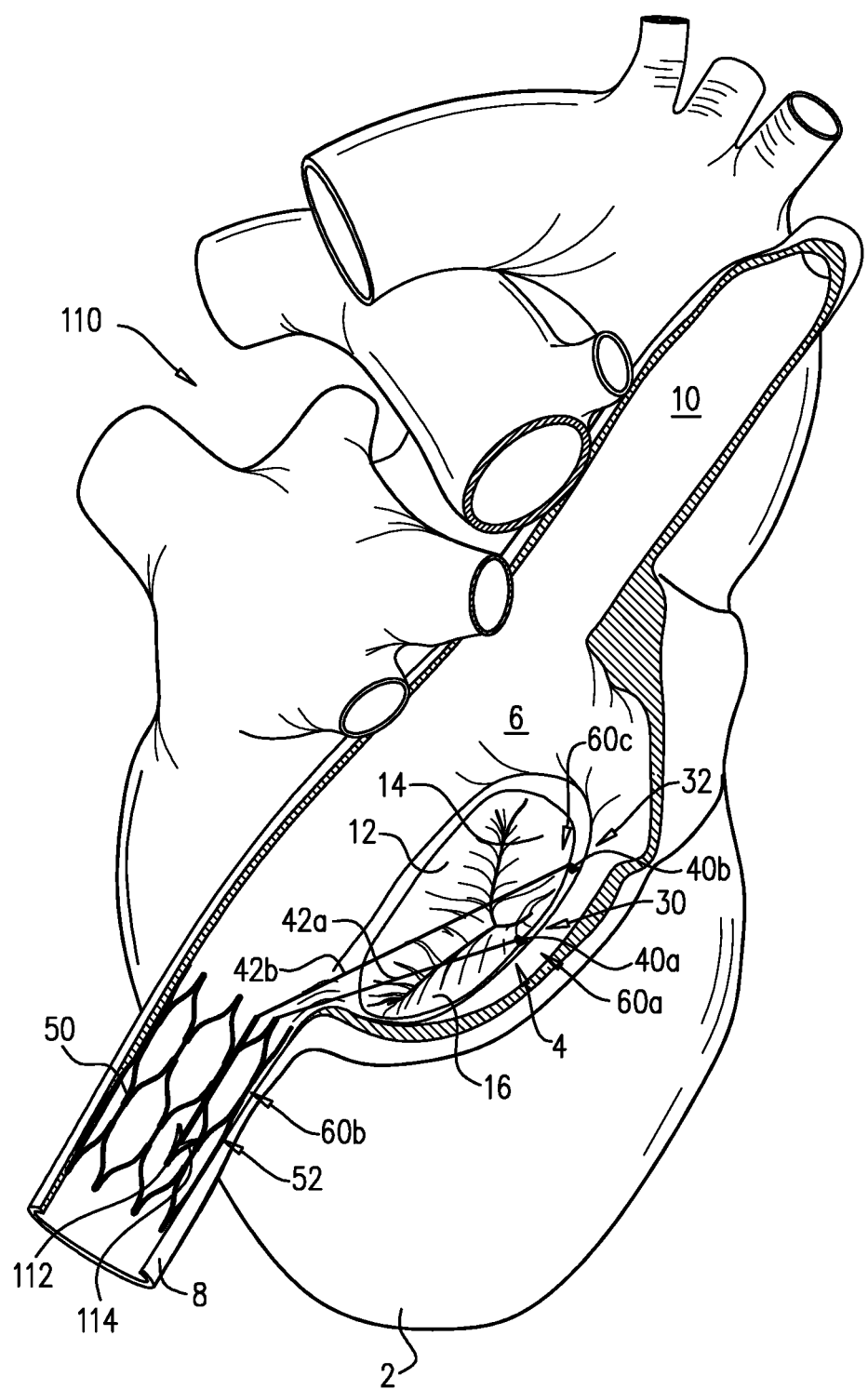

Reference is now made to FIGS. 3A-C, which are schematic illustrations of a system 110 for repairing tricuspid valve 4, which comprises first, second, and third tissue-engaging elements 60a, 60b, and 60c, and first and second longitudinal members 42a and 42b, in accordance with some applications of the present invention. System 110 is similar to system 100 described hereinabove with reference to FIGS. 2A-B, with the exception that system 110 does not comprise second stent 50*b*; rather, as shown in FIGS. 3B-C, a proximal end portion 112 of second longitudinal member 42*b* is shaped so as to define one or more engaging elements 114 (e.g., hooks or barbs, as shown). Following the implanting of third tissue-engaging element 60*c* and the subsequent pulling of second longitudinal member 42*b*, catheter 22 facilitates coupling of engaging elements 114 with the struts of stent 50 (as shown in FIG. 3C which is an enlarged image of stent 50 and the proximal portion of second longitudinal member 42*b* of FIG. 3B). The coupling of engaging elements 114 to stent 50 maintains the tension applied to longitudinal member 42, and thereby maintains the tension on third tissue-engaging element 60*c* in order to maintain the remodeled state of tricuspid valve 4.

It is to be noted that third tissue-engaging element 60*c*, second longitudinal member 42*b*, and engaging elements 114 and proximal end portion 112 of second longitudinal member 42*b* are typically fabricated from the same material, e.g., nitinol, from a single piece. That is, third tissue-engaging element 60*c*, second longitudinal member 42*b*, and engaging elements 114 and proximal end portion 112 of second longitudinal member 42*b* typically define a single continuous implant unit.

Reference is now made to FIGS. 2A-B and 3A-C. For some applications, following the implantation the tissue-engaging elements at their respective implantation sites, as described hereinabove, a length of each one of first and second longitudinal members 42*a* and 42*b* is adjusted by an adjustable mechanism, as described hereinbelow with reference to FIGS. 5A-B or 5C. Adjusting mechanism 150 typically comprises a mechanical element which shortens a length of each one of first and second longitudinal members 42*a* and 42*b*. For some applications, a respective adjustable mechanism 150 may be permanently coupled to each one of first and second longitudinal members 42*a* and 42*b* (not shown); each mechanism 150 comprises an adjusting element, e.g., a spool for looping respective portions of longitudinal members 42*a* and 42*b* therearound, a crimping bead for crimping and shortening respective portions of longitudinal members 42*a* and 42*b*, a ratchet element, or a deforming element which deforms respective portions of longitudinal members 42*a* and 42*b*. For other applications, adjusting mechanism 150 comprises only adjusting tool 144, as shown in FIG. 5A. In such applications, adjusting tool 144 may comprise an adjusting element, e.g., a crimping bead for crimping and shortening respective portions of longitudinal members 42*a* and 42*b*, or a deforming element which deforms respective portions of longitudinal members 42*a* and 42*b*. In either application, a level of regurgitation of valve 4 may be monitored during the adjusting of the respective lengths of first and second longitudinal members 42*a* and 42*b*.

Figure 4A:
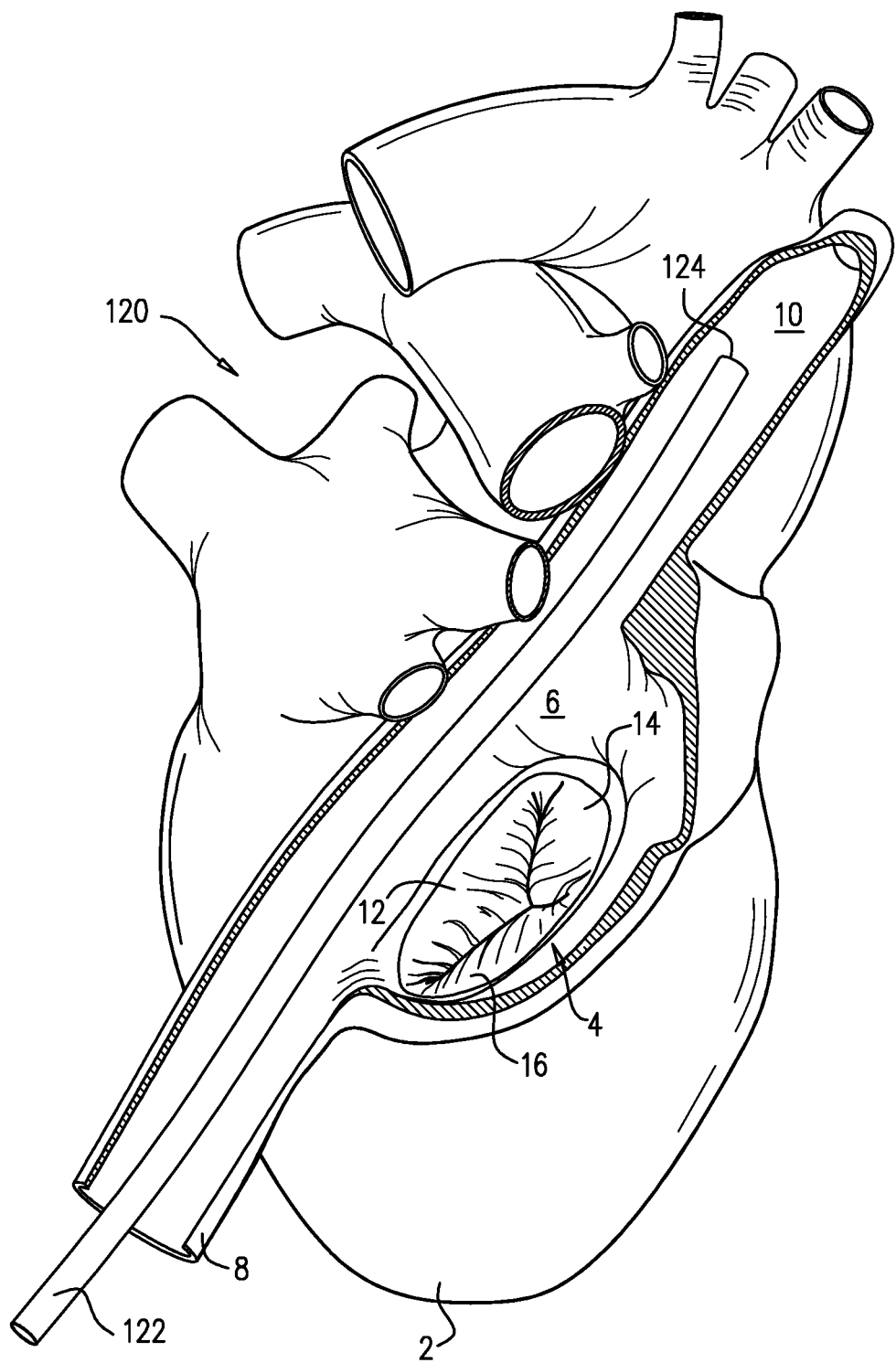
FIGS. 4A-C are schematic illustrations of apparatus for reducing regurgitation of a tricuspid valve which comprises first and second stents and first and a tensioning element that couples the first and second stents, in accordance with some applications of the present invention.
Figure 4B:
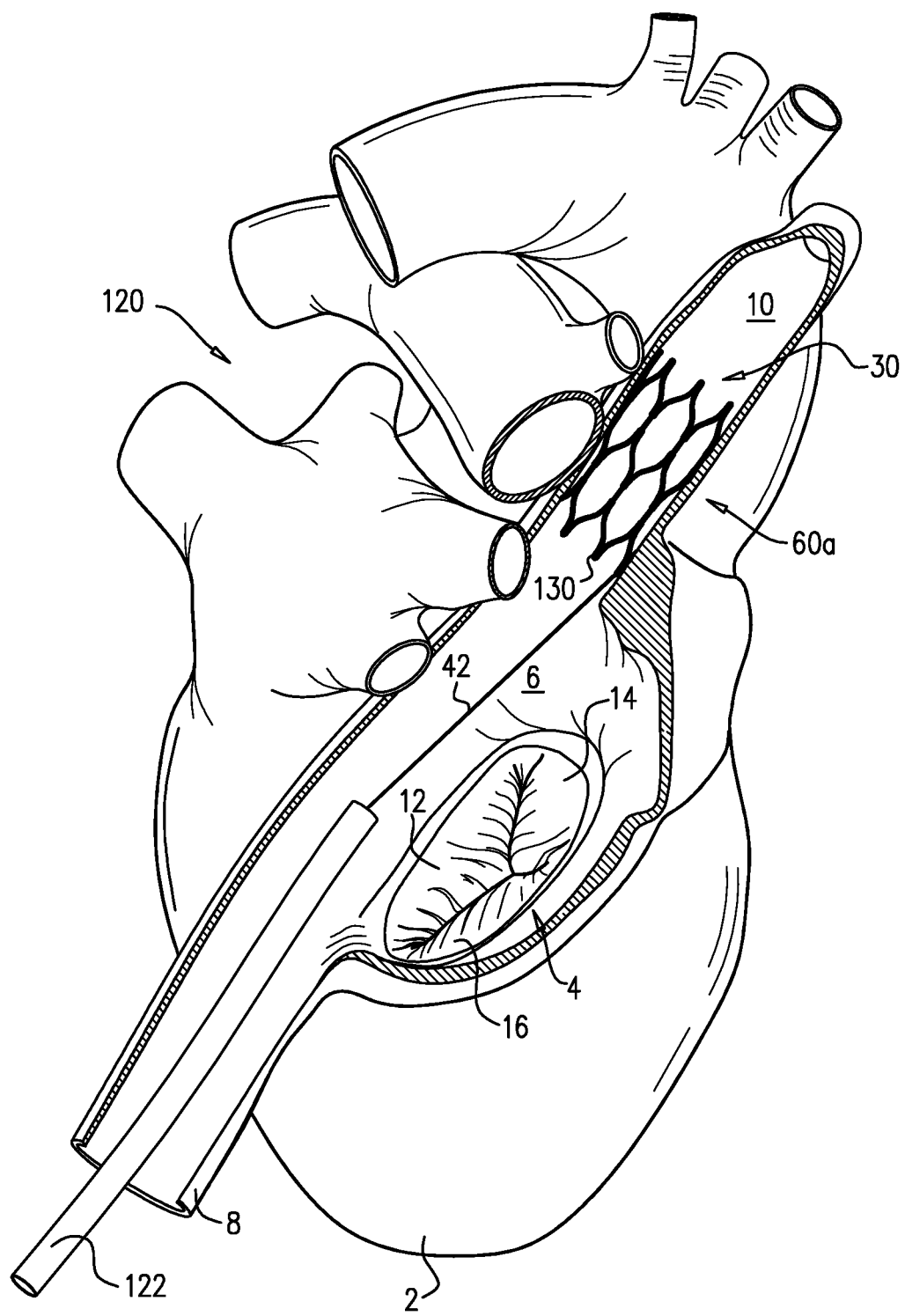
Figure 4C:
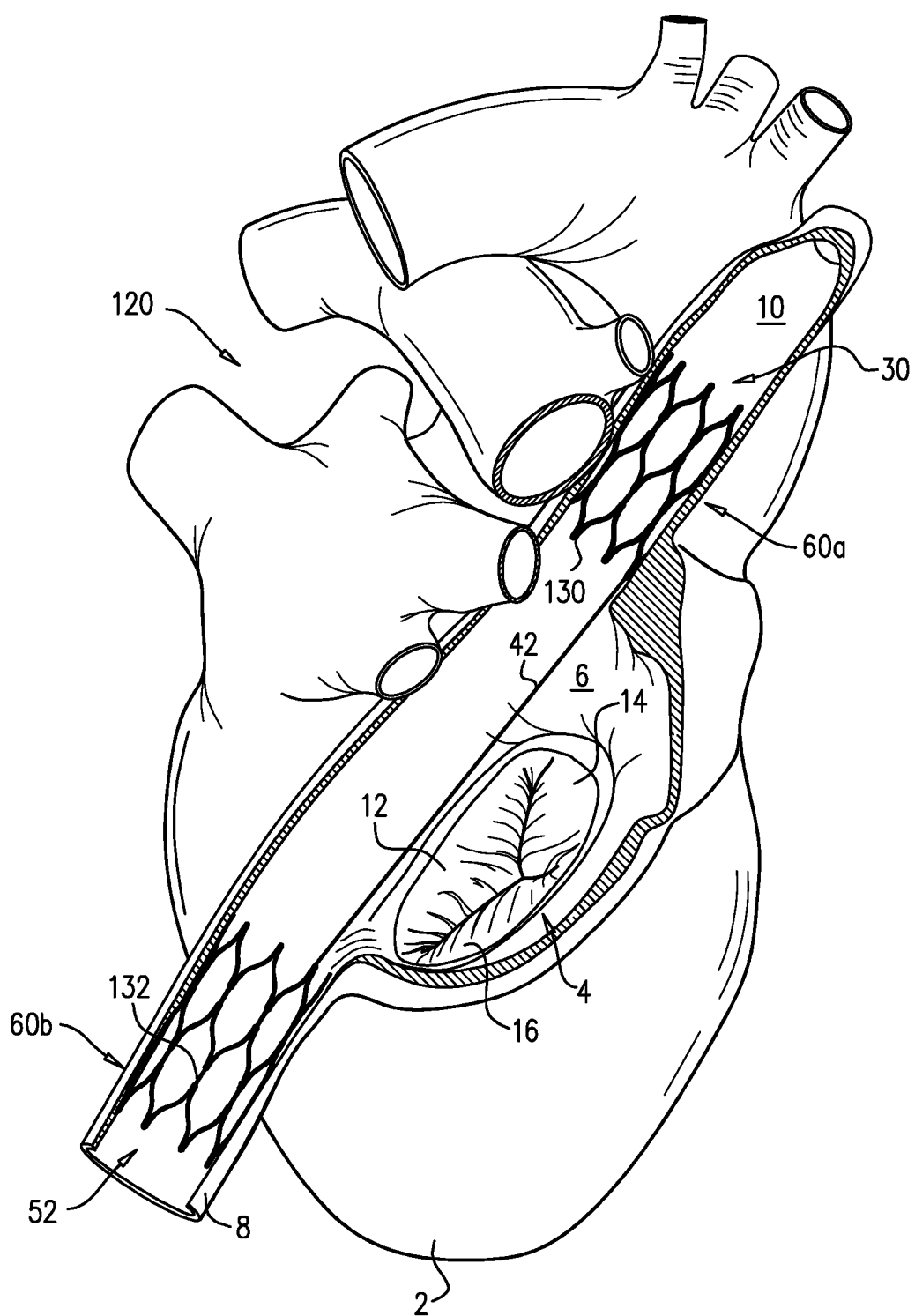

FIGS. 4A-C show a system 120 for repairing tricuspid valve 4 comprising first and second stents 130 and 132 implanted in superior vena cava 10 and inferior vena cava, respectively, in accordance with some applications of the present invention. A catheter 122 is advanced through vasculature of the patient such that a distal end 124 of catheter 122 toward superior vena cava 10, as shown in FIG. 4A. Catheter 122 is advanced from a suitable access location, e.g., catheter 122 may be introduced into the femoral vein of the patient, through inferior vena cava 8, and toward superior vena cava 10. During the advancement of catheter 122 toward superior vena cava 10 and inferior vena cava 8, stents 130 and 132 are disposed within a distal portion of catheter 122 in a compressed state.

In FIG. 4B, first stent 130 is deployed from within catheter 122 and expands to contact tissue of a wall of superior vena cava 10. This portion of the wall of the superior vena cava defines first implantation site 30 in such applications of the present invention. Additionally, first stent 130 defines first tissue-engaging element 60*a* in such applications of the present invention. It is to be noted that the portion of superior vena cava 10 in which stent 130 is implanted defines a portion of tissue that is in the vicinity of valve 4.

Catheter 122 is then retracted so as to pull and apply tension to longitudinal member 42. Longitudinal member 42 is pulled directly by catheter 122 and/or indirectly by pulling stent 132 disposed within catheter 122. For some applications, during the pulling, a level of regurgitation of tricuspid valve 4 may be monitored, because responsively to the pulling, the geometry of the wall of atrium 6 is altered and the leaflets of tricuspid valve 4 are drawn together so as to reduce and eliminate regurgitation of valve 4.

Once the physician determines that the regurgitation of valve 4 is reduced or ceases, and valve 4 has been repaired, the physician decouples catheter 122 from second stent 132 disposed therein and/or from longitudinal member 42, and then retracts catheter 122 in order to expose second tissue-engaging element 60*b*, i.e., second stent 132, as shown. Following initial retracting of catheter 122, second stent 132 is exposed and is allowed to expand and contact a wall of interior vena cava 8, as shown in FIG. 4C. Responsively to the expanding, second stent 132 is implanted in second implantation site 52 and maintains the tension of longitudinal member 42 on first stent 130 and thereby maintains the altered geometry of the wall of atrium 6 and of the leaflets of tricuspid valve 4.

Reference is again made to FIGS. 4A-C. For some applications, following the deploying of first and second tissue-engaging elements 60*a* and 60*b* (i.e., first and second stents 130 and 132, respectively), a distance between first and second tissue-engaging elements 60*a* and 60*b* is adjusted by an adjustable mechanism, as described hereinbelow with reference to FIGS. 5A-B or 5C. In such applications, a length of longitudinal member 42 between first and second stents 130 and 132 may be adjusted by an adjusting mechanism 150, as shown in FIGS. 5A-B or 5C. Adjusting mechanism 150 typically comprises a mechanical element which shortens a distance of longitudinal member 42 between first and second stents 130 and 132. For some applications, adjustable mechanism 150 may be permanently coupled to longitudinal member 42 (not shown) and comprises an adjusting element, e.g., a spool for looping portions of longitudinal member 42 therearound, a crimping bead for crimping and shortening a portion of longitudinal member 42, a ratchet element, or a deforming element which deforms a portion of longitudinal member 42 in order to shorten its length between first and second stents 130 and 132. For other applications, adjusting mechanism 150 comprises only adjusting tool 144, as shown in FIG. 5A. In such applications, adjusting tool 144 may comprise an adjusting element, e.g., a crimping bead for crimping and shortening a portion of longitudinal member 42, or a deforming element which deforms a portion of longitudinal member 42 in order to shorten its length between first and second stents 130 and 132. In either application, a level of regurgitation of valve 4 may be monitored during the adjusting of the distance between first and second tissue-engaging elements 60a and 60b by adjusting mechanism 150.

It is to be noted that first and second stents 130 and 132 and longitudinal member 42 are typically fabricated from the same material, e.g., nitinol, from a single piece. That is, first and second stents 130 and 132 and longitudinal member 42 typically define a single continuous implant unit.

Reference is yet again made to FIGS. 4A-C. It is to be noted that distal end 124 of catheter 122 may first be advanced toward inferior vena cava, and not first toward superior vena cava, as shown in FIG. 4A. In such an embodiment, catheter 122 may be introduced into the external jugular vein, through the subclavian vein, through superior vena cava 10, and toward inferior vena cava 8. Alternatively, catheter 122 may be introduced into the basilic vein, through the subclavian vein, through superior vena cava 10 and toward interior vena cava 8. It is to be noted that any suitable access location may be used to introduce catheter 122 into the vasculature of the patient.

Reference is still made to FIGS. 4A-C. For some applications, one or both of stents 130 and/or 132 comprise a plurality of interconnected superelastic metallic struts, such as described hereinabove with reference to FIG. 1D. Alternatively or additionally, for some applications, one or both of stents 130 and/or 132 comprise two or more rings 62, configured as described hereinabove with reference to FIGS. 1E-G.

Reference is now made to FIGS. 5A-B, which are schematic illustrations of a system 140 for repairing tricuspid valve 4 comprising first and second tissue anchors 40a and 40b coupled together by longitudinal member 42, in accordance with some applications of the present invention. In such applications, first tissue anchor 40a defines first tissue-engaging element 60a, and second tissue anchor 40b defines second tissue-engaging element 60b. Tissue anchors 40a and 40b may comprise any suitable anchor for puncturing, squeezing, or otherwise engaging cardiac tissue of the patient. As shown by way of illustration and not limitation, tissue anchors 40a and 40b comprise helical tissue anchors which puncture and screw into the cardiac tissue. It is to be noted that first and second tissue-engaging elements 60a and 60b (i.e., first and second tissue anchors 40a and 40b) and longitudinal member 42 are fabricated from the same material, e.g., nitinol, from a single piece. That is, first and second tissue-engaging elements 60a and 60b and longitudinal member 42 define a single continuous implant unit.

Catheter 142 is advanced through vasculature of the patient, in manner as described hereinabove with regard to catheter 22 with reference to FIG. 1A. Catheter 142 is advanced toward first implantation site 30 and facilitates implantation of first tissue anchor 40a in the cardiac tissue. As shown, first implantation site 30 includes a first portion of tissue of the annulus of valve 4 at the mural side of valve 4, by way of illustration and not limitation. For some applications, first implantation site 30 may include a first portion of the wall of atrium 6 of heart 2. As shown by way of illustration and not limitation, first implantation site 30 includes a portion of tissue of the annulus at the commissure between anterior leaflet 14 and posterior leaflet 16. It is to be noted that first implantation site 30 may be implanted at any suitable location along and in the vicinity of the annulus of valve 4.

Catheter 142 is then advanced toward second implantation site 52 and facilitates implantation of second tissue anchor 40b in the cardiac tissue. For some applications, as catheter 142 is advanced toward second implantation site, longitudinal member 42 is pulled to draw together the leaflets of valve 4, while a level of regurgitation of valve 4 is monitored. As shown, second implantation site 52 includes a second portion of tissue of the annulus of valve 4 at the septal side of valve 4, by way of illustration and not limitation. For some applications, second implantation site 52 may include a second portion of the wall of atrium 6 of heart 2. As shown by way of illustration and not limitation, second implantation site 52 includes a portion of tissue of the annulus inferior of the middle of septal leaflet 12. It is to be noted that first implantation site 30 may be implanted at any suitable location along and in the vicinity of the annulus of valve 4, e.g., at the commissure between posterior leaflet 16 and septal leaflet 12.

For such an application, by applying tension to longitudinal member 42, anterior leaflet 14 and septal leaflet 12 are drawn together, and bicuspidization of valve 4 is achieved. For some applications, during the adjusting of mechanism 150, a retrievable stent may be deployed in inferior vena cava 8 so as to stabilize system 140 during the adjusting of adjusting mechanism 150. It is to be further noted that tissue-engaging elements 60a and 60b and catheter 142 may be advanced toward atrium 6 through superior vena cava, mutatis mutandis.

For some applications of the present invention, system 140 comprises one or more anchor-manipulating tools (not shown for clarity of illustration), that is slidably disposed within catheter 142. The anchor-manipulating tool is slid distally with within catheter 142 so as to push distally tissue anchors 40a and 40b and expose tissue anchors 40a and 40b from within catheter 142. For some applications of the present invention, the anchor-manipulating tool(s) (is/are) reversibly couplable to anchors 40a and 40b, and facilitate(s) implantation of anchors 40a and 40b in the cardiac tissue. For applications in which anchors 40a and 40b comprises respective helical tissue anchor, as shown, the operating physician rotates the anchor-manipulating tool(s) from a site outside the body of the patient in order to rotate anchors 40a and 40b, and thereby screw at least respective distal portions of anchors 40a and 40b in the cardiac tissue.

Reference is again made to FIGS. 5A-B. It is to be noted that first and second implantation sites 30 and 52 include cardiac tissue that is upstream of valve 4 by way of illustration and not limitation, and that either or both first and second implantation sites may include cardiac tissue that is downstream of valve 4.

Typically, following implantation of first and second tissue anchors 40a and 40b, a length of longitudinal member 42, that is disposed between first and second tissue anchors 40a and 40b, is adjusted by adjusting mechanism 150. Adjusting mechanism 150 typically comprises a mechanical element which shortens a distance of longitudinal member 42 between first and second tissue-engaging elements 60a and 60b. For some applications, adjustable mechanism 150 may be permanently coupled to longitudinal member 42 (as shown in FIG. 5B) and comprises an adjusting element, e.g., a spool for looping portions of longitudinal member 42 therearound, a crimping bead for crimping and shortening a portion of longitudinal member 42, a ratchet element, or a deforming element which deforms a portion of longitudinal member 42 in order to shorten its length between first and second tissue-engaging elements 60a and 60b.

For other applications, adjusting mechanism 150 comprises only adjusting tool 144, as shown in FIG. 5A. In such applications, adjusting tool 144 may comprise an adjusting element, e.g., a crimping bead for crimping and shortening a portion of longitudinal member 42, or a deforming element which deforms a portion of longitudinal member 42 in order to shorten its length between first and second tissue-engaging elements 60a and 60b.

In either application, a level of regurgitation of valve 4 may be monitored during the adjusting of the distance between first and second tissue-engaging elements 60a and 60b by adjusting mechanism 150.

Following the adjusting of the distance between first and second implantation sites 30 and 52, adjusting tool 144 and catheter 142 are decoupled from longitudinal member 42 and are extracted from the body of the patient.

Reference is now made to FIG. 5C, which is a schematic illustration of another configuration of system 140, in accordance with some applications of the present invention. This configuration of system 140 is generally similar to the configuration described above with reference to FIGS. 5A-B, except that the system comprises a third tissue-engaging element 60c (i.e., a third tissue anchor), in addition to first and second tissue-engaging elements 60a and 60b. Third tissue-engaging element 60c is implanted at third implantation site 32, such as using the techniques described hereinabove with reference to FIGS. 5A-B. For some applications, third implantation site 32 may include a third portion of the wall of atrium 6. By way of illustration and not limitation, the three implantation sites may include portions of tissue of the annulus of the three leaflets of the valve, such as at the middle of the leaflets.

Tissue-engaging elements 60a, 60b, and 60c are coupled to longitudinal members 42a, 42b, and 42c, respectively. The longitudinal members are coupled together by adjusting mechanism 150. For some applications, adjusting mechanism 150 comprises a spool for looping portions of the longitudinal members therearound, and a ratchet element which allows the spool to rotate in only one direction. Rotation of the spool loops the longitudinal member therearound, thereby shortening the effective lengths of the members and applying tension thereto, to draw the leaflets toward one another, such as described hereinabove with reference to FIGS. 5A-B. As a result, a geometry of the wall of the right atrium may be altered.

Figure 6:
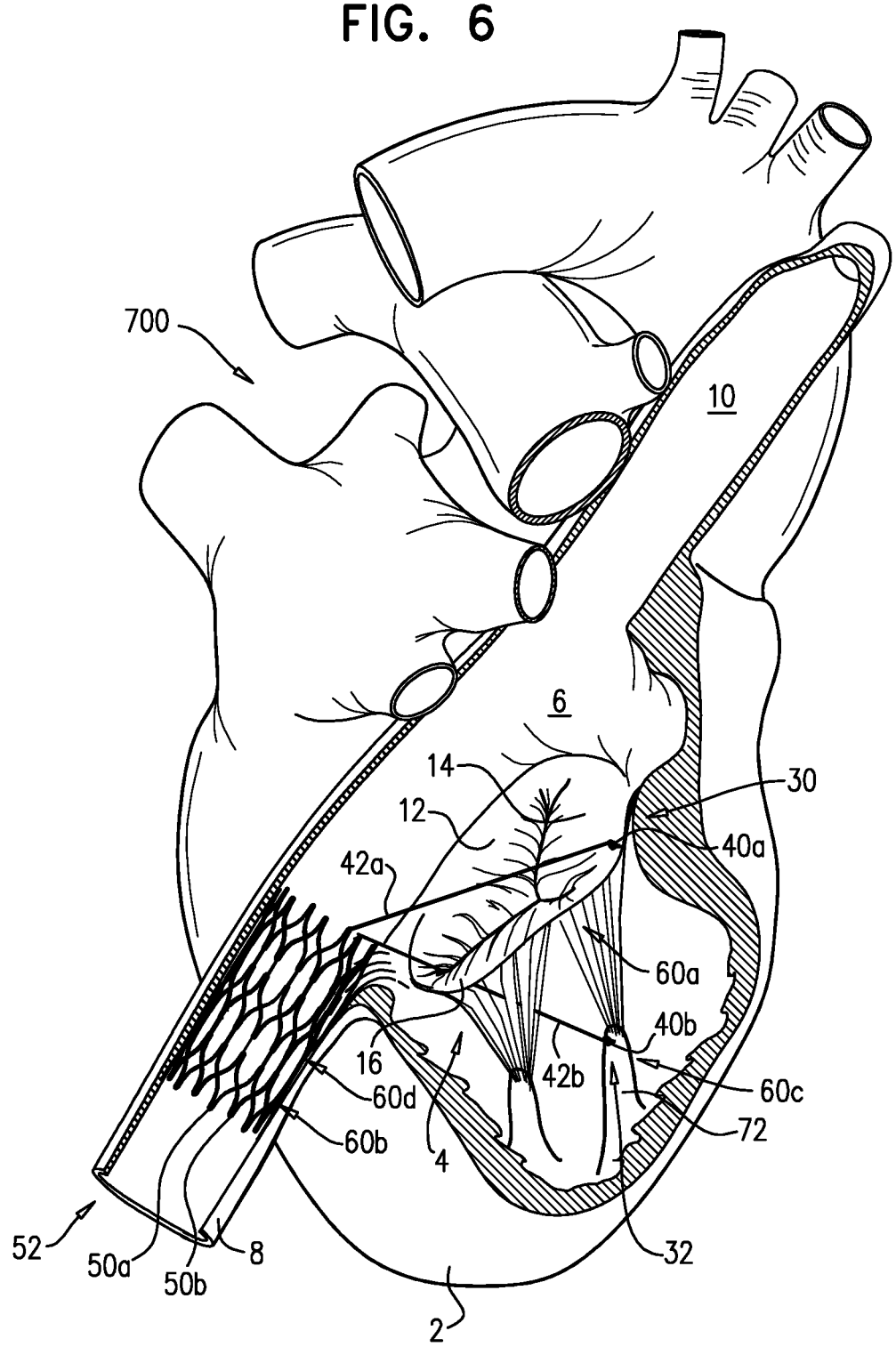
FIG. 6 is a schematic illustration of apparatus for reducing regurgitation of the heart valve which comprises a first anchoring system in the inferior vena cava, a first tissue anchor implanted at the valve, and a second tissue anchor implanted in the papillary muscle.

Reference is now made to FIG. 6 which is a schematic illustration of a system 700 for repairing tricuspid valve 4 comprising first tissue-engaging element 60a implanted at a portion of the annuls of valve 4 and a third tissue-engaging element 60c implanted at a portion of a papillary muscle 72 in the right ventricle of the patient, in accordance with some applications of the present invention. It is to be noted that third implantation site 32 comprises papillary muscle 72 by way of illustration and not limitation, and that third implantation site 32 may comprise any potion of a wall of the right ventricle (e.g., a portion of tissue of the annulus at the ventricular surface of valve 4, a portion of the wall of the ventricle in the vicinity of valve 4, a portion of tissue in the vicinity of the apex of heart 2, or any other suitable portion of the wall of the ventricle).

Reference is now made to FIGS. 2A-B and 6. First, second, and third tissue-engaging elements 60a-c of FIG. 6 are implanted in cardiac tissue in a manner as described hereinabove with reference to FIGS. 2A-B, with the exception that, in order to implant third tissue-engaging element 60c, catheter 22 passes through the leaflets of valve 4 into the right ventricle and implants third tissue-engaging element 60c in tissue of the ventricle. Following coupled of third tissue-engaging element 60c in FIG. 6, second stent 50b is deployed in second implantation site 52 in interior vena cava 8, as described hereinabove with reference to FIG. 2B.

Reference is now made to FIGS. 3A-C and 6. It is to be noted, that for some applications, second longitudinal member 42b is coupled at a proximal end thereof to one or more barbs 114 (i.e., and is not connected to second stent 50, as shown). Barbs 114 enable second longitudinal member 42b to be coupled to stent 50 that is in connection with first longitudinal member 42a, and thereby maintain tension on third implantation site 32 and maintain coaptation of at least anterior leaflet 14 and septal leaflet 12.

Reference is again made to FIG. 6. Such an application of at least one tissue-engaging element 60 in a portion of tissue of the ventricle of heart 2, in some applications, facilitates independent adjustment of valve 4 and a portion of the ventricle wall of heart 2. That is, for some application, geometric adjustment of the right ventricle to improve its function is achieved.

For some applications, following the deploying of first, second, third, and fourth tissue-engaging elements 60a-d (i.e., first and second anchors 40a and 40b, and first and second stents 50a and 50b), (1) a distance between first and second tissue-engaging elements 60a and 60b is adjustable by first adjustable mechanism, and (2) a distance between third and fourth tissue-engaging elements 60c and 60d is adjustable by a second adjustable mechanism, as described hereinbelow with reference to FIGS. 5A-B or 5C. In such applications, (1) a length of first longitudinal member 42a between first and second tissue-engaging elements 60a and 60b may be adjusted by a first adjusting mechanism 150, as shown in FIGS. 5A-B or 5C, and (2) a length of second longitudinal member 42b between third and fourth tissue-engaging elements 60c and 60d may be adjusted by a second adjusting mechanism 150, as shown in FIGS. 5A-B or 5C. Adjusting mechanisms 150 typically each comprise a mechanical element which shortens a distance of respective longitudinal members 42.a and 42b. For some applications, adjustable mechanisms 150 may be permanently coupled to respective longitudinal members 42a and 42b (not shown) and each comprise an adjusting element, e.g., a spool for looping portions of longitudinal members 42a and 42b therearound, a crimping bead for crimping and shortening respective portions of longitudinal members 42a and 42b, a ratchet element, or a deforming element which deforms respective portions of longitudinal members 42a and 42b in order to shorten its length between the respective tissue-engaging elements 60. For other applications, adjusting mechanisms 150 each comprise only adjusting tool 144, as shown in FIG. 5A. In such applications, adjusting tool 144 may comprise an adjusting element, e.g., a crimping bead for crimping and shortening respective portions of longitudinal members 42a and 42b, or a deforming element which deforms respective portions of longitudinal members 42a and 42b. In either application, a level of regurgitation of valve 4 may be monitored and the adjustment of the geometry of the right ventricle is monitored during (1) the adjusting of the distance between first and second implantation sites 30 and 52, and (2) the adjusting of the distance between third and second implantation sites 32 and 52, respectively.

Reference is now made to FIGS. 8A-E and 9A-E, which are schematic illustrations of a system 800 for repairing tricuspid valve 4, in accordance with respective applications of the present invention. As perhaps best seen in FIGS. 8E and 9E, system 800 comprises first, second, third, and fourth tissue-engaging elements 60a, 60b, 60c, and 60d. System 800 is similar in some respects to system 110 described hereinabove with reference to FIGS. 3A-B, with the exception that system 800 typically comprises only exactly one longitudinal member 42. Typically, longitudinal member 42 is directly coupled to first tissue-engaging element 60a, and indirectly coupled to tissue-engaging elements 60c and 60d by a longitudinal sub-member 802. Typically, one end of longitudinal sub-member 802 is coupled to tissue-engaging element 60c, and the other end of the sub-member is coupled to tissue-engaging element 60d. For some applications, as shown, longitudinal member 42 is not fixed to longitudinal sub-member 802; instead, longitudinal sub-member 802 engages, e.g., is hooked on or looped over, longitudinal member 42, at a junction 804 during deployment of the longitudinal sub-member, as described hereinbelow with reference to FIGS. 8C-E and 9C-E. Alternatively, a ring is provided that couples the longitudinal sub-member to the longitudinal member (configuration not shown).

FIGS. 8A-E illustrate a superior vena cava approach, in which tissue-engaging elements 60a, 60c, and 60d are advanced into atrium 6 via superior vena cava 10, and tissue-engaging element 60b is deployed in the superior vena cava. FIGS. 9A-E illustrate an inferior vena cava approach, in which tissue-engaging elements 60a, 60c, and 60d are advanced into atrium 6 via inferior vena cava 8, and tissue-engaging element 60b is deployed in the inferior vena cava. Typically, one of tissue-engaging elements 60a, 60c, and 60d is deployed at the septal side of tricuspid valve 4 in the caudal part of the base of the septal leaflet, and the other two of tissue-engaging elements 60a, 60c, and 60d are deployed at the mural side of the valve, dividing the entire mural side in three equal spaces, generally at the middle of anterior leaflet and the commissure between the anterior and posterior leaflets. For some applications, yet another tissue-engaging element is deployed at the mural side of the valve (configuration not shown).

Figure 8A:
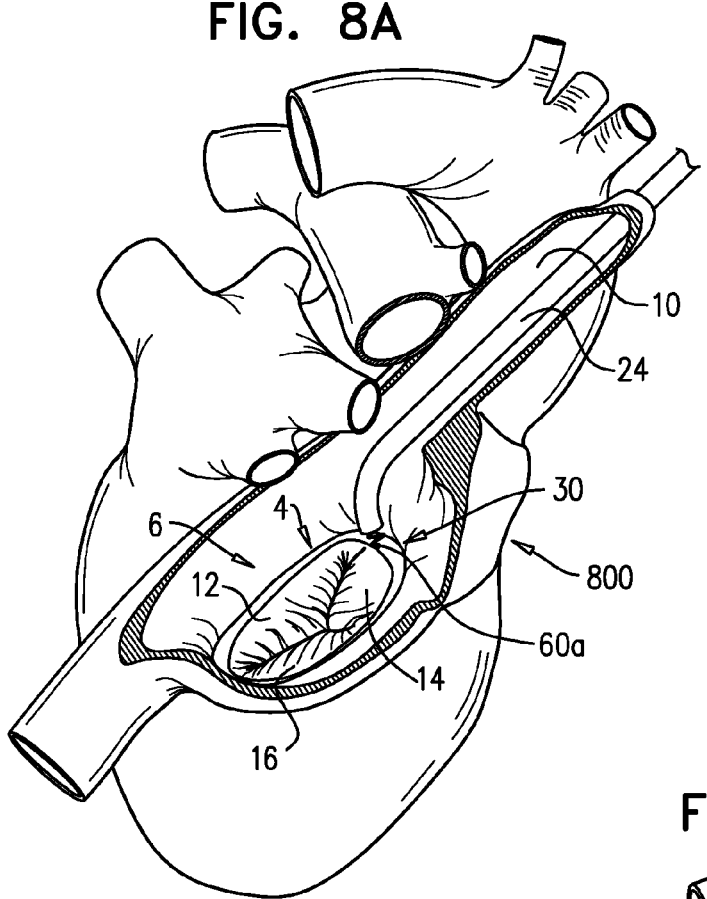
FIGS. 8A-E and 9A-E are schematic illustrations of a system for repairing a tricuspid valve, using a superior vena cava approach and an inferior vena cava approach, respectively, in accordance with respective applications of the present invention.
Figure 9A:
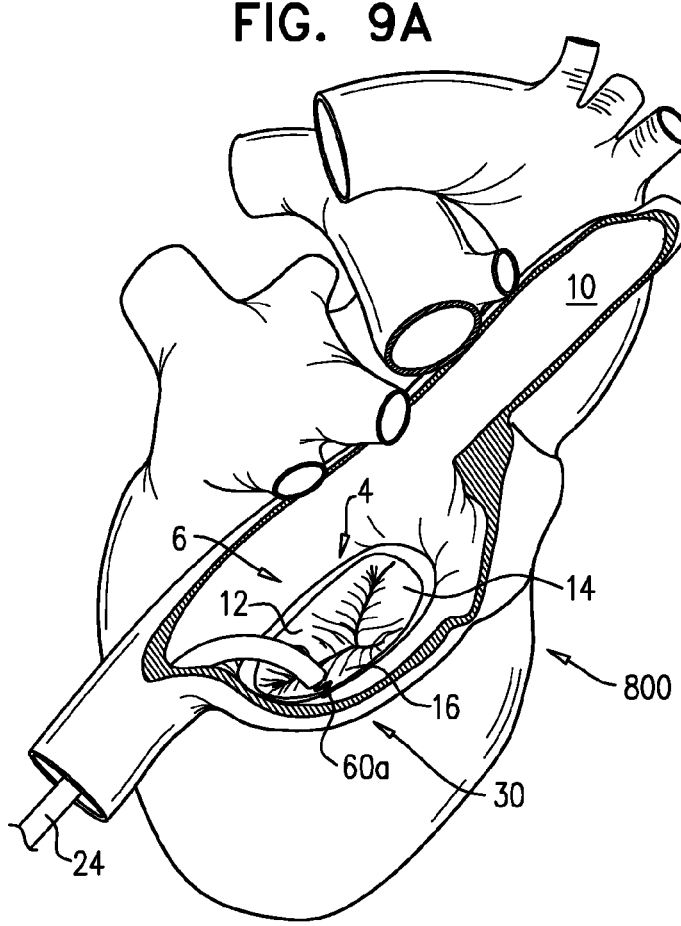

As shown in FIGS. 8A and 9A, anchor-deployment tube 24 is deployed into atrium 6, for example, using techniques described hereinabove with reference to FIG. 1A. First tissue-engaging element 60a is deployed at first implantation site 30, such as using anchoring techniques described herein. First implantation site 30 includes a portion of cardiac tissue in the vicinity of tricuspid valve 4 (e.g., a first portion of tissue of the annulus of tricuspid valve 4, as shown). For example, in the approach shown in FIG. 8A, first implantation site 30 may be on the mural side of the annulus of the valve (e.g., at anterior leaflet 14), approximately centered between two of the commissures of the valve. In the approach shown in FIG. 9A, first implantation site 30 may be on the mural side of the annulus (e.g., at posterior leaflet 16), approximately centered between two of the commissures of the valve. Alternatively, although typically less desirable, first implantation site 30 may be approximately at a commissure of the valve.

Figure 8B:
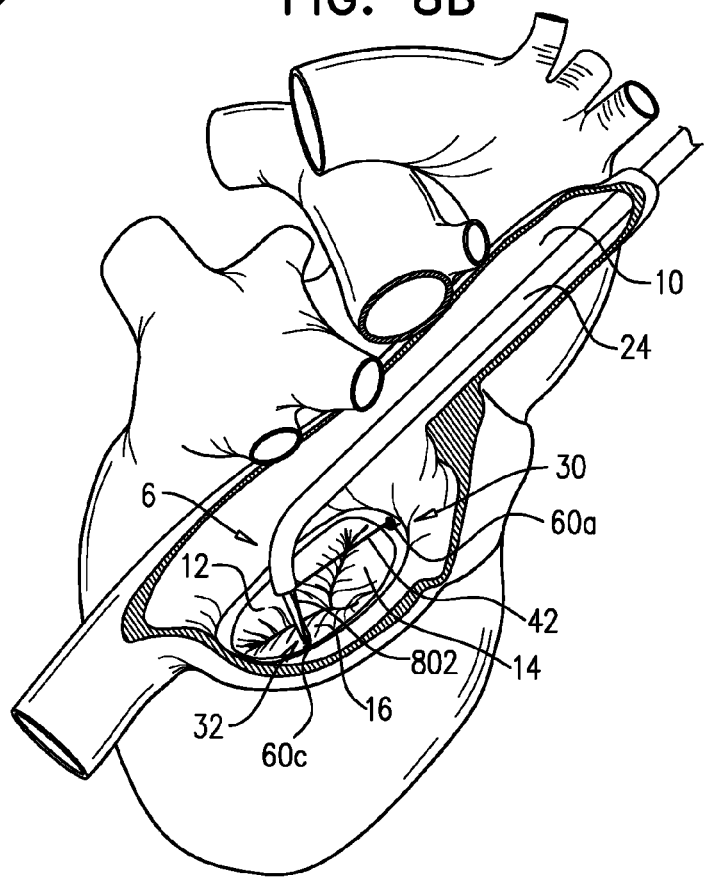
Figure 9B:
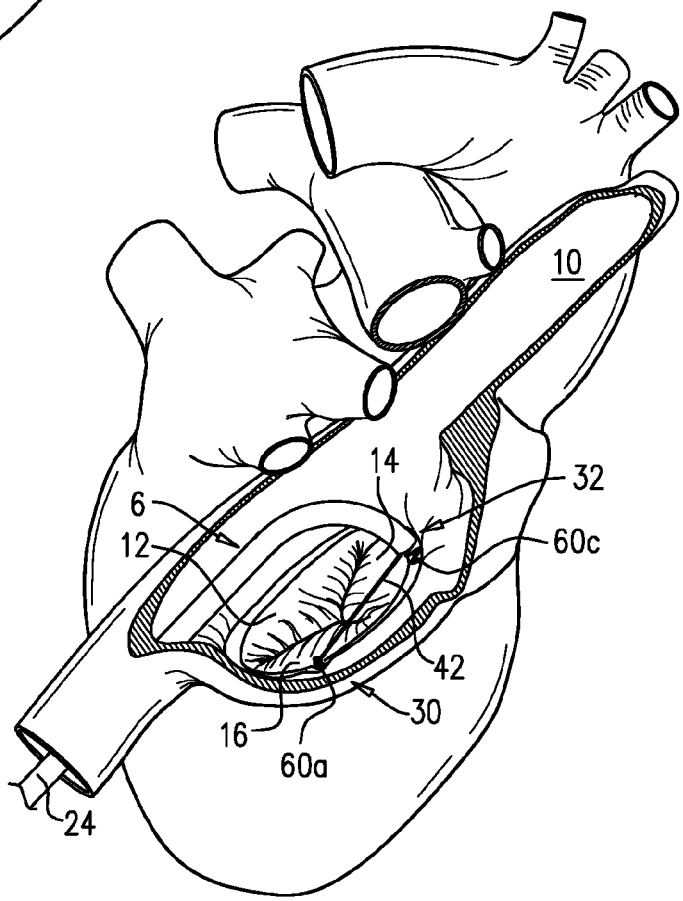

As shown in FIGS. 8B and 9B, the distal end of anchor-deployment tube 24 is advanced to third implantation site 32. Third tissue-engaging element 60c is deployed at third implantation site 32, such as using anchoring techniques described herein. Third implantation site 32 includes a portion of cardiac tissue in the vicinity of tricuspid valve 4 (e.g., a second portion of tissue of the annulus of tricuspid valve 4, as shown). For example, in the approach shown in FIG. 8B, third implantation site 32 may be on the mural side of the annulus of the valve (e.g., at posterior leaflet 16), approximately centered between two of the commissures of the valve. In the approach shown in FIG. 9B, third implantation site 32 may be on the mural side of the annulus of the valve (e.g., at anterior leaflet 14), approximately centered between two of the commissures of the valve. Alternatively, although typically less desirable, third implantation site 32 may be approximately at a commissure of the valve.

Figure 8C:
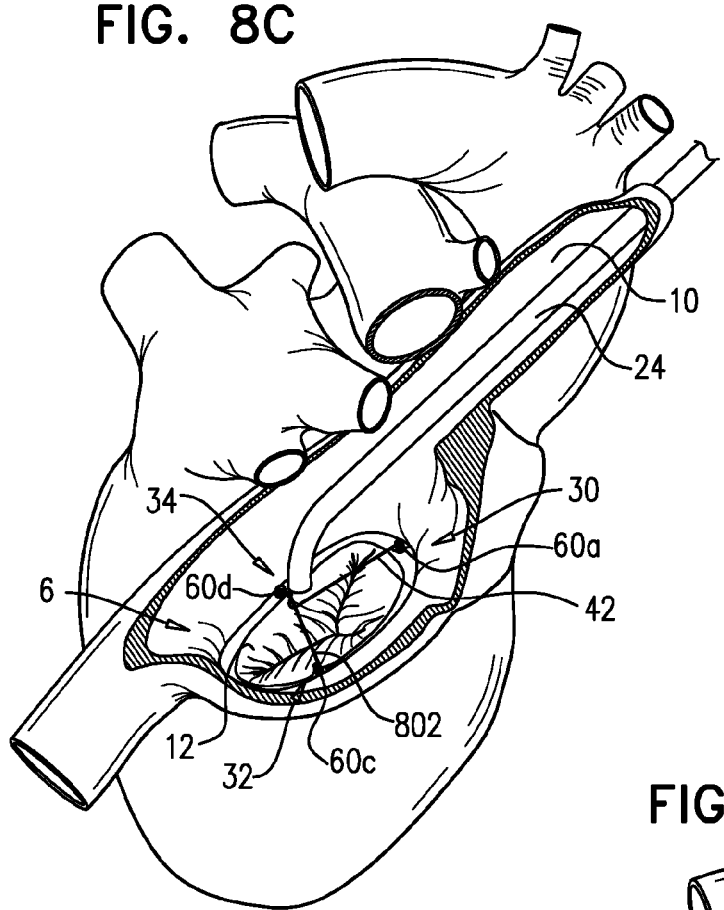
Figure 9C:
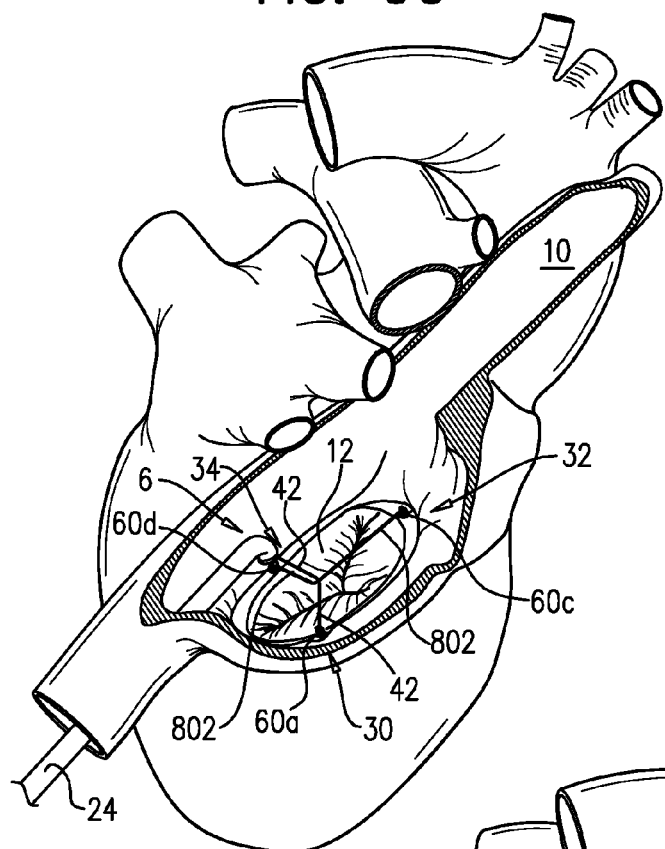

As shown in FIGS. 8C and 9C, the distal end of anchor-deployment tube 24 is advanced to a fourth implantation site 34. As mentioned above, longitudinal sub-member 802 extends between tissue-engaging elements 60c and 60d. As fourth tissue-engaging element 60d is brought to fourth implantation site 34, longitudinal sub-member 802 engages, e.g., becomes hooked on or looped over, longitudinal member 42 at junction 804. Fourth tissue-engaging element 60d is deployed at fourth implantation site 34, such as using anchoring techniques described herein. Fourth implantation site 34 includes a portion of cardiac tissue in the vicinity of tricuspid valve 4 (e.g., a second portion of tissue of the annulus of tricuspid valve 4, as shown). For example, in the approaches shown in FIGS. 8C and 9C, fourth implantation site 34 may be on septal side of the annulus of the valve (e.g., at the caudal part of the base of septal leaflet 12, approximately centered between two of the commissures of the valve. Alternatively, although typically less desirable, fourth implantation site 34 may be approximately at a commissure of the valve.

Figure 8D:
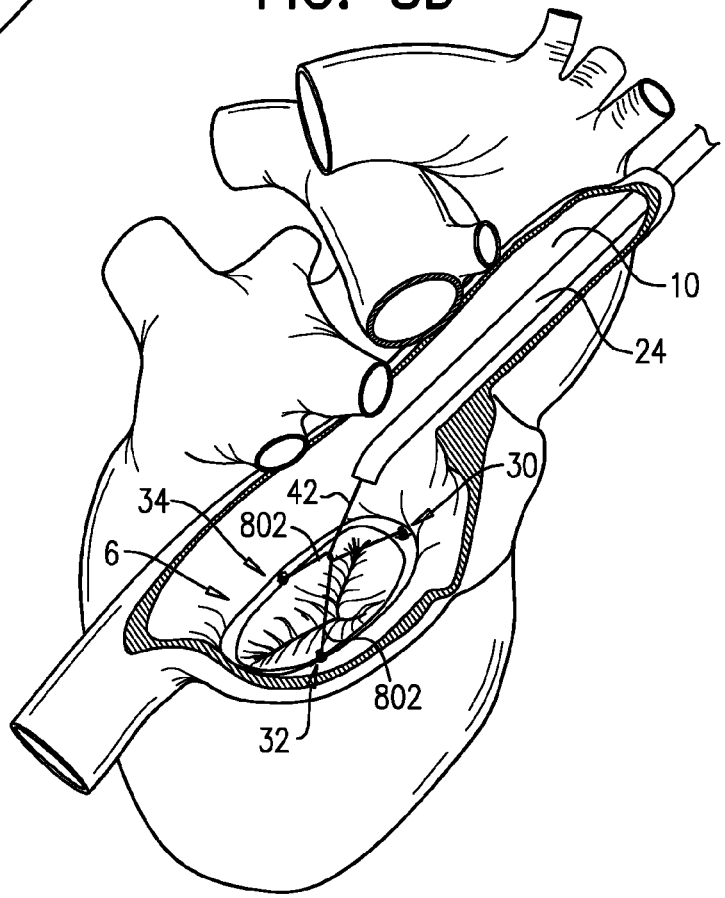
Figure 8E:
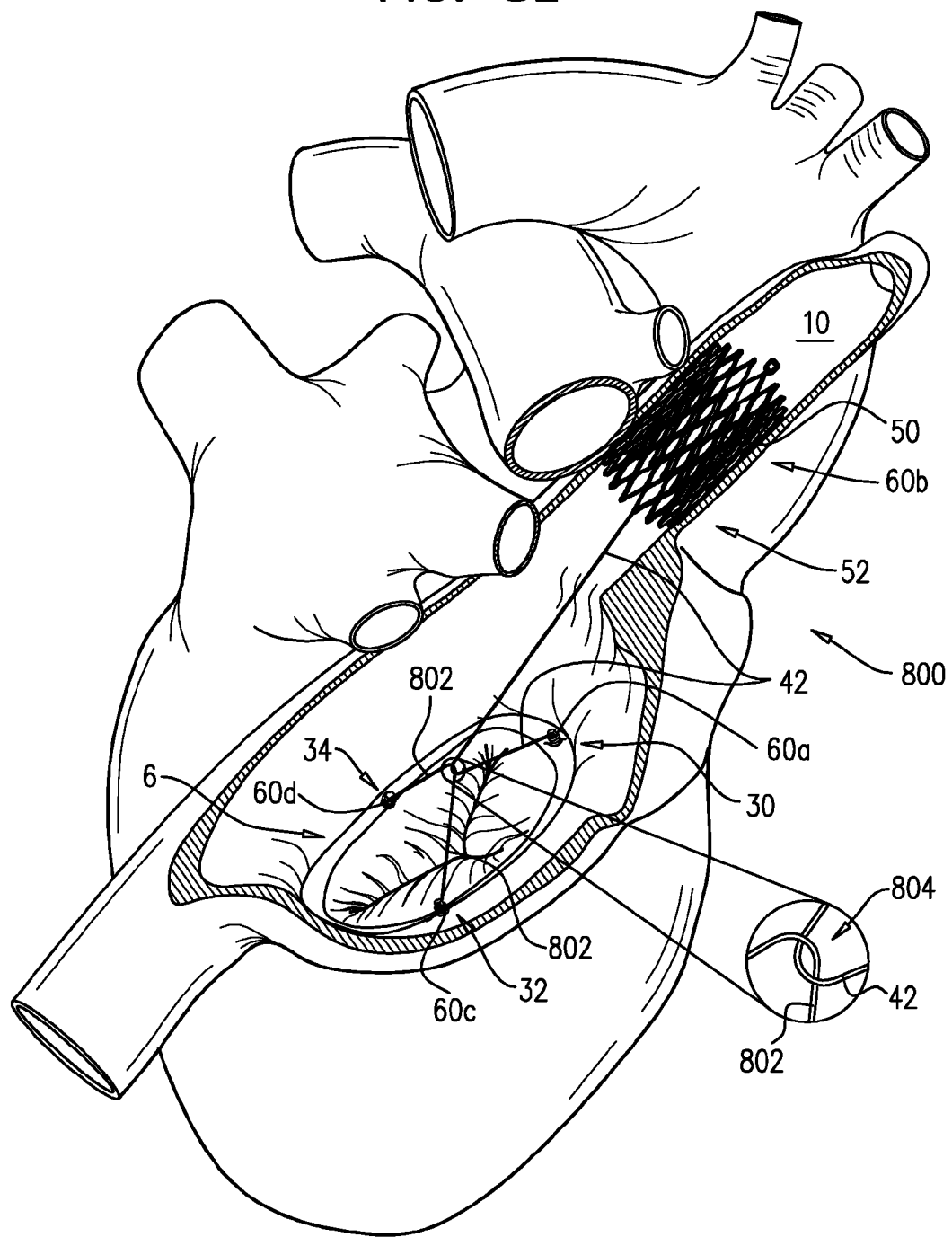
Figure 9D:
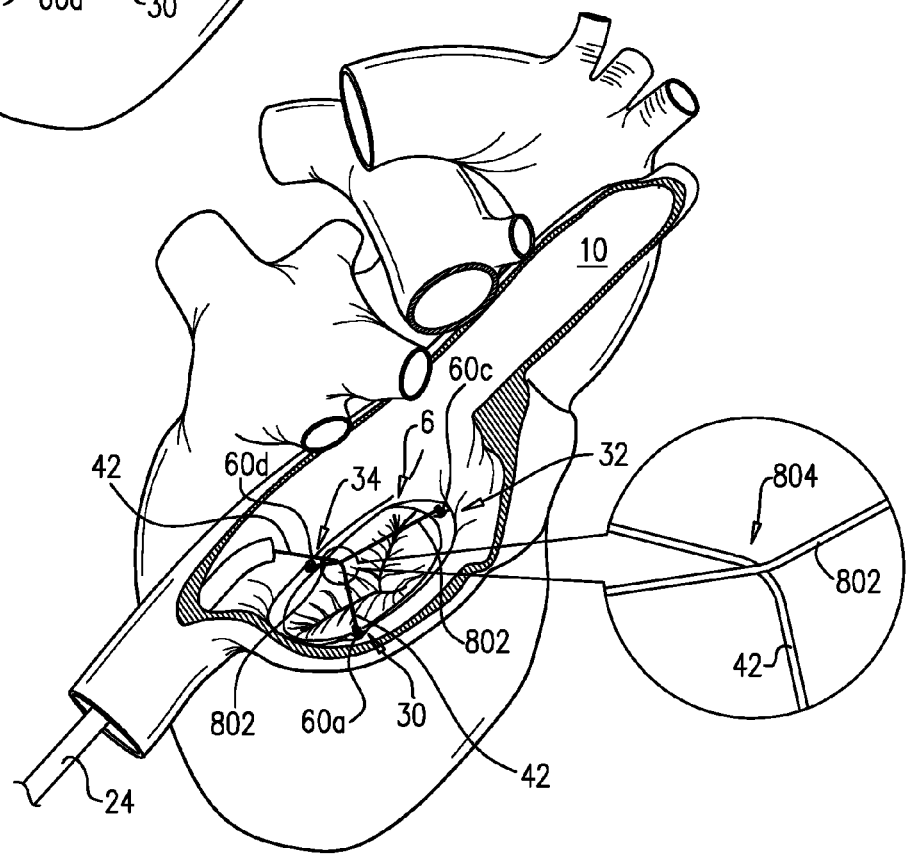
Figure 9E:
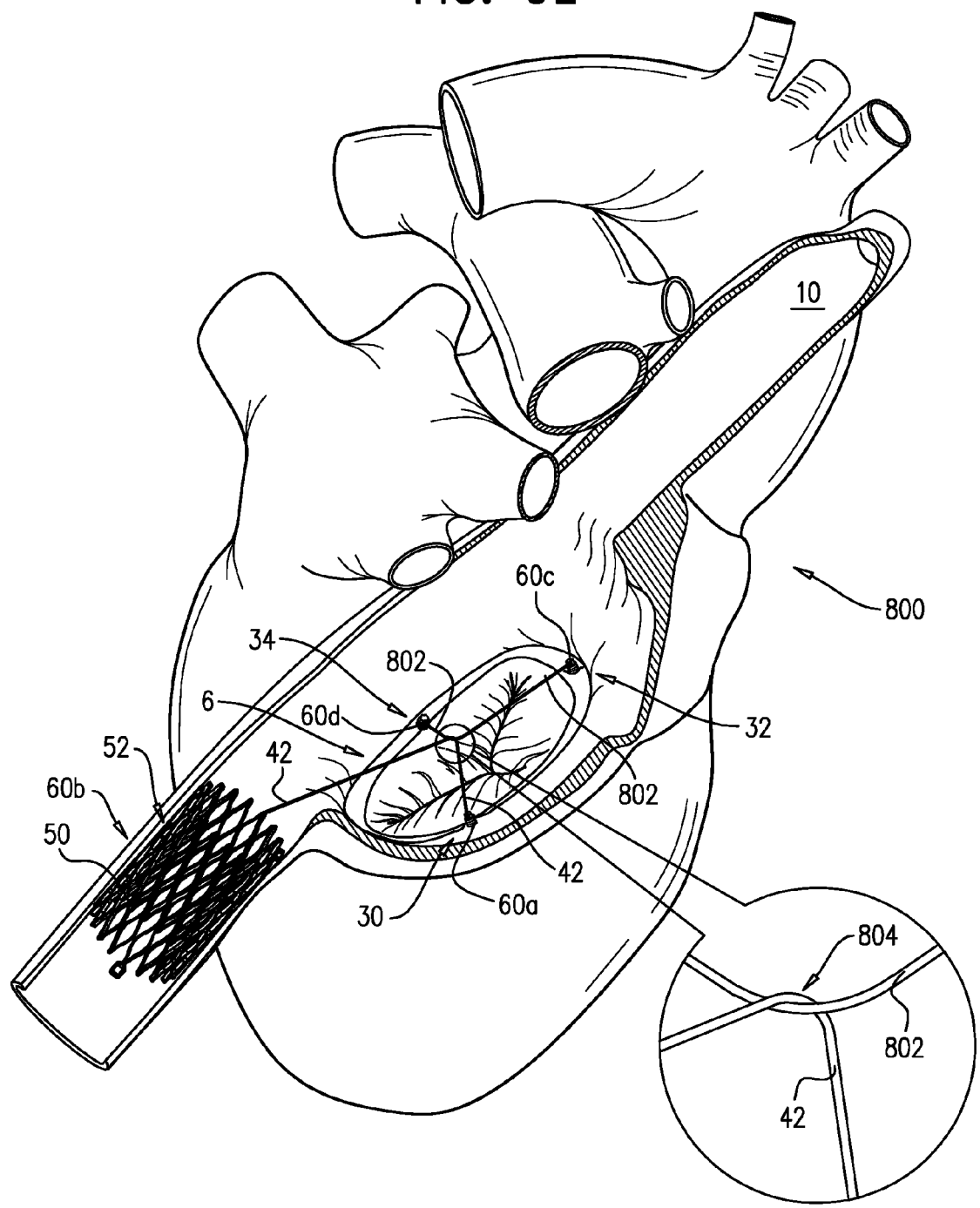

As shown in FIGS. 8D and 9D, anchor-deployment tube 24 is withdrawn into the vena cava. Second tissue-engaging element 60b (stent 50) pulls on longitudinal member 42, which directly pulls on first tissue-engaging element 60a, and indirectly pulls on tissue-engaging elements 60c and 60d via longitudinal sub-member 802. Responsively, a distance between the leaflets of tricuspid valve 4 is adjusted to reduce and eliminate regurgitation through valve 4, and thereby, valve 4 is repaired. For some applications, during the pulling of longitudinal member 42, a level of regurgitation of tricuspid valve 4 is monitored. Longitudinal member 42 is pulled until the regurgitation is reduced or ceases. Once the physician determines that the regurgitation of valve 4 is reduced or ceases, and valve 4 has been repaired, second tissue-engaging element 60b (e.g., stent 50) is deployed from anchor-deployment tube 24 in the vena cava, such as described hereinabove, thereby implanting the tissue-engaging element at second implantation site 52, as shown in FIGS. 8E and 9E.

For some applications, stent 50 comprises a plurality of interconnected superelastic metallic struts, such as described hereinabove with reference to FIG. 1D. Alternatively or additionally, for some applications, stent 50 comprise two or more rings 62, configured as described hereinabove with reference to FIGS. 1E-G.

For some applications, following the implantation the tissue-engaging elements at their respective implantation sites, as described hereinabove, a length of longitudinal member 42 is adjusted by an adjustable mechanism, as described hereinabove with reference to FIGS. 5A-B or 5C. Adjusting mechanism 150 typically comprises a mechanical element which shortens a length of longitudinal member 42. For some applications, adjustable mechanism 150 may be permanently coupled to longitudinal member 42; mechanism 150 comprises an adjusting element, e.g., a spool for looping a portion of longitudinal member 42 therearound, a crimping bead for crimping and shortening the portion of longitudinal member 42, a ratchet element, or a deforming element which deforms the portion of longitudinal member 42. For other applications, adjusting mechanism 150 comprises only adjusting tool 144, as shown in FIG. 5A. In such applications, adjusting tool 144 may comprise an adjusting element, e.g., a crimping bead for crimping and shortening the portion of longitudinal member 42, or a deforming element which deforms the portion of longitudinal member 42. In either application, a level of regurgitation of valve 4 may be monitored during the adjusting of the length of longitudinal member 42.

Figure 10A:
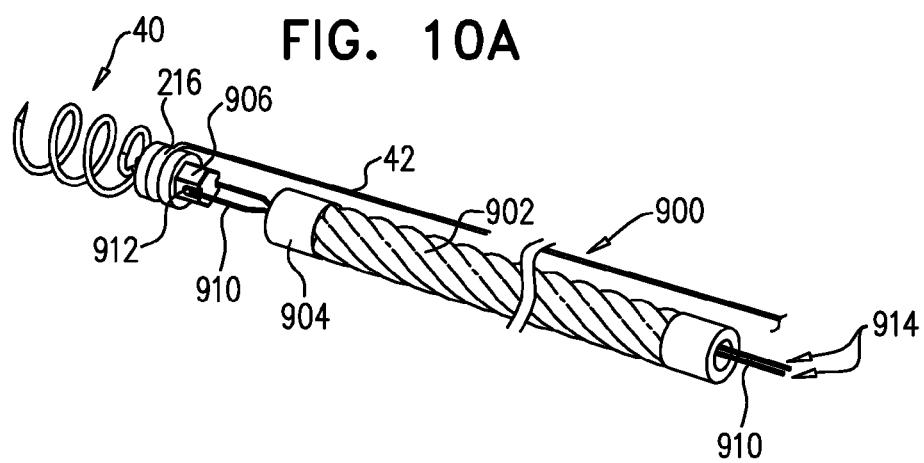
FIGS. 10A-B are schematic illustrations of a rotation tool, in accordance with an application of the present invention.
Figure 10B:
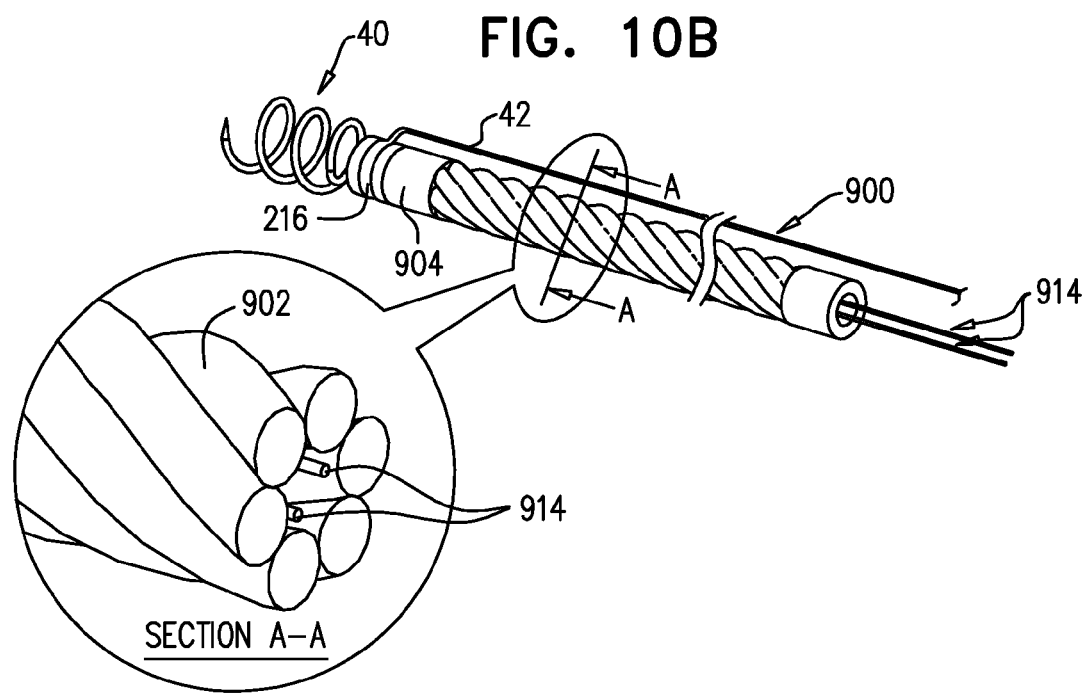

Reference is now made to FIGS. 10A-B, which are schematic illustrations of a rotation tool 900, in accordance with an application of the present invention. Tool 900 may be used to rotate a tissue anchor for driving the anchor into tissue. Tool 900 may be used, for example, to rotate and implant an anchor in combination with the applications described herein with reference to FIGS. 1A-G, 2A-B, 3A-C, 5A-C, 6, 8A-E, 9A-E, 11A-B, 12A-D, and/or 14A-D. Tool 900 is similar is some respect to delivery tool system 200, described hereinabove with reference to FIGS. 7A-D, and may optionally implement various features of system 200, and/or be utilized in a manner similar to system 200.

Tool 900 comprises a rotation tube 902, a distal end 904 of which is configured to removably engage a proximal coupling head 906 of anchor 40. Rotation of rotation tube 902 rotates the anchor. For example, distal end 904 may be shaped so as to define a female coupling member (which may, for example, be hexagonal or square), and proximal coupling head 906 may be shaped so as to define a male coupling element (which may, for example, be hexagonal or square). For some applications, rotation tube 902 comprises a braided or woven material, which may comprise, for example, a metal, such as stainless steel.

For some applications, such as described hereinabove with reference to FIGS. 7A-D, a distal end of longitudinal member 42 comprises annular loop 216, through which a portion of anchor 40 is coupled to the distal end of longitudinal member 42. This coupling arrangement of anchor 40 to annular loop 216 enables anchor 40 to rotate about a central longitudinal axis of rotation tool 900, freely within annular loop 216. That is, rotation tool 900 rotates anchor 40 without rotating longitudinal member 42 and stent 50 (if provided, such as described with reference to FIGS. 7A-D).

For some applications, tool 900 further comprises an elongated coupling element 910, which may comprise, for example, a string, cable, or wire. Anchor 40, such as proximal coupling head 906 thereof, is shaped so as to define a passage 912 therethrough. Elongated coupling element 910 is initially disposed so as to pass through passage 912, such that both ends 914 of the elongated coupling element extend in a proximal direction. When thus positioned, the elongated coupling element couples the tool to the anchor. To decouple the tool from the anchor, one of ends 914 is pulled until the elongated coupling element no longer passes through passage 912.

Reference is now made to FIGS. 11A-B and 12A-D, which are schematic illustrations of a system 950 for repairing tricuspid valve 4, in accordance with some applications of the present invention. System 950 typically comprises a tensioning device 952 and a deployment tube 954. For some applications, tube 954 is steerable, as is known in the catheter art, while for other applications, a separate steerable element may be coupled to tube 954. FIGS. 11A-B show system 950 with tensioning device 952 partially and fully deployed from deployment of deployment tube 954, respectively, and FIGS. 12A-B and 12C-D show two exemplary procedures for deploying tensioning device 952.

As shown in FIGS. 11A-B, tensioning device 952 comprises a first distal tissue-engaging element 60a and a second proximal tissue-engaging element 60b, and at least one flexible longitudinal member 42 that connects the tissue-engaging elements. First tissue-engaging element comprises tissue anchor 40, which is shown, by way of illustration, as comprising a helical tissue anchor. Anchor 40 may comprise any tissue anchor for puncturing or clamping cardiac tissue, including, but not limited to, the tissue anchors described hereinbelow with reference to FIGS. 13A-E. Second tissue-engaging element 60b comprises a radially-expandable anchor 956 that is configured to assume radially-compressed and radially-expanded state. When in its radially-expanded state, such as shown in FIG. 11B, anchor 956 is configured to rest against a wall of a cardiac chamber and to not pass through a hole in the cardiac wall. For example, when in its radially-expanded state, anchor 956 may be shaped like a flower or butterfly, and thus may be shaped so as to define a plurality of petals or wings. Typically, anchor 956 is configured to generally fall within exactly one plane when in its radially-expanded state.

Longitudinal member 42 passes through an opening defined by anchor 956, such that anchor 956 is slidably coupled to longitudinal member 42. Typically, a distance between first and second tissue-engaging elements 60a and 60b is adjusted by pulling longitudinal member 42 through the opening of anchor 956, which opening is typically positioned at a radial center of the anchor.

Once a desired distance has been obtained, the distance is maintained by locking anchor 956 to longitudinal member 42, so as to prevent movement of anchor 956 with respect to longitudinal member 42 at least in a proximal direction (away from distal tissue-engaging element 60a). For some applications, such as for deployment as described hereinbelow with reference to FIGS. 12C-D, at least a portion of longitudinal member 42 is shaped so as to define ratchet teeth 958, which engage anchor 956 so as to allow movement of anchor 956 with respect to longitudinal member 42 in a distal direction (toward first distal tissue-engaging element 60a), while preventing movement of anchor 956 with respect to longitudinal member 42 in a proximal direction (away from distal tissue-engaging element 60a). For other applications, such as for deployment as described hereinbelow with reference to FIGS. 12C-D, longitudinal member 42 is configured to move bidirectionally through anchor 956, and anchor 956 is configured to crimp longitudinal member 42 in place after the desired distance has been obtained, in order to lock anchor 956 to longitudinal member 42. For still other applications, such as for deployment as described hereinbelow with reference to FIGS. 12A-B, longitudinal member 42 is fixed to anchor 956, such as shown in FIG. 12B.

For some applications, first tissue-engaging element 60a and longitudinal member 42 are fabricated from the same material, e.g., nitinol, from a single piece. Typically, second tissue-engaging element 60b is fabricated from a second piece, and may comprise a shape-memory alloy, such as nitinol.

Reference is again made to FIGS. 12A-B, which illustrate a procedure for deploying tensioning device via a vena cava, such as superior vena cava 10 (as shown), or inferior vena cava 8 (approach not shown). Tensioning device 952 is initially positioned within deployment tube 954. For some applications, as shown in FIG. 12A, during an implantation procedure, deployment tube 954 is advanced into right atrium 6.

Figure 12A:
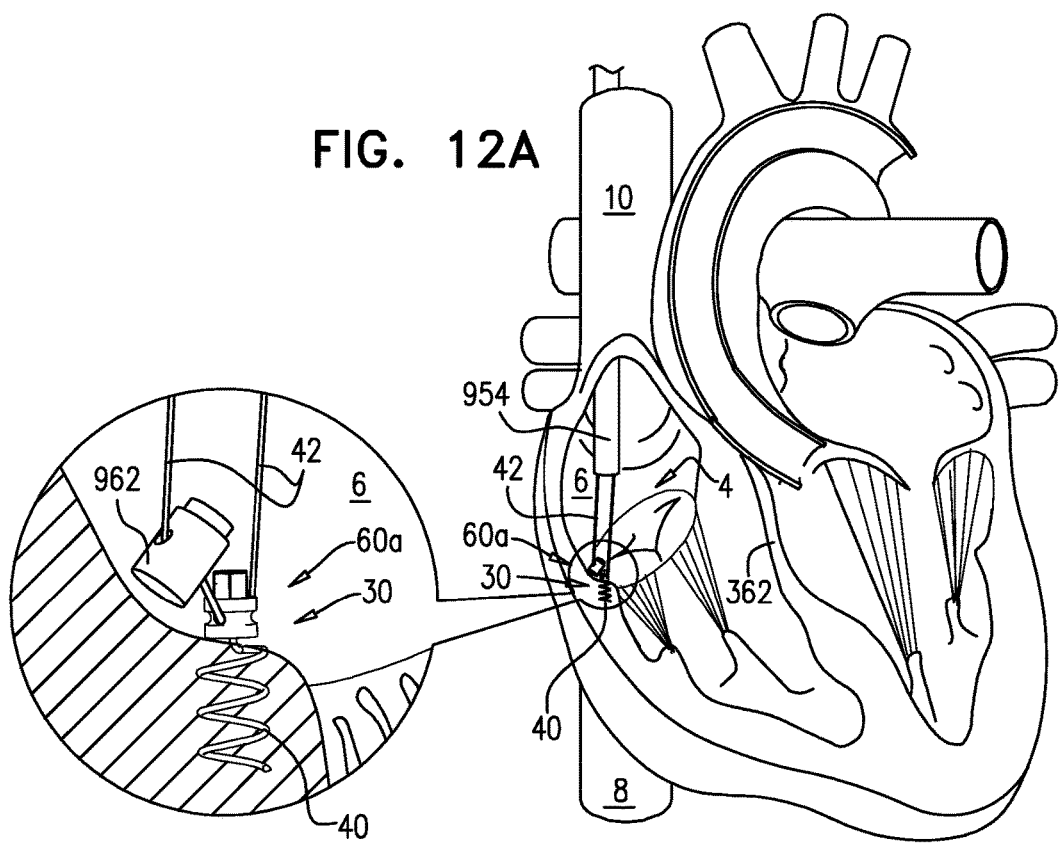
FIGS. 12A-D are schematic illustrations showing an exemplary procedure for deploying a tensioning device of the system of FIGS. 11A-B, in accordance with respective applications of the present invention.
Figure 12B:
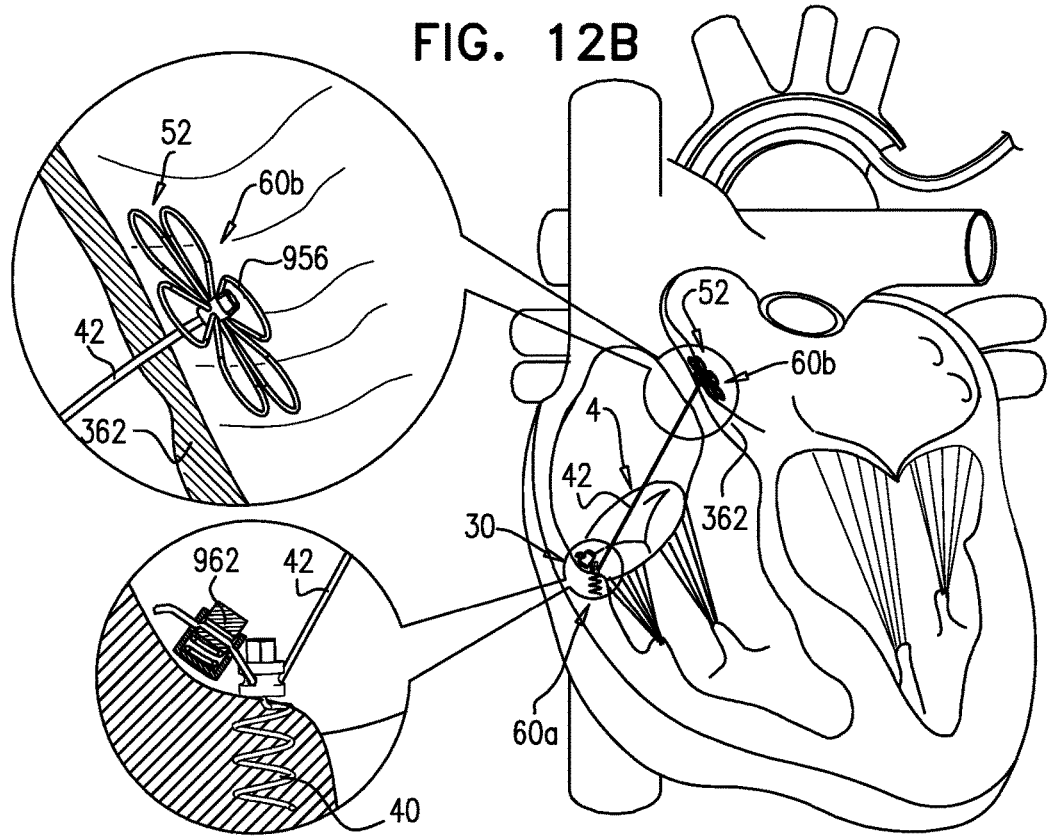

As shown in FIG. 12A, first distal tissue-engaging element 60a is deployed at first implantation site 30, such as using anchoring techniques described herein. First implantation site 30 includes a portion of cardiac tissue in the vicinity of tricuspid valve 4 (e.g., a first portion of tissue of the annulus of tricuspid valve 4, as shown). For example, first implantation site 30 may be on the mural side of the annulus (e.g., at posterior leaflet 16), approximately centered between two of the commissures of the valve. Alternatively, first implantation site 30 may be approximately at a commissure of the valve.

Prior to introducing the device, a hole is made in interatrial septum 362, typically using a separate perforation tool, such as a standard transeptal needle and kit. Deployment tube 954 is advanced to the right-atrial side of the hole (or, optionally, slightly through the hole), and second proximal tissue-engaging element 60b in the left atrium near septum 362, as shown in FIG. 12B. Typically, anchor 956 of second tissue-engaging element 60b self-expands upon being released from the deployment tube.

A distance between first and second implantation sites 30 and 52 is adjusted, such as by pulling longitudinal member 42 in a proximal direction (toward the vena cava). The decreased distance, and resulting increased tension, is maintained, such as using a locking mechanism 962. (For example, longitudinal member 42 may be tensioned by depressing a button of the locking mechanism and pulling the longitudinal member from the side of anchor 40; a spring may hold the button in a locked position when the button is not depressed.) Responsively, a distance between the leaflets of tricuspid valve 4 is adjusted to reduce and eliminate regurgitation through valve 4, and thereby, valve 4 is repaired. Optionally, a level of regurgitation of valve 4 may be monitored during the adjusting of the distance. Deployment tube 954 is withdrawn from the left atrium and the patient's body.

Alternatively, for some applications, a length of longitudinal member 42 is adjusted by an adjustable mechanism, as described hereinabove with reference to FIGS. 5A-B or 5C. Adjusting mechanism 150 typically comprises a mechanical element which shortens a length of longitudinal member 42. For some applications, adjustable mechanism 150 may be permanently coupled to longitudinal member 42; mechanism 150 comprises an adjusting element, e.g., a spool for looping a portion of longitudinal member 42 therearound, a crimping bead for crimping and shortening the portion of longitudinal member 42, a ratchet element, or a deforming element which deforms the portion of longitudinal member 42. For other applications, adjusting mechanism 150 comprises only adjusting tool 144, as shown in FIG. 5A. In such applications, adjusting tool 144 may comprise an adjusting element, e.g., a crimping bead for crimping and shortening the portion of longitudinal member 42, or a deforming element which deforms the portion of longitudinal member 42.

Alternatively, second proximal tissue-engaging element 60b is deployed before first distal tissue-engaging element 60a.

Figure 12C:
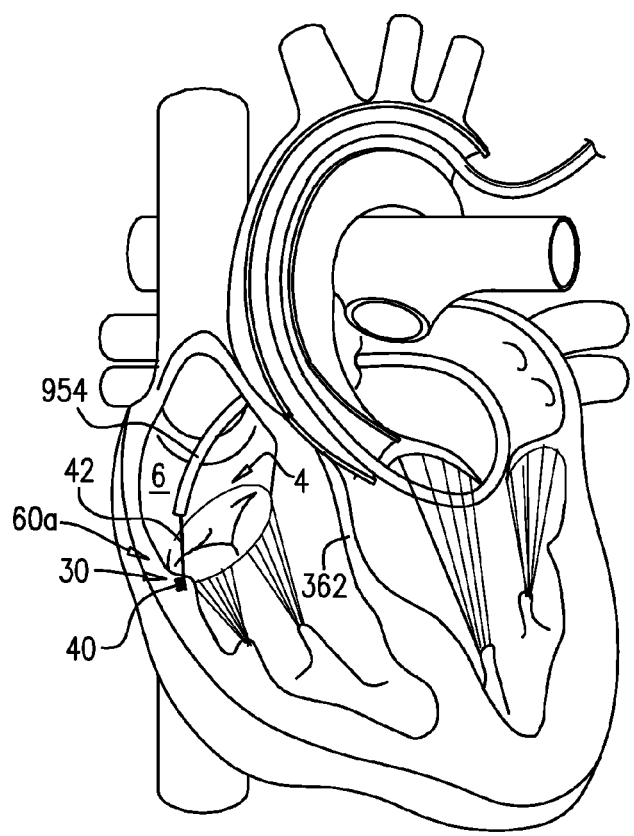

Reference is again made to FIGS. 12C-D, which illustrate a procedure for deploying tensioning device via a left atrium 960. Tensioning device 952 is initially positioned within deployment tube 954, such that first distal tissue-engaging element 60a is positioned near a distal end 959 of tube 954 and second proximal tissue-engaging element 60b is positioned more proximally within the tube, farther from the distal end thereof. For some applications, as shown in FIG. 12C, during an implantation procedure, deployment tube 954 is advanced into a left atrium 960. For example, the tube may be advanced to the left atrium via the aorta and left ventricle, as shown in the figure (the aorta may be accessed from the femoral artery or subclavian artery, for example). Alternatively, the tube may be advanced to the left atrium using a transapical approach through the left ventricle, as is known in the art.

Prior to introducing the device, a hole is made in interatrial septum 362, typically using a separate perforation tool, such as a standard transeptal needle and kit. Deployment tube 954 is advanced through the hole, until distal end 959 of the tube is positioned within right atrium 6, as shown in FIG. 12C.

As also shown in FIG. 12C, first distal tissue-engaging element 60a is deployed at first implantation site 30, such as using anchoring techniques described herein. First implantation site 30 includes a portion of cardiac tissue in the vicinity of tricuspid valve 4 (e.g., a first portion of tissue of the annulus of tricuspid valve 4, as shown). For example, first implantation site 30 may be on the mural side of the annulus (e.g., at posterior leaflet 16), approximately centered between two of the commissures of the valve. Alternatively, first implantation site 30 may be approximately at a commissure of the valve.

Figure 12D:
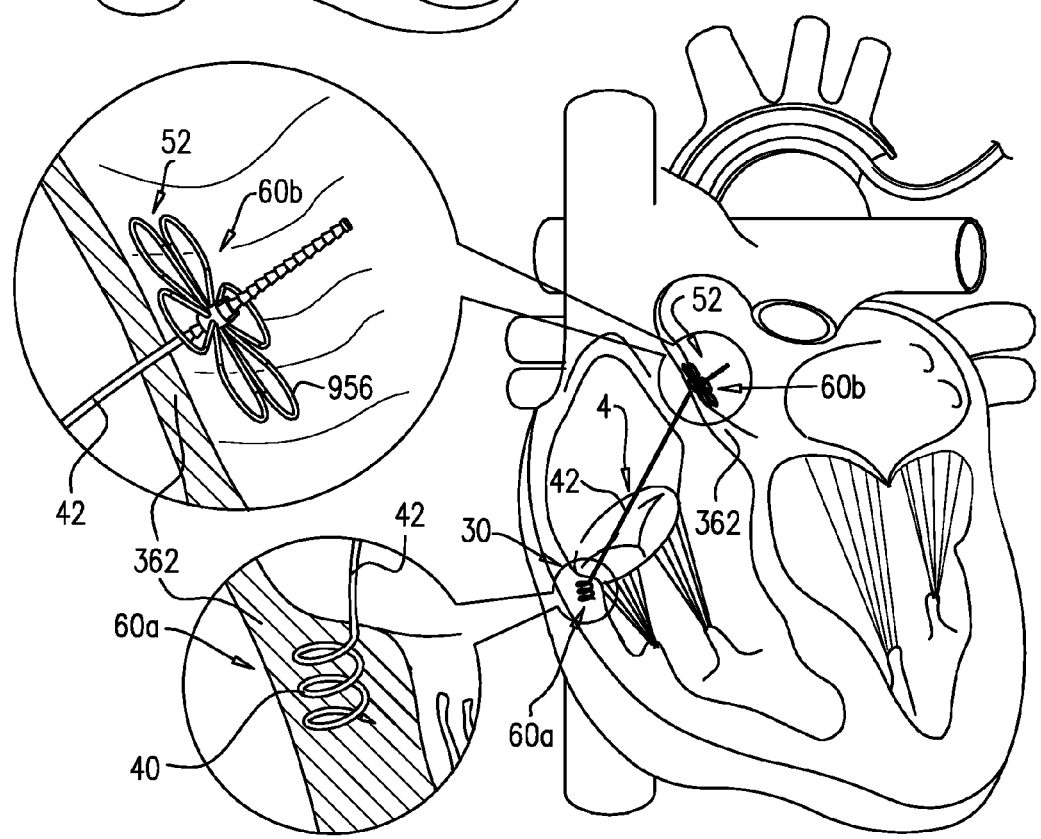

Deployment tube 954 is withdrawn proximally into left atrium 960, thereby releasing second proximal tissue-engaging element 60b in the left atrium near septum 362, as shown in FIG. 12D. Typically, anchor 956 of second tissue-engaging element 60b self-expands upon being released from the deployment tube. Anchor 956 of second tissue-engaging element 60b is held, such as using distal end 959 of deployment tube 954, at second implantation site 52 against the left-atrial side of septum 362 around the hole previously made in the septum. A distance between first and second implantation sites 30 and 52 is adjusted by pulling longitudinal member 42 in a proximal direction (toward left atrium 960), while holding anchor 956 against the left-atrial side of the septum, such as using distal end 959 of deployment tube 954. The decreased distance, and resulting increased tension, is maintained, such as described hereinabove with reference to FIGS. 11A-B. Responsively, a distance between the leaflets of tricuspid valve 4 is adjusted to reduce and eliminate regurgitation through valve 4, and thereby, valve 4 is repaired. Optionally, a level of regurgitation of valve 4 may be monitored during the adjusting of the distance. Deployment tube 954 is withdrawn from the left atrium and the patient's body.

Reference is now made to FIGS. 13A-E, which are schematic illustration of tissue anchors 40, in accordance with respective applications of the present invention. One or more of these anchors may be used as anchors 40 in the applications described hereinabove with reference to FIGS. 1A-G, 2A-B, 3A-C, 5A-C, 6, 8A-E, 9A-E, 10A-B, 11A-B, 12A-D, and/or 14A-D.

Figure 13A:
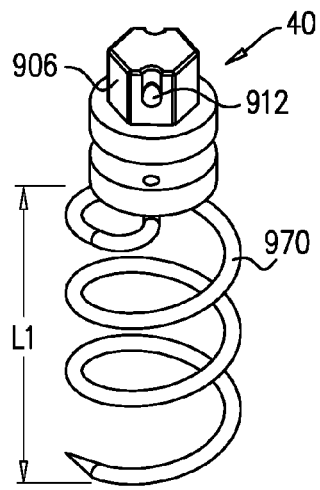
FIGS. 13A-E are schematic illustration of tissue anchors, in accordance with respective applications of the present invention.

In the configuration shown in FIG. 13A, anchor 40 comprises a helical tissue-coupling element 970 fixed to coupling head 906. Optionally, anchor 40, such as coupling head 906, is shaped so as to define passage 912, such as for use with the techniques described hereinabove with reference to FIGS. 10A-B. For some applications, a length L1 of tissue-coupling element 970 is at least 5 mm, no more than 30 mm, and/or between 5 and 30 mm, such as 10 mm.

Figure 13B:
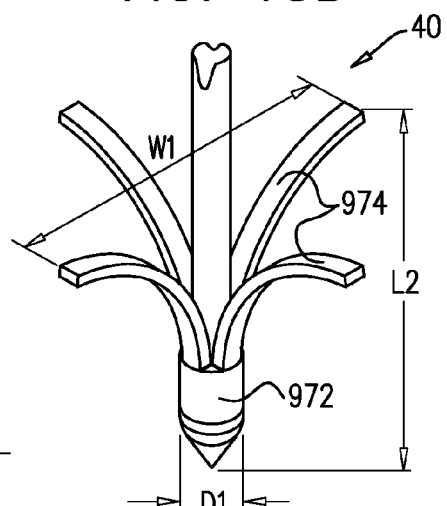

In the configuration shown in FIG. 13B, anchor 40 comprises a distal tissue-piercing tip 972 fixed to a plurality of arms 974, which extend from tip 972 in respective generally distal and radially-outward directions. The arms are inserted entirely into the tissue, thereby helping to couple the anchor to the tissue. For some applications, a greatest width W1 of anchor 40 is at least 6.5 mm, no more than 39 mm, and/or between 6.5 and 39 mm, such as 13 mm. For some applications, a length L2 of anchor 40, measured along an axis of the anchor from tips of arms 974 to the end of tip 972 of the anchor, is at least 5 mm, no more than 30 mm, and/or between 5 and 30 mm, such as 10 mm. For some applications, a greatest diameter D1 of tip 972 is at least 1 mm, no more than 6 mm, and/or between 1 and 6 mm, such as 2 mm.

Figure 13C:
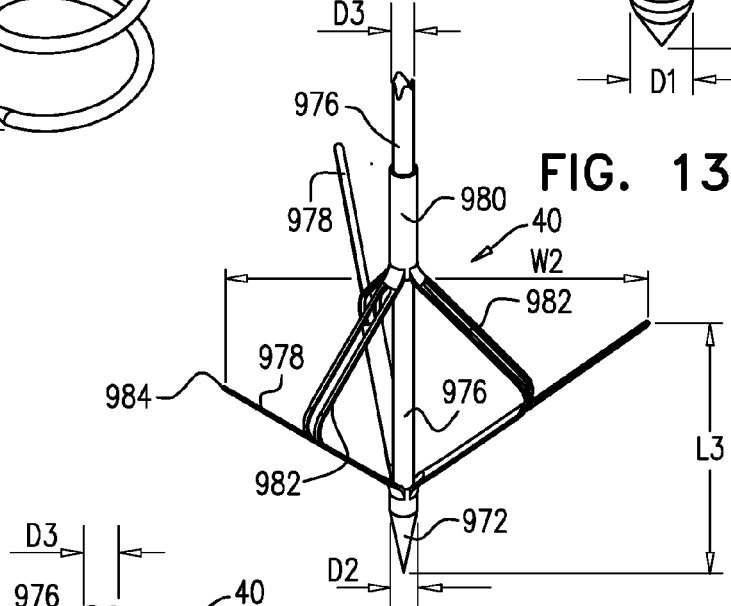
Figure 13D:
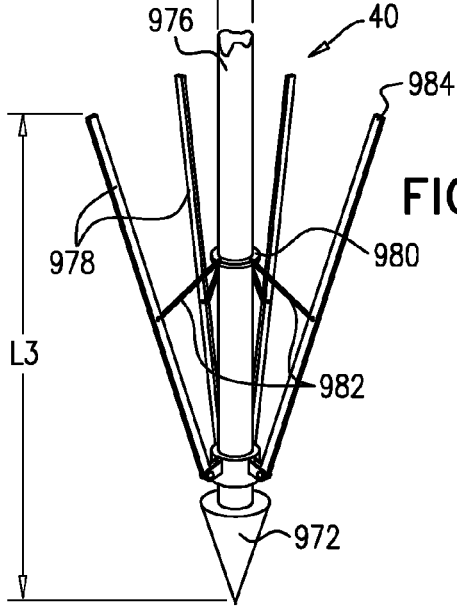

In the configurations shown in FIGS. 13C and 13D, anchor 40 is configured to radially contract and expand in a manner generally similar to that of an umbrella (but without the umbrella cloth). The anchor is inserted into the tissue in a radially-contracted (closed) state, and is transitioned to a radially-expanded (open) state, either automatically or by the surgeon, in order to fix the anchor within the tissue. For some applications, such as shown in FIG. 13C, the anchor is configured to assume the radially-expanded state when resting; the anchor is held in a radially-contracted state during deployment, and transitions to the radially-expanded state upon being released. For other applications, such as shown in FIG. 13D, the anchor is configured to assume the radially-contracted state when resting; the anchor is deployed in the radially-contracted state, and is actively transitioned to the radially-expanded state by the surgeon after being inserted into the tissue.

Anchor 40 comprises distal tissue-piercing tip 972, which is fixed at a distal end of a post 976 (which typically comprises a tube). The anchor further comprises a plurality of ribs 978 (e.g., three or four). Ribs 978 are coupled to the anchor near distal tip 972, such that the ribs can articulate with post 796, thereby changing respective angles between the ribs and the post. The anchor further comprises a runner 980 (which typically comprises a tube), which is slidably coupled to post 976, such that the runner can slide along the post. A plurality of stretchers 982 are coupled to runner 980 and respective ones of the ribs, such that stretchers can articulate with the runner and the respective ribs. Each of the stretchers may comprise one or more elongated elements; by way of example, each of the stretchers is shown comprising two elongated elements. Typically, tips 984 of ribs 978 (i.e., at the ends not coupled to the anchor) are blunt.

For some applications, such as the configuration shown in FIG. 13C, the anchor at least partially comprises a shape-memory alloy (e.g., nitinol), and the anchor's natural, resting state is the radially-expanded (open) state. The anchor is crimped inside a catheter so that it remains radially-contracted (closed) until deployed. Once deployed into the tissue, the catheter is pulled back and the anchor is allowed to open (i.e., automatically transition to the radially-expanded state).

For some applications, in order to allow retraction of the anchor (such as if the anchor has been improperly positioned, or needs to be removed for another reason), the proximal end of runner 980 (i.e., the end farther from tip 972) is removably coupled to an inner tube positioned within the catheter. For example, an outer surface of the proximal end of runner 980 and an inner surface of the inner tube near a distal end thereof may be threaded, to enable the removable coupling. Runner 980 thus remains coupled to the inner tube until released, such as by rotating the inner tube with respect to the runner (the tissue prevents the runner from also rotating). In order to retract the anchor, post 976 is pushed in a distal direction while the runner is still coupled to the inner tube, thereby moving post 976 with respect to runner 980 and transitioning the anchor back to its radially-contracted (closed) state. The anchor can thus be withdrawn into the catheter, repositioned, and deployed again at a different location. The surgeon rotates the inner tube to decouple the anchor once the location of the anchor has been finalized.

For some applications, in the configuration shown in FIG. 13D, anchor 40 further comprises a tube positioned around post 976, proximal to runner 980 (i.e., farther from tip 972). The tube is used to push runner 980 in a distal direction (toward the tip), in order to open the umbrella.

For some applications, a greatest width W2 of anchor 40, when radially expanded, is at least 6.5 mm, no more than 39 mm, and/or between 6.5 and 39 mm, such as 13 mm. For some applications, a length L3 of anchor 40, measured along an axis of the anchor from tips 984 of ribs 978 to the end of tip 972 of the anchor when the anchor is radially expanded, is at least 5 mm, no more than 30 mm, and/or between 5 and 30 mm, such as 10 mm. For some applications, a greatest diameter D2 of tip 972 is at least 0.4 mm, no more than 2.4 mm, and/or between 0.4 and 2.4 mm, such as 0.8 mm. For some applications, a greatest diameter D3 of post 976 is at least 0.3 mm, no more than 1.8 mm, and/or between 0.3 and 1.8 mm, such as 0.6 mm. For some applications, each of ribs 978 has a length of at least 6 mm, no more than 20 mm, and/or between 6 and 20 mm, such as 10 mm.

Figure 13E:
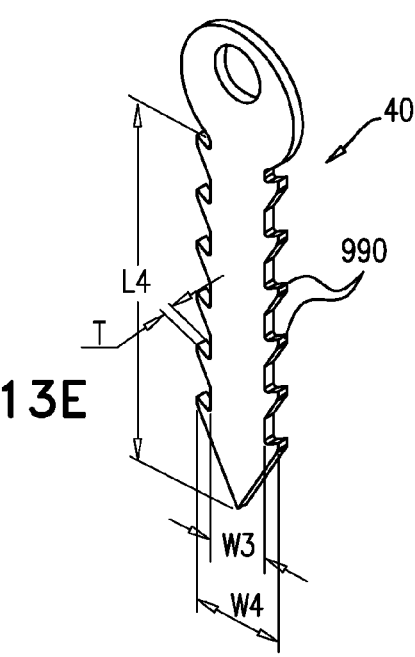

In the configuration shown in FIG. 13E, anchor 40 is barbed. For example, the anchor may be generally flat, and is shaped so as to define one or more barbs 990, which typically extend from both sides of the anchor. The barbs help couple the anchor to the tissue. For some applications, a greatest width W3 of anchor 40, excluding barbs 990, is at least 0.85 mm, no more than 5.1 mm, and/or between 0.85 and 5.1 mm, such as 1.7 mm. For some applications, a greatest width W4 of anchor 40, including barbs 990, is at least 1.25 mm, no more than 7.5 mm, and/or between 1.25 and 7.5 mm, such as 2.5 mm. For some applications, a length L4 of anchor 40, measured along an axis of the anchor from a distal end of the barbed portion to the proximal tip of the anchor, is at least 5 mm, no more than 30 mm, and/or between 5 and 30 mm, such as 9.5 mm. For some applications, a greatest thickness T of anchor 40 is at least 0.1 mm, no more than 0.6 mm, and/or between 0.1 and 0.6 mm, such as 0.2 mm.

Reference is now made to FIGS. 14A-D, which are schematic illustrations of a system 1000 for reducing regurgitation of a heart valve, such as tricuspid valve 4, and an exemplary deployment procedure, in accordance with some applications of the present invention. System 1000 comprises first and second tissue-engaging elements 60a and 60b, which comprise first and second tissue anchors 40a and 40b, respectively. It is to be noted that tissue anchors 40a and 40b comprise a helical tissue anchors by way of illustration and not limitation and that tissue anchors 40a and 40b may comprise any tissue anchor for puncturing or clamping cardiac tissue, including, but not limited to, the tissue anchors described hereinbelow with reference to FIGS. 13A-E, modified as described hereinbelow. First and second tissue anchors 40a and 40b are configured to be directly coupled to each other during an implantation procedure. For example, one of the tissue anchors (e.g., first tissue anchor 40a) may comprise a male coupling element 1002, and the other (e.g., second tissue anchor 40b) may comprise a female coupling element 1004 (shown in FIG. 14D).

Figure 14A:
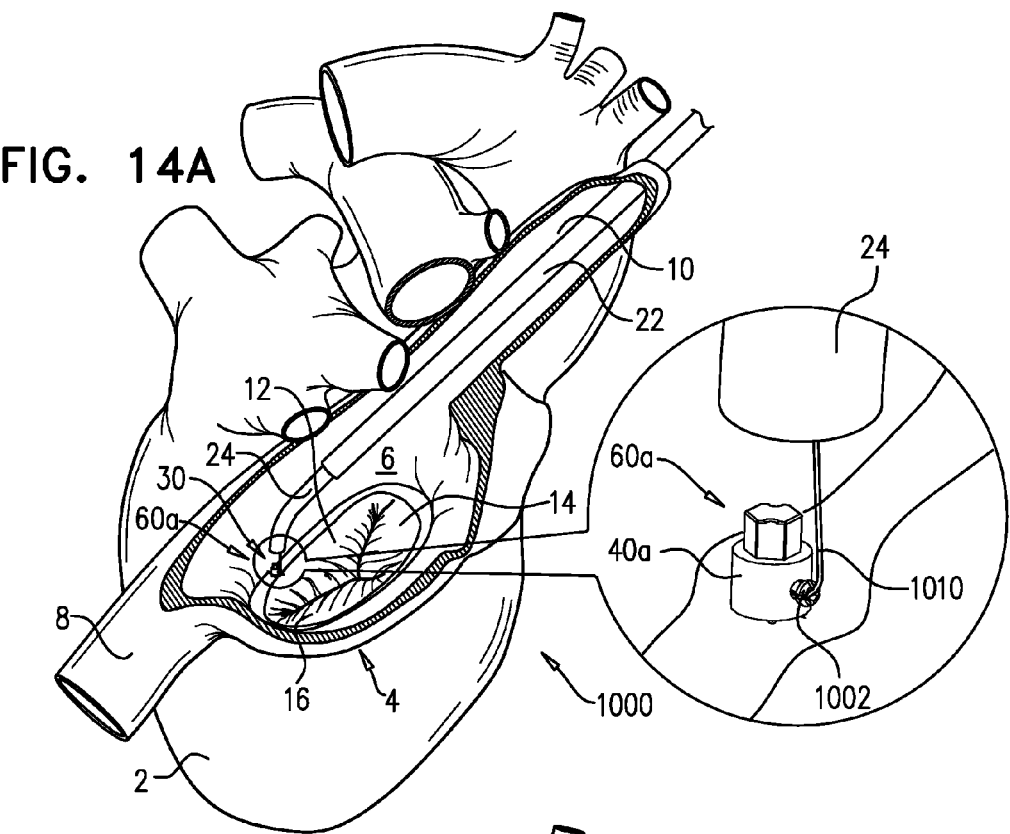
FIGS. 14A-D are schematic illustrations of apparatus for reducing regurgitation of a heart valve which comprises two tissue anchors configured to be directly coupled to each other, and an exemplary deployment procedure, in accordance with some applications of the present invention.

FIG. 14A shows the advancement of catheter 22 toward atrium 6 until distal end of the catheter is disposed within atrium 6. This portion of the procedure may be performed using techniques described hereinabove with reference to FIGS. 1A and 1E. Although the catheter is shown advanced through superior vena cava 10, the catheter may also be introduced through inferior vena cava 8. Once the distal end of catheter 22 is disposed within atrium 6, anchor-deployment tube 24 is extended from within catheter 22 toward first implantation site 30. Anchor-deployment tube 24 holds first tissue anchor 40a and at least a portion of a longitudinal member 1010, such as a wire, which is coupled to the anchor, typically removably. For some applications, tube 24 is steerable, as is known in the catheter art, while for other applications, a separate steerable element may be coupled to anchor-deployment tube 24. Under the aid of imaging guidance, anchor-deployment tube 24 is advanced toward first implantation site 30 until a distal end thereof contacts cardiac tissue of heart 2 at first implantation site 30. Anchor-deployment tube 24 facilitates atraumatic advancement of first tissue-engaging element 60a toward first implantation site 30.

First implantation site 30 is typically on the annulus of the valve. For example, first implantation site 30 may be on the annulus in the area between the coronary sinus and the base of septal leaflet 12, as shown. Alternatively, for example, first implantation site 30 may be on the annulus in the area of the antero-posterior commissure. Anchor 40a is fixed to the cardiac tissue, such as using techniques described hereinabove with reference to FIGS. 1B and 1E. Longitudinal member 1010 is typically removably coupled to anchor 40a, typically extending from male coupling element 1002, as shown in FIG. 14A.

Figure 14B:
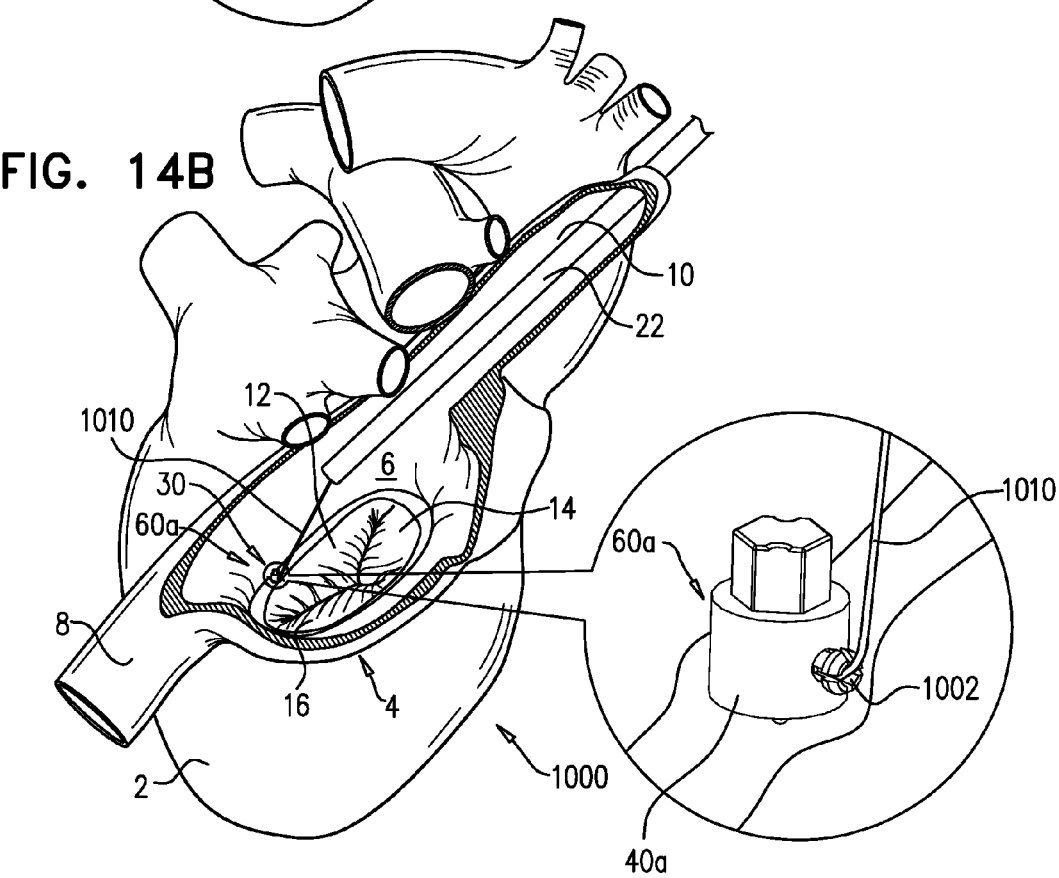

Anchor-deployment tube 24 is withdrawn from the atrium, as shown in FIG. 14B, leaving first tissue anchor 40a implanted in the annulus.

Second tissue anchor 40b is threaded onto longitudinal member 1010, by passing a proximal end of the longitudinal member (not shown) through a passage 1012 defined by anchor 40b. For some applications, a portion of passage 1012 is shaped so as to define female coupling element 1004. Second anchor 40b is loaded in anchor-deployment tube 24, or another anchor-deployment tube similar to anchor-deployment tube 24, which is advanced toward second implantation site 52 until a distal end thereof contacts cardiac tissue of heart 2 at first implantation site 52.

Figure 14C:
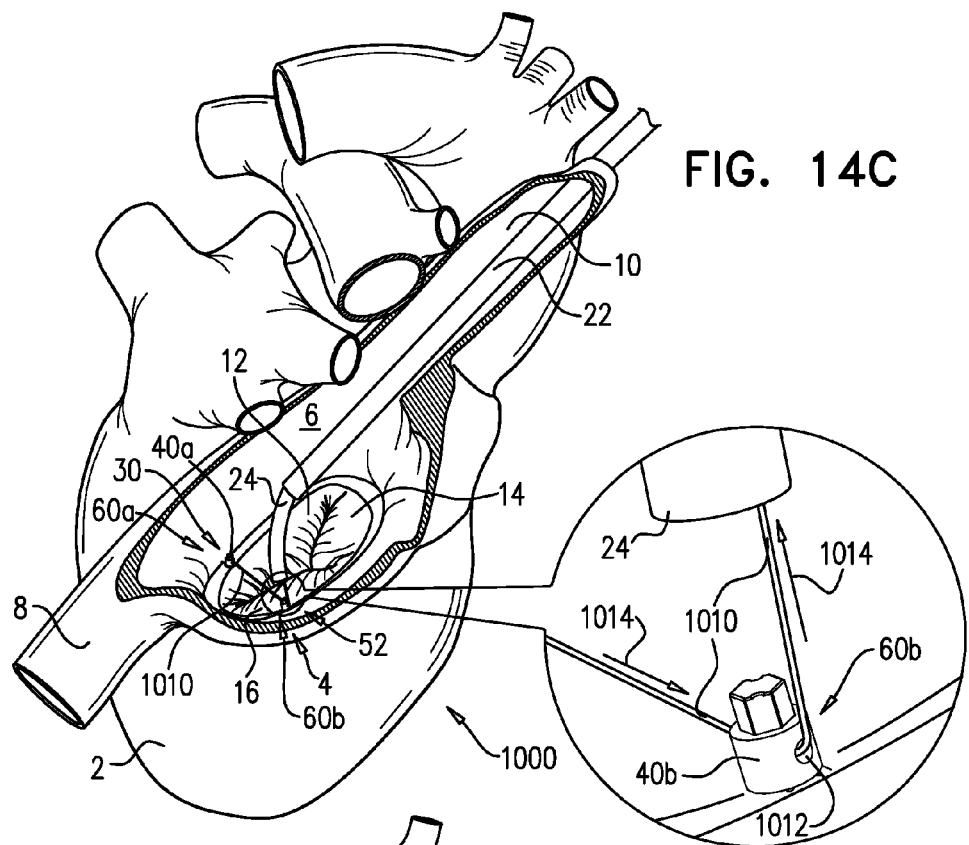

Second implantation site 52 is typically on the annulus of the valve. For example, second implantation site 52 may be on the annulus in the area of the antero-posterior commissure, as shown. Alternatively, for example, second implantation site 52 may be on the annulus in the area between the coronary sinus and the base of septal leaflet 12. As shown in FIG. 14C, second anchor 40b is fixed to the cardiac tissue, such as using techniques described hereinabove with reference to FIGS. 1B and 1E.

Figure 14D:
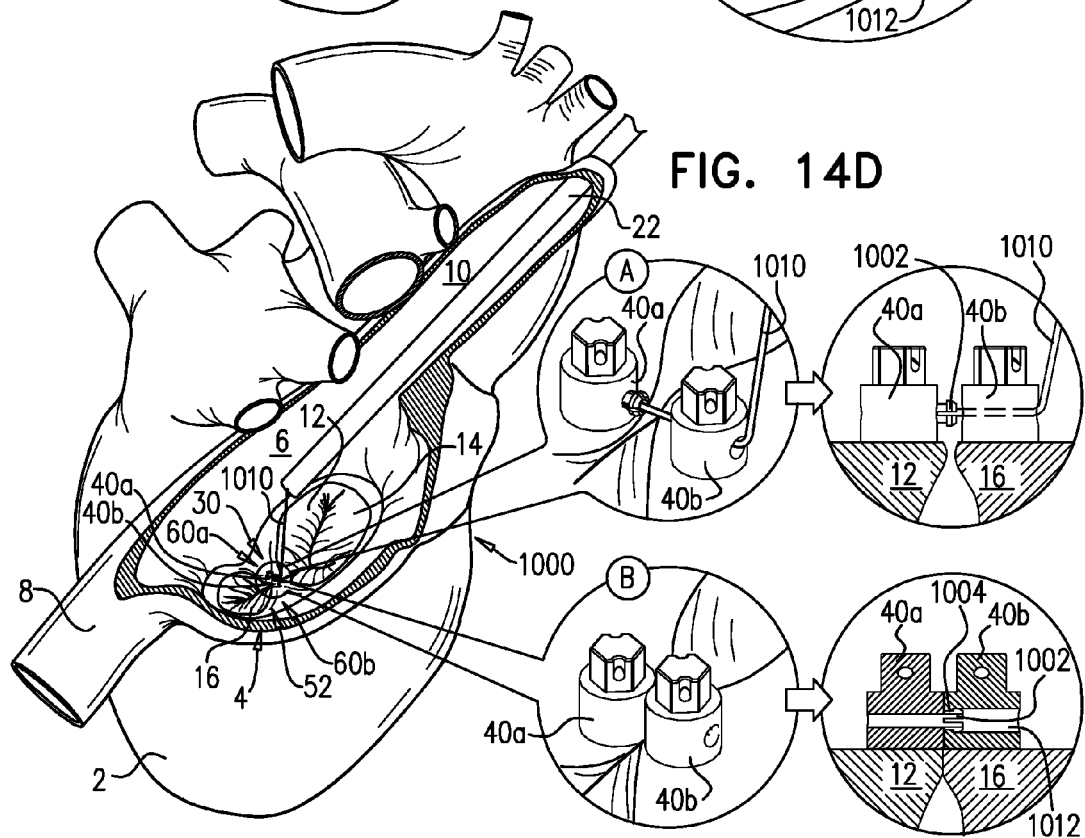

Tension is applied to longitudinal member 1010, by pulling the longitudinal member in a proximal direction, as schematically indicated by arrows 1014 in the blow-up in FIG. 14C. The resulting tension approximates first and second anchors 40a and 40b, as shown in blow-ups "A" in FIG. 14D, until the anchors are brought together, as shown in blow-ups "B" in FIG. 14D. Bringing the anchors together causes male coupling element 1002 of first anchor 40a to engage female coupling element 1004 of second anchor 40b, thereby directly coupling (i.e., locking) the anchors to each other. Drawing the anchors together draws the portions of the annulus to which they are coupled together, thereby achieving bicuspidization. For example, as shown in FIG. 14D, septal leaflet 12 and posterior leaflet 16 are drawn together. Typically, as shown in blow-ups "B" in FIG. 14D, longitudinal member 1010 is decoupled from first anchor 40a, such as by unscrewing the longitudinal member from the anchor, or using another decoupling technique. Alternatively, the longitudinal member is left coupled to the first anchor, and is cut off in the atrium.

Reference is now made to FIGS. 1A-G, 2A-B, 3A-C, 4A-C, 5A-C, 6, 7A-D, 8A-E, 9A-E, 10A-B, 11A-B, 12A-D, 13A-E, and 14A-D. It is to be noted that apparatus and methods described herein for repairing tricuspid valve 4 may also be applied to repair any other heart valve of the patient, e.g., a mitral valve, a pulmonary valve, or an aortic valve. For such applications, second implantation site 52 may include a portion of a blood vessel that is in contact with the left atrium of the patient, e.g., a pulmonary vein, a portion of the wall of the left atrium, a portion of the annulus of the mitral valve, or a portion of the left ventricle of the heart of the patient, and first implantation site 30 may include a portion of the wall of the left atrium, a portion of the annulus of the mitral valve, or a portion of the left ventricle of the heart of the patient.

Reference is again made to FIGS. 1A-G, 2A-B, 3A-C, 4A-C, 5A-C, 6, 7A-D, 8A-E, 9A-E, 10A-B, 11A-B, 12A-D, 13A-E, and 14A-D, it is to be noted that any suitable number of tissue-engaging elements 60 may be implanted in and/or grasp cardiac tissue, depending on the needs of a given patient. Typically, one or more tissue-engaging elements 60 is/are implanted in cardiac tissue (e.g., tissue of the annulus, tissue of the wall of the atrium adjacent the valve, or tissue of the wall of the ventricle adjacent the valve) in a vicinity of the valve that is between the middle of the anterior leaflet and the middle of the posterior leaflet, e.g., at the commissure between the middle of the anterior leaflet and the middle of the posterior leaflet. For such an application, pulling together implantation sites 30 and 52 pulls anterior leaflet 14 toward septal leaflet 12 and thereby achieves bicuspidization of tricuspid valve 4, it is to be noted, however, that tissue engaging elements 60 may be implanted in portions of tissue in the vicinity of any portion of the annulus of valve 4.

Reference is yet again made to FIGS. 1A-G, 2A-B, 3A-C, 4A-C, and 5A-C, 6, 7A-D, 8A-E, 9A-E, 12A-D, 13A-E, and 14A-D. It is to be noted that the adjustment of the distance between the respective implantation sites of the tissue-engaging elements 60 is facilitated by adjusting mechanism 150 following initial implantation of the tissue-engaging elements 60 and the repair of the valve and/or the adjustment of the heart wall geometry.

For some applications, techniques described herein are practiced in combination with techniques described in one or more of the references cited in the Background section of the present patent application.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method of reducing tricuspid valve regurgitation of a patient, the method comprising:
   implanting a first tissue anchor in the wall of the atrium above the annulus at an anterior leaflet or at a commissure between an anterior leaflet and a posterior leaflet at;
   implanting a second tissue anchor in the wall of the atrium above the annulus at a septal leaflet opposite the anterior leaflet at across the tricuspid valve; and
   using a spool that (a) winds therewithin at least a portion of a longitudinal member that couples the first and the second tissue anchors together and (b) is suspended along the longitudinal member hovering over the tricuspid valve away from the first and the second tissue anchors, applying tension between the first and the second tissue anchors to achieve bicuspidization of the tricuspid valve by rotating the spool.

2. The method according to claim 1, wherein the first and the second tissue anchors comprise respective helical tissue anchors.

* * * * *